(12) United States Patent
Kunimoto et al.

(10) Patent No.: US 10,487,050 B2
(45) Date of Patent: Nov. 26, 2019

(54) OXIME SULFONATE DERIVATIVES

(71) Applicant: BASF SE, Ludwigshafen (DE)

(72) Inventors: Kazuhiko Kunimoto, Kawanishi (JP);
Kaori Sameshima, Tondabayashi (JP);
Hisatoshi Kura, Takarazuka (JP); Yuki Matsuoka, Nishinomiya (JP)

(73) Assignee: BASF SE, Ludwigshafen (DE)

( * ) Notice: Subject to any disclaimer, the term of this patent is extended or adjusted under 35 U.S.C. 154(b) by 356 days.

(21) Appl. No.: 15/504,339

(22) PCT Filed: Aug. 13, 2015

(86) PCT No.: PCT/IB2015/056177
§ 371 (c)(1),
(2) Date: Feb. 16, 2017

(87) PCT Pub. No.: WO2016/030790
PCT Pub. Date: Mar. 3, 2016

(65) Prior Publication Data
US 2017/0260132 A1  Sep. 14, 2017

(30) Foreign Application Priority Data
Aug. 29, 2014  (EP) .................... 14182828

(51) Int. Cl.
*G02B 5/20* (2006.01)
*C07C 327/58* (2006.01)
(Continued)

(52) U.S. Cl.
CPC .......... *C07C 327/58* (2013.01); *C07D 209/48* (2013.01); *G02B 1/14* (2015.01);
(Continued)

(58) Field of Classification Search
CPC ...... C07C 327/58; C07D 209/48; G02B 1/14; G02B 5/201; G02B 5/223;
(Continued)

(56) References Cited

U.S. PATENT DOCUMENTS 5,368,976 A  11/1994  Tajima et al.
5,719,008 A   2/1998  Hozumi et al.
(Continued)

FOREIGN PATENT DOCUMENTS

| CN | 103019032 A | 4/2013 |
|---|---|---|
| EP | 0 048 615 A1 | 3/1982 |
| EP | 0 064 091 A1 | 11/1982 |
| EP | 0 126 541 A1 | 11/1984 |
| EP | 0 320 264 A2 | 6/1989 |
| EP | 0 339 841 A2 | 11/1989 |
| EP | 0 438 123 A2 | 7/1991 |
| EP | 0 441 232 A2 | 8/1991 |
| EP | 0 497 531 A2 | 8/1992 |
| EP | 0 780 729 A1 | 6/1997 |
| EP | 0 881 541 A1 | 12/1998 |
| EP | 0 902 327 A2 | 3/1999 |
| GB | 2 180 358 A | 3/1987 |
| JP | 48-15804 A | 2/1973 |
| JP | 57-16890 | 1/1982 |
| JP | 57-42009 A | 3/1982 |
| JP | 60-11409 A | 1/1985 |
| JP | 60-65072 | 4/1985 |
| JP | 1-130103 A | 5/1989 |
| JP | 1-134306 A | 5/1989 |

(Continued)

OTHER PUBLICATIONS

International Search Report dated Dec. 25, 2015 in PCT/IB2015/056177 filed Aug. 13, 2015.
Sunggak Kim et al., "Free Radical Acylation Approaches of C—H Bonds with 2-Chloroethylsulfonyl Oxime Ethers", Synlett, Special Issue, 2001, pp. 937-940.
Extended European Search Report dated Apr. 20, 2018 in Patent Application No. 15835348.2, 8 pages.

*Primary Examiner* — John A McPherson
(74) *Attorney, Agent, or Firm* — Oblon, McClelland, Maier & Neustadt, L.L.P.

(57) ABSTRACT

Oxime sulfonate compounds of the formula (I), wherein $R_1$ is $O(CO)R_4$, $COOR_5$ or $CONR_6R_7$; n is 1 or 2; $R_2$ for example is $C_1$-$C_8$alkyl, $C_3$-$C_6$cycloalkyl or benzyl; $R_3$ is for example $C_1$-$C_8$alkyl, $C_3$-$C_6$cycloalkyl, $C_1$-$C_8$haloalkyl, $C_2$-$C_8$alkenyl, benzyl, phenyl or naphthyl, which optionally are substituted; $R_4$ is for example $C_1$-$C_8$alkyl, $C_3$-$C_6$cycloalkyl, $C_1$-$C_8$haloalkyl, $C_2$-$C_8$alkenyl, benzyl, phenyl or naphthyl, which optionally are substituted; $R_5$ is for example $C_3$-$C_{20}$alkyl, $C_3$-$C_{14}$cycloalkyl, $C_2$-$C_8$alkenyl, $C_1$-$C_{12}$alkyl which is substituted for example by one or more halogen; or $R_5$ is phenyl or naphthyl, which are unsubstituted; $R_6$ and $R_7$ each independently of one another for example are hydrogen, $C_1$-$C_{12}$alkyl, $C_1$-$C_4$haloalkyl, phenyl-$C_1$-$C_4$alkyl, $C_2$-$C_8$alkenyl or $C_3$-$C_6$cycloalkyl, phenyl or naphthyl; or $R_6$ and $R_7$, together with the N-atom to which they are attached, form a 5- or 6-membered ring; are suitable as thermal radical initiators.

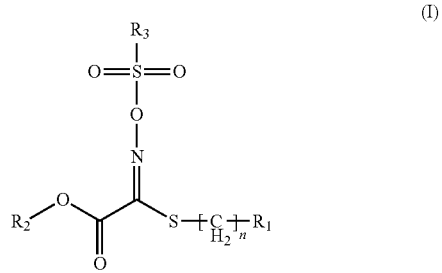

(I)

17 Claims, No Drawings

(51) Int. Cl.

| | | |
|---|---|---|
| *C07D 209/48* | (2006.01) | |
| *G03F 7/00* | (2006.01) | |
| *G03F 7/031* | (2006.01) | |
| *G03F 7/40* | (2006.01) | |
| *G02B 1/14* | (2015.01) | |
| *G02B 5/22* | (2006.01) | |
| *G02F 1/1335* | (2006.01) | |
| *G02F 1/1339* | (2006.01) | |
| *G03F 7/16* | (2006.01) | |
| *G03F 7/20* | (2006.01) | |
| *G03F 7/38* | (2006.01) | |

(52) U.S. Cl.
CPC .............. *G02B 5/201* (2013.01); *G02B 5/223* (2013.01); *G02F 1/1339* (2013.01); *G02F 1/133516* (2013.01); *G03F 7/0007* (2013.01); *G03F 7/031* (2013.01); *G03F 7/162* (2013.01); *G03F 7/168* (2013.01); *G03F 7/2002* (2013.01); *G03F 7/38* (2013.01); *G03F 7/40* (2013.01); *C07C 2601/20* (2017.05); *G02F 2001/133519* (2013.01)

(58) Field of Classification Search
CPC .............. G02F 1/133516; G02F 1/1339; G03F 7/0007; G03F 7/031; G03F 7/168; G03F 7/2002; G03F 7/38; G03F 7/40
See application file for complete search history.

(56) References Cited

U.S. PATENT DOCUMENTS

| | | | |
|---|---|---|---|
| 5,800,952 A | | 9/1998 | Urano et al. |
| 5,821,016 A | | 10/1998 | Satoh et al. |
| 5,847,015 A | | 12/1998 | Tajima et al. |
| 5,863,678 A | | 1/1999 | Urano et al. |
| 5,866,298 A | | 2/1999 | Iwamoto et al. |
| 5,879,855 A | | 3/1999 | Schadeli et al. |
| 5,882,843 A | | 3/1999 | Kudo et al. |
| 6,410,612 B1 | | 6/2002 | Hatanaka |
| 6,806,024 B1 | | 10/2004 | Kura et al. |
| 9,310,677 B2 | * | 4/2016 | Kunimoto ............ C07D 327/06 |
| 10,241,399 B2 | * | 3/2019 | Kunimoto ............ C07D 327/06 |
| 2004/0209186 A1 | | 10/2004 | Matsumoto et al. |
| 2013/0171415 A1 | * | 7/2013 | Sakita ............... C07D 307/78 428/155 |
| 2013/0308219 A1 | | 11/2013 | Kunimoto et al. |

FOREIGN PATENT DOCUMENTS

| | | |
|---|---|---|
| JP | 1-90516 U | 6/1989 |
| JP | 5-173320 A | 7/1993 |
| JP | 6-68309 A | 3/1994 |
| JP | 6-230212 A | 8/1994 |
| JP | 8-305019 A | 11/1996 |
| JP | 9-179299 A | 7/1997 |
| JP | 9-269410 A | 10/1997 |
| JP | 9-325209 A | 12/1997 |
| JP | 10-10718 A | 1/1998 |
| JP | 10-171119 A | 6/1998 |
| JP | 10-221843 A | 8/1998 |
| JP | 11-174459 A | 7/1999 |
| JP | 11-174464 A | 7/1999 |
| JP | 2000-81701 A | 3/2000 |
| JP | 2002-206014 A | 7/2002 |
| JP | 2002-538241 A | 11/2002 |
| JP | 2003-15288 A | 1/2003 |
| JP | 2003-330184 A | 11/2003 |
| JP | 2004-69754 A | 3/2004 |
| JP | 2004-302245 A | 10/2004 |
| JP | 2005-504013 A | 2/2005 |
| JP | 2005-77451 A | 3/2005 |
| JP | 2005-316449 A | 11/2005 |
| JP | 2005-338328 A | 12/2005 |
| JP | 3754065 B2 | 3/2006 |
| JP | 2009-86357 A | 4/2009 |
| JP | 2010-15025 A | 1/2010 |
| JP | 2010-49238 A | 3/2010 |
| JP | 2010-156881 A | 7/2010 |
| JP | 2011-215590 A | 10/2011 |
| JP | 2012-042836 A | 3/2012 |
| WO | WO 00/52530 A1 | 9/2000 |
| WO | WO 02/098870 A1 | 12/2002 |
| WO | 2005/080337 A1 | 9/2005 |
| WO | 2007/062963 A1 | 6/2007 |
| WO | 2007/071497 A1 | 6/2007 |
| WO | 2007/071797 A1 | 6/2007 |
| WO | 2008/078678 A1 | 7/2008 |
| WO | 2010/108835 A1 | 9/2010 |
| WO | 2012/101245 A1 | 8/2012 |

* cited by examiner

OXIME SULFONATE DERIVATIVES

The present invention relates to novel S-substituted oxime sulfonates having an ester of amide functionality in the S-substituent and a radically polymerizable composition comprising the oxime sulfonates used to manufacture liquid crystal display (LCD) or organic light emitting diode (OLED) display components requiring post-baking such as color filters (CF), overcoat, photospacer and interlayer dielectric. The invention further relates to the use of oxime sulfonates in other thermo-setting compositions.

There has been an increasing demand for color filters for LCD or OLED display. Currently, color filters for LCD or OLED, which comprises black matrix and red, green and blue color pixels on a glass substrate, are manufactured by photolithography using radically photopolymerizable resists. After the photolithographic process, thermal curing is performed at about 230° C. for 30 min to polymerize remaining acrylic double bonds to attain required durability in the production process of CF/LCD and for long-term survival in LCD as permanent coat.

An overcoat layer for LCD is used to planarize a surface of the color filter and enhance orientation of liquid crystal and to prevent ion elution from CF to the liquid crystal. As a base material for a colored coating film in a color filter, acrylic resins and/or epoxy resins or polyimide reins are usually employed. The overcoat is usually manufactured by heating, for example, at about 220° C. for 30 min or in combination with photolithoglaphy prior to the post-baking process. Thermal stability, light resistance, adhesiveness, hardness and transparency are required for the overcoat layer.

Spacer for LCD, which controls a cell gap of the liquid crystal layer in LCD panels, is formed with high positional precision by photolithography using a photosensitive composition. A photospacer is manufactured by photolithography using radically polymerizable resist on overcoat or color filter. After photolithography, the photospacer is baked, for example, at 220° C. for 60 min to attain thermal stability, mechanical strength, adhesiveness, cell gap controllability and high deformation restorability. A transparent column spacer has been widely used in the LCD technology, but the transparent spacer disturbs polarized light reducing the contrast ratio. One of a possible solution is to mix with a black colorant not to scatter but to absorb the polarized light, i.e. a black column spacer. Black column spacer is also used in the LCD technology.

In providing acceptable color filters, overcoat layers or spacers, a variety of curing compositions comprising a thermal curing promoter require long curing times and/or high curing temperatures. A high curing reactivity of the thermal curing promoter is desirable to shorten the curing times, lower the curing temperature and improve properties as permanent coat like high hardness, high solvent resistance, strong adhesion and low shrinkage.

A large number of organic substances belonging to the classes of peroxides or azo compounds are known for the application as thermal curing promoter to attain low curing temperatures. However, compositions comprising them often present difficulties concerning the storage stability and safety during transport due to their comparatively low decomposition temperature. Accordingly, there is a constant need for thermal curing promoters that meet the technical stability requirement. The thermal curing promoter should allow the curing of low temperature curable compositions and the reduction of curing time. The thermal curing promoter should show e.g. a good stability at the pre-baking process to remove the solvent prior to photolithography and enhancement of curing at an elevated temperature in the post-baking process after the photolithography.

JP10010718A discloses a color former, which includes organic peroxides as thermal polymerization initiators and production of a color filter having good solvent resistance by applying a post-baking process, preferably at 100-180° C., after photolithography process.

In JP2003330184A is described a colored photosensitive resin composition capable of forming a color filter having high heat resistance, high hardness and high solvent resistance even after the resin composition is subjected to heat treatment of comparatively low temperature. The resin is composed of a polymerization initiator having an oxadiazole structure or a triazine structure containing a trihalomethyl group.

JP2003015288A discloses a radiation sensitive composition, including thermal polymerization initiators like organic peroxides, hydroperoxide and azo compounds, capable of forming a color filter having satisfactory adhesion to a plastics substrate even if such low temperature treatment as not to cause deformation or yellowing to the plastics substrate is adopted when the color filter is formed on the plastics substrate. The radiation sensitive composition contains (A) a colorant, (B) an alkali-soluble resin, (C) a polyfunctional monomer, (D) a photopolymerization initiator and (E) a thermal polymerization initiator.

WO2010108835 discloses the use of hydroxylamine esters as thermal radical initiators for radically polymerizable compositions to manufacture color filters at lower temperature and/or in shorter time in the thermal curing (post baking) process which takes place after the photo curing process.

WO2012101245 discloses specific oxime sulfonates as thermal curing promoter for radically polymerizable compositions to show higher curing reactivity than known curing promoters such as peroxides or azo compounds.

The properties as permanent coat can be improved by adding efficient thermal curing promoters, but reduction of volatile species during post-baking is desired to lower thermal shrinkage of the permanent coat and avoid pollution of the oven and the manufactured panel by deposition of the volatile decomposition fragments of the thermal curing promoter. Since the efficiency of the thermal curing promoter tends to decrease by increasing molecular weight, it is needed to reduce volatility of the fragments without increasing molecular weight.

It now has been found, surprisingly, that generation of volatile species during thermal curing can be significantly reduced by introducing an ester or amide functionality in the S-substituent of the S-substituted oxime sulfonates, which is used as thermal curing promoters for radically polymerizable compositions, without losing curing efficiency. Accordingly, subject of the invention are Compounds of the formula I

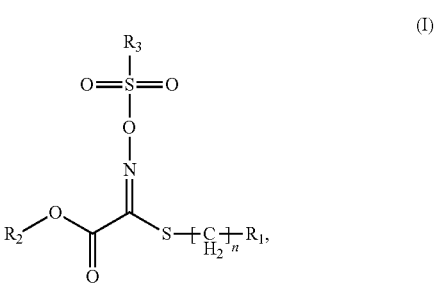

wherein

R₁ is O(CO)R₄, COOR₅ or CONR₆R₇;

n is 1 or 2;

$R_2$ is $C_1$-$C_8$alkyl, $C_2$-$C_8$alkyl which is interrupted by one or more O, or $C_3$-$C_6$cycloalkyl, which is uninterrupted or is interrupted by one or more O;

or $R_2$ is benzyl, which is unsubstituted or is substituted by one or more $C_1$-$C_6$alkyl, $C_1$-$C_4$haloalkyl, halogen, CN, NO₂, $C_1$-$C_6$alkylsulfanyl or $C_1$-$C_6$alkoxy;

$R_3$ is $C_1$-$C_8$alkyl, $C_3$-$C_6$cycloalkyl, $C_1$-$C_8$haloalkyl or $C_2$-$C_8$alkenyl;

or $R_3$ is benzyl, phenyl or naphthyl, which benzyl, phenyl or naphthyl is unsubstituted or substituted by one or more $C_1$-$C_6$alkyl, $C_1$-$C_4$haloalkyl, halogen, CN, NO₂, $C_1$-$C_6$alkylsulfanyl, $C_1$-$C_6$alkoxy, phenyl or COO($C_1$-$C_6$alkyl);

$R_4$ is $C_1$-$C_8$alkyl, $C_3$-$C_6$cycloalkyl, $C_1$-$C_8$haloalkyl or $C_2$-$C_8$alkenyl;

or $R_4$ is benzyl, phenyl or naphthyl, which benzyl, phenyl or naphthyl are unsubstituted or substituted by one or more $C_1$-$C_6$alkyl, $C_1$-$C_4$haloalkyl, halogen, CN, NO₂, $C_1$-$C_6$alkylsulfanyl, phenylsulfanyl, $C_1$-$C_6$alkoxy, phenoxy, phenyl or COO($C_1$-$C_6$alkyl);

$R_5$ is $C_3$-$C_{20}$alkyl, $C_3$-$C_{14}$cycloalkyl or $C_2$-$C_8$alkenyl;

or $R_5$ is $C_1$-$C_{12}$alkyl substituted by one or more halogen, CN, phenylsulfanyl, phenoxy, N($C_1$-$C_6$alkyl)₂, N(phenyl)₂, phthalimido, phenyl or phenyl substituted by one or more $C_1$-$C_{12}$alkyl, $C_1$-$C_4$haloalkyl, halogen, CN, NO₂, $C_1$-$C_6$alkylsulfanyl phenylsulfanyl, $C_1$-$C_6$alkoxy, phenoxy, N($C_1$-$C_6$alkyl)₂, N(phenyl)₂;

or $R_5$ is $C_2$-$C_{12}$alkyl or $C_3$-$C_6$cycloalkyl, each of which is interrupted by one or more O or S;

or $R_5$ is phenyl or naphthyl, which phenyl or naphthyl are unsubstituted or substituted by one or more $C_1$-$C_6$alkyl, $C_1$-$C_4$haloalkyl, halogen, CN, NO₂, $C_1$-$C_6$alkylsulfanyl, $C_1$-$C_6$alkoxy, phenyl or COO($C_1$-$C_6$alkyl);

$R_6$ and $R_7$ each independently of one another are hydrogen, $C_1$-$C_{12}$alkyl, $C_1$-$C_4$haloalkyl, phenyl-$C_1$-$C_4$alkyl, $C_2$-$C_8$alkenyl or $C_3$-$C_6$cycloalkyl, or $R_6$ and $R_7$ are $C_2$-$C_{12}$alkyl which is interrupted by O, S, N($C_1$-$C_8$alkyl) or CO, or $R_6$ and $R_7$ are $C_2$-$C_4$haloalkyl which is interrupted by O, S, N($C_1$-$C_8$alkyl) or CO, or $R_6$ and $R_7$ independently of each other are phenyl-$C_1$-$C_4$alkyl which is interrupted by O, S, N($C_1$-$C_8$alkyl) or CO;

or $R_6$ and $R_7$ are $C_2$-$C_8$alkenyl which is interrupted by O, S, N($C_1$-$C_8$alkyl) or CO or $R_6$ and $R_7$ are $C_3$-$C_6$cycloalkyl which is interrupted by O, S, N($C_1$-$C_8$alkyl) or CO, or $R_6$ and $R_7$ independently of each other are phenyl or naphthyl, which phenyl or naphthyl is unsubstituted or is substituted by one or more $C_1$-$C_6$alkyl, $C_1$-$C_4$haloalkyl, halogen, CN, NO₂, $C_1$-$C_6$alkylsulfanyl, $C_1$-$C_6$alkoxy, phenyl or COO($C_1$-$C_6$alkyl); or $R_6$ and $R_7$, together with the N-atom to which they are attached, form a 5- or 6-membered ring via $C_2$-$C_5$alkylene, which $C_2$-$C_5$alkylene ring is uninterrupted or interrupted by one or more O, S, N($C_1$-$C_8$alkyl), NH or CO.

$C_1$-$C_{12}$alkyl is linear or branched and is, for example, $C_1$-$C_8$-, $C_1$-$C_6$- or $C_1$-$C_4$alkyl. Examples are methyl, ethyl, propyl, isopropyl, n-butyl, sec-butyl, isobutyl, tert-butyl, pentyl, hexyl, heptyl, 2,4,4-trimethylpentyl, 2-ethylhexyl, octyl, nonyl, decyl, dodecyl.

$C_1$-$C_8$alkyl, $C_1$-$C_6$alkyl and $C_1$-$C_4$alkyl have the same meanings as given above for $C_1$-$C_{12}$alkyl up to the corresponding number of C-atoms.

$C_3$-$C_{20}$alkyl is linear or branched and is, for example, $C_3$-$C_{18}$-, $C_3$-$C_{14}$-, $C_3$-$C_{12}$-, $C_3$-$C_8$-, $C_3$-$C_6$- or $C_3$-$C_4$alkyl. Examples are propyl, isopropyl, n-butyl, sec-butyl, isobutyl, tert-butyl, pentyl, hexyl, heptyl, 2,4,4-trimethylpentyl, 2-ethylhexyl, octyl, nonyl, decyl, dodecyl, tetradecyl, pentadecyl, hexadecyl, octadecyl and icosyl.

$C_2$-$C_8$alkyl which is interrupted by one or more O is for example interrupted 1-5, 1-4 or three times or once or twice by O. In case the groups are interrupted by more than one O, said O-atoms are separated from one another by at least one methylene group, i.e. the O-atoms are non-consecutive. The alkyl groups in the interrupted alkyl are linear or branched. Examples are the following structural units —CH₂—O—CH₃, —CH₂CH₂—O—CH₂CH₃, —[CH₂CH₂O]$_y$—CH₃, with y=1-3, —(CH₂CH₂O)₃CH₂CH₃, —CH₂—CH(CH₃)—O—CH₂—CH₂CH₃, or —CH₂—CH(CH₃)—O—CH₂CH₃.

$C_2$-$C_{12}$alkyl which is interrupted by one or more S, N($C_1$-$C_8$alkyl) or CO is defined similar to the interrupted alkyl above, replacing the O atom by S, N($C_1$-$C_8$alkyl) or CO.

Also "mixed" interruptions are meant to be covered by the definition, that is, the $C_2$-$C_{12}$alkyl is interrupted by one or more O and/or S and/or N($C_1$-$C_8$alkyl) an/or CO.

$C_1$-$C_8$haloalkyl and $C_1$-$C_4$haloalkyl are linear or branched $C_1$-$C_8$ and $C_1$-$C_4$-alkyl mono- or poly-substituted by halogen, wherein the halogen atoms are either positioned at different C-atoms of the alkyl group or also at one C-atom. $C_1$-$C_8$ and $C_1$-$C_4$-alkyl being, for example, as defined above. The alkyl radical is for example mono- or polyhalogenated, up to the exchange of all H-atoms by halogen. Examples are chloromethyl, trichloromethyl, trifluoromethyl or 2-bromopropyl, especially trifluoromethyl or trichloromethyl.

$C_2$-$C_4$haloalkyl which is interrupted by O, S, N($C_1$-$C_8$alkyl) or CO, is defined similar as described above for interrupted alkyl. It is evident, that the interrupting atoms or groups are interrupting two carbon-carbon bonds and not a carbon-halogen bond.

$C_3$-$C_{14}$cycloalkyl is a mono- or polycyclic aliphatic ring, for example a mono-, bi- or tricyclic aliphatic ring, e.g. $C_3$-$C_{12}$—, $C_3$-$C_{10}$cycloalkyl. Examples of monocyclic rings are cyclopropyl, cyclopentyl, cyclohexyl, cyclooctyl, cyclododecyl, or cyclotetradecyl, especially cyclopentyl, cyclohexyl, cyclooctyl, cyclododecyl and cyclotetradecyl, preferably cyclohexyl and cyclotetradecyl. Examples of polycyclic rings are perhydroanthracyl, perhydrophenyathryl, perhydronaphthyl, perhydrofluorenyl, adamantyl, bicyclo[1.1.1]pentyl, bicyclo[4.2.2]decyl, bicyclo[2.2.2]octyl, bicyclo[3.3.2]decyl, bicyclo[4.3.2]undecyl, bicyclo[4.3.3]dodecyl, bicyclo[3.3.3]undecyl, bicyclo[4.3.1]decyl, bicyclo[4.2.1]nonyl, bicyclo[3.3.1]nonyl, bicyclo[3.2.1]octyl,

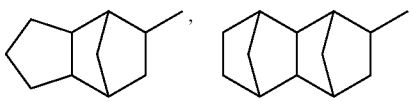

and the like. Also "spiro"-cycloalkyl compounds are intended to be covered by the definition $C_3$-$C_{14}$cycloalkyl in the present context, e.g. spiro[5.2]octyl, spiro[5.4]decyl, spiro[5.5]undecyl.

$C_3$-$C_6$cycloalkyl has one of the definitions as given above for $C_3$-$C_{14}$cycloalkyl up to the corresponding number of C-atoms.

$C_3$-$C_6$cycloalkyl which is interrupted by O, S, N($C_1$-$C_8$alkyl) or CO has the meanings given above for $C_3$-$C_6$cycloalkyl, wherein at least one $CH_2$-group of the cycloalkyl is exchanged by O, S, N($C_1$-$C_8$alkyl) or CO. Also "mixed" interruptions are meant to be covered by the definition, that is, the $C_2$-$C_{12}$alkyl is interrupted by one or more O and/or S and/or N($C_1$-$C_8$alkyl) an/or CO. Examples are structures like

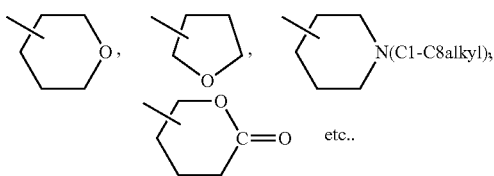

$C_2$-$C_8$alkenyl is mono or polyunsaturated, linear or branched and is for example $C_2$-$C_6$- or $C_2$-$C_4$alkenyl. Examples are allyl, methallyl, vinyl, 1,1-dimethylallyl, 1-butenyl, 3-butenyl, 2-butenyl, 1,3-pentadienyl, 5-hexenyl or 7-octenyl, especially allyl or vinyl. $C_2$-$C_8$alkenyl which is interrupted by O, S, N($C_1$-$C_8$alkyl) or CO is interrupted one or more times, e.g. 1-3, once or twice between a C—C-single bond by the defined atoms or groups.

$C_1$-$C_6$alkoxy is linear or branched and is for example $C_1$-$C_4$-alkoxy. Examples are methoxy, ethoxy, propoxy, isopropoxy, n-butyloxy, sec-butyloxy, iso-butyloxy, tert-butyloxy, pentyloxy or hexyloxy, in particular methoxy, ethoxy, propoxy, isopropoxy, n-butyloxy, sec-butyloxy, iso-butyloxy, tert-butyloxy, especially methoxy.

$C_1$-$C_6$alkylsulfanyl (=$C_1$-$C_6$alkylthio) is $C_1$-$C_6$alkyl, which at the "yl" moiety bears one-S-atom. $C_1$-$C_6$alkyl has the same meanings as given above for $C_1$-$C_6$alkyl up to the corresponding number of C-atoms. $C_1$-$C_6$alkylsulfanyl is linear or branched and is for example, methylsulfanyl, ethylsulfanyl, propylsulfanyl, isopropylsulfanyl, n-butylsulfanyl, sec-butylsulfanyl, isobutylsulfanyl, tert-butylsulfanyl, etc.

Phenyl-$C_1$-$C_4$alkyl is for example benzyl, phenylethyl, α-methylbenzyl, phenylbutyl, or α,α-dimethylbenzyl, especially benzyl.

Phenyl-$C_1$-$C_4$alkyl which is interrupted by O, S, N($C_1$-$C_8$alkyl) or CO is interrupted by the defined atoms or groups in the alkyl chain or between the alkyl chain and the phenyl ring, as for example

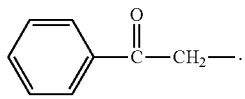

Halogen is fluorine, chlorine, bromine and iodine, especially fluorine, chlorine and bromine, preferably fluorine and chlorine Benzyl, phenyl or naphthyl which is substituted, is for example substituted 1-5 times, 1-4 times, three times, twice or once by one or more of the defined radicals, especially three times, once or twice, in particular once.

If $R_6$ and $R_7$, together with the N-atom to which they are attached, form a 5- or 6-membered ring via $C_2$-$C_5$alkylene, which $C_2$-$C_5$alkylene ring is uninterrupted or interrupted by one or more O, S, N($C_1$-$C_8$alkyl), NH or CO, saturated rings are formed, for example pyrrolidine, pyrazolidine, piperazine, piperidine or morpholine, in particular saturated rings such as for example piperidine or morpholine, preferably morpholine.

The terms "and/or" or "or/and" in the present context are meant to express that not only one of the defined alternatives (substituents) may be present, but also several of the defined alternatives (substituents) together, namely mixtures of different alternatives (substituents).

The term "at least" is meant to define one or more than one, for example one or two or three, preferably one or two.

Throughout this specification and the claims which follow, unless the context requires otherwise, the word "comprise", or variations such as "comprises" or "comprising", will be understood to imply the inclusion of a stated integer or step or group of integers or steps but not the exclusion of any other integer or step or group of integers or steps.

The term "(meth)acrylate" in the context of the present application is meant to refer to the acrylate as well as to the corresponding methacrylate.

The preferences indicated above for the compounds according to the present invention in the context of this invention are intended to refer to all categories of the claims, that is to the compositions, use, process claims as well.

It is to be understood that this invention is not limited to particular compounds, configurations, method steps, substrates, and materials disclosed herein as such compounds, configurations, method steps, substrates, and materials may vary somewhat. It is also to be understood that the terminology employed herein is used for the purpose of describing particular embodiments only and is not intended to be limiting since the scope of the present invention is limited only by the appended claims and equivalents thereof.

It must be noted that, as used in this specification and the appended claims, the singular forms "a", "an" and "the" include plural referents unless the context clearly dictates otherwise.

If nothing else is defined, any terms and scientific terminology used herein are intended to have the meanings commonly understood by those of skill in the art to which this invention pertains.

Oxime sulfonate compounds of formula (I) can generally be prepared by methods described in the literature or in the experimental part. For example, oxime sulfonates of the formula (I) can generally be prepared by reacting suitable free oximes of formula (IA) with sulfonic acid halides (IB):

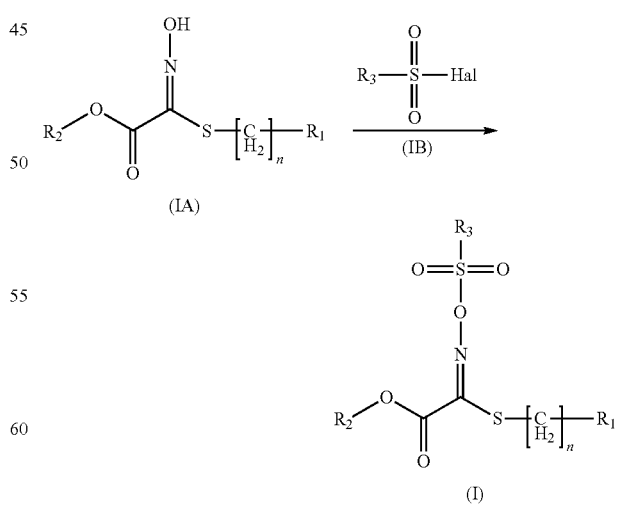

These reactions usually are carried out in pyridine as solvent and base or in an inert solvent such as for example toluene, tetrahydrofuran (THF) or dimethylformamide (DMF) in the presence of a base for example a tertiary amine, such as for example triethylamine and diisopropylethylamine, or by reaction of the salt of an oxime with the desired acid chloride. These methods are disclosed, for example, in EP48615. The sodium salts of oximes can be obtained, for example, by reacting the oxime in question with a sodium alkoxide in dimethylformamide. Such reactions are well known to those skilled in the art, and are generally carried out at temperatures in the range of −30 to +50° C., preferably −10 to 20° C.

Subject of the invention therefore also is a process for the reparation of compounds of the formula (I) as defined above by reacting a free oxime of the formula (IA)

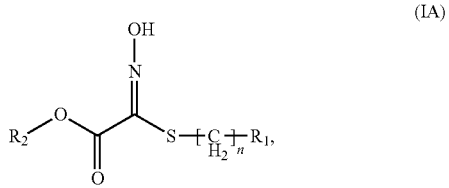

(IA)

wherein
n, $R_1$ and $R_2$ are as defined above,
with a sulfonic acid halide of the formula (IB)

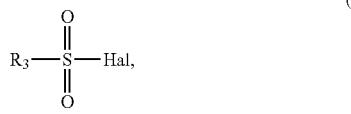

(IB)

wherein
$R_3$ is as defined above and Hal is a halogen, in particular Cl.

The oximes required as the starting materials can for example be obtained by a variety of methods described in the literature, for example, by reacting suitable oximidoyl halides, such as oximidoyl chloride or oximidoyl bromide with a thiol as described, for example, in *Synlett*, 937 (2001) or EP64091. These reactions are usually carried out in an inert solvent like toluene, dioxane, tetrahydrofuran (THF), diethyl ether, t-butyl methyl ether, dimethoxyethane, ethylacetate, dichloromethane, dimethylformamide (DMF), methanol or aqueous methanol in the presence of a base, for example, a tertiary amine, such as triethylamine, or metal hydroxide, such as NaOH, LiOH and KOH. JP1973015804A for example discloses another synthesis of oximidothio derivatives by condensation of a nitroalkane with thiol in the presence of non-acidic gamma-alumina.

The oximidoyl halides can for example be obtained by the oximination of glycine ethyl ester hydrochloride with sodium nitrite in aq. HCl solution as described, for example, in *J. Org. Chem.*, 48(3), 366 (1983).

Another synthesis of oximidoyl chloride is the oximination of 2-chloroacetoacetate with sodium nitrite and acid like HCl or $H_2SO_4$ in alcohol, as described for example in WO2012101245.

*Organic Syntheses, Coll. Vol.* 3, p. 191 (1955) discloses the preparation of chloroisonitrosoacetophenone from phenacyl chloride using n-butyl nitrite in the presence of HCl.

n is for example 1 or 2 in particular 2.
$R_1$ is $O(CO)R_4$, $COOR_5$ or $CONR_6R_7$.
Or $R_1$ is for example $O(CO)R_4$ or $CONR_6R_7$.
Or $R_1$ is for example $COOR_5$ or $CONR_6R_7$.
Or $R_1$ is for example $O(CO)R_4$ or $COOR_5$, in particular $O(CO)R_4$.

$R_2$ is $C_1$-$C_8$alkyl, $C_2$-$C_8$alkyl which is interrupted by one or more O, or $C_3$-$C_6$cycloalkyl, which is uninterrupted or is interrupted by one or more O; or $R_2$ is benzyl, which is unsubstituted or is substituted by one or more $C_1$-$C_6$alkyl, $C_1$-$C_4$haloalkyl, halogen, CN, $NO_2$, $C_1$-$C_6$alkylsulfanyl or $C_1$-$C_6$alkoxy.

Or $R_2$ is $C_1$-$C_8$alkyl, $C_2$-$C_8$alkyl which is interrupted by one or more O, or $C_3$-$C_6$cycloalkyl, benzyl, which is unsubstituted or is substituted by one or more $C_1$-$C_6$alkyl.

Or $R_2$ is $C_1$-$C_8$alkyl, $C_3$-$C_6$cycloalkyl, benzyl which is unsubstituted or is substituted by one or more $C_1$-$C_6$alkyl.

Or $R_2$ is $C_1$-$C_8$alkyl, $C_2$-$C_8$alkyl which is interrupted by one or more O, benzyl, which is unsubstituted or is substituted by one or more $C_1$-$C_6$alkyl.

Or $R_2$ is $C_1$-$C_8$alkyl, $C_2$-$C_8$alkyl which is interrupted by one or more O or benzyl.

Or $R_2$ is $C_1$-$C_8$alkyl, $C_3$-$C_6$cycloalkyl or benzyl.
In particular $R_2$ is $C_1$-$C_8$alkyl or benzyl.

$R_3$ is $C_1$-$C_8$alkyl, $C_3$-$C_6$cycloalkyl, $C_1$-$C_8$haloalkyl, $C_2$-$C_8$alkenyl, benzyl, phenyl or naphthyl, which benzyl, phenyl or naphthyl is unsubstituted or substituted by one or more $C_1$-$C_6$alkyl, $C_1$-$C_4$haloalkyl, halogen, CN, $NO_2$, $C_1$-$C_6$alkylsulfanyl, $C_1$-$C_6$alkoxy, phenyl or $COO(C_1$-$C_6$alkyl).

Or $R_3$ is $C_1$-$C_8$alkyl, $C_3$-$C_6$cycloalkyl, $C_1$-$C_8$haloalkyl, benzyl or phenyl, which benzyl or phenyl is unsubstituted or substituted by one or more $C_1$-$C_6$alkyl, $C_1$-$C_4$haloalkyl, halogen, CN, $NO_2$, $C_1$-$C_6$alkylsulfanyl, $C_1$-$C_6$alkoxy, phenyl or $COO(C_1$-$C_6$alkyl).

Or $R_3$ is $C_1$-$C_8$alkyl, benzyl or phenyl, which benzyl or phenyl is unsubstituted or substituted by one or more $C_1$-$C_6$alkyl, $C_1$-$C_4$haloalkyl, halogen, CN, $NO_2$, $C_1$-$C_6$alkylsulfanyl, $C_1$-$C_6$alkoxy or phenyl.

Or $R_3$ is $C_1$-$C_8$alkyl, benzyl or phenyl, which benzyl or phenyl is unsubstituted or substituted by one or more $C_1$-$C_6$alkyl or $C_1$-$C_4$haloalkyl.

Or $R_3$ is $C_1$-$C_8$alkyl, benzyl or phenyl, which benzyl or phenyl is unsubstituted or substituted by one or more $C_1$-$C_6$alkyl.

Preferably $R_3$ is benzyl, phenyl or phenyl substituted by $C_1$-$C_6$alkyl, in particular by methyl.

$R_4$ is $C_1$-$C_8$alkyl, $C_3$-$C_6$cycloalkyl, $C_1$-$C_8$haloalkyl, $C_2$-$C_8$alkenyl, benzyl, phenyl or naphthyl, which benzyl, phenyl or naphthyl are unsubstituted or substituted by one or more $C_1$-$C_6$alkyl, $C_1$-$C_4$haloalkyl, halogen, CN, $NO_2$, $C_1$-$C_6$alkylsulfanyl, phenylsulfanyl, $C_1$-$C_6$alkoxy, phenoxy, phenyl or $COO(C_1$-$C_6$alkyl);

Or $R_4$ is $C_1$-$C_8$alkyl, $C_3$-$C_6$cycloalkyl, $C_1$-$C_8$haloalkyl, benzyl or phenyl, which benzyl or phenyl is unsubstituted or substituted by one or more $C_1$-$C_6$alkyl, $C_1$-$C_4$haloalkyl, halogen, CN, $NO_2$, $C_1$-$C_6$alkylsulfanyl, $C_1$-$C_6$alkoxy, phenyl or $COO(C_1$-$C_6$alkyl).

Or $R_4$ is $C_1$-$C_8$alkyl, benzyl or phenyl, which benzyl or phenyl is unsubstituted or substituted by one or more $C_1$-$C_6$alkyl, $C_1$-$C_4$haloalkyl, halogen, CN, $NO_2$, $C_1$-$C_6$alkylsulfanyl, $C_1$-$C_6$alkoxy or phenyl.

Or $R_4$ is $C_1$-$C_8$alkyl, benzyl or phenyl, which benzyl or phenyl is unsubstituted or substituted by one or more $C_1$-$C_6$alkyl or $C_1$-$C_4$haloalkyl.

Or $R_4$ is $C_1$-$C_8$alkyl, benzyl or phenyl, which benzyl or phenyl is unsubstituted or substituted by one or more $C_1$-$C_6$alkyl.

Preferably $R_4$ is benzyl, phenyl or phenyl substituted by $C_1$-$C_6$alkyl, in particular by methyl.

$R_5$ is $C_3$-$C_{20}$alkyl, $C_3$-$C_{14}$cycloalkyl, $C_2$-$C_8$alkenyl, $C_1$-$C_{12}$alkyl substituted by one or more radicals selected from the group consisting of halogen, CN, phenylsulfanyl, phenoxy, $N(C_1$-$C_6$alkyl$)_2$, $N($phenyl$)_2$, phthalimido, phenyl and phenyl substituted by one or more $C_1$-$C_{12}$alkyl, $C_1$-$C_4$haloalkyl, halogen, CN, $NO_2$, $C_1$-$C_6$alkylsulfanyl phenylsulfanyl, $C_1$-$C_6$alkoxy, phenoxy, $N(C_1$-$C_6$alkyl$)_2$ or $N($phenyl$)_2$;

or $R_5$ is $C_2$-$C_{12}$alkyl or $C_3$-$C_6$cycloalkyl, each of which is interrupted by one or more O or S; or $R_5$ is phenyl or naphthyl, which phenyl or naphthyl are unsubstituted or substituted by one or more $C_1$-$C_6$alkyl, $C_1$-$C_4$haloalkyl, halogen, CN, $NO_2$, $C_1$-$C_6$alkylsulfanyl, $C_1$-$C_6$alkoxy, phenyl or COO($C_1$-$C_6$alkyl).

Or $R_5$ is for example $C_3$-$C_{20}$alkyl, $C_3$-$C_{14}$cycloalkyl, $C_1$-$C_{12}$alkyl substituted by one or more radicals selected from the group consisting of halogen, CN, phenylsulfanyl, phenoxy, $N(C_1$-$C_6$alkyl$)_2$, $N($phenyl$)_2$, phthalimido and phenyl;

or $R_5$ is $C_2$-$C_{12}$alkyl which is interrupted by one or more O or S;

or $R_5$ is phenyl.

Or $R_5$ is for example $C_3$-$C_{18}$alkyl, $C_3$-$C_{12}$cycloalkyl, phenyl, $C_1$-$C_{12}$alkyl substituted by one or more phenoxy, phthalimido or phenyl; or $R_5$ is $C_2$-$C_{12}$alkyl which is interrupted by one or more O or S.

Or $R_5$ is for example $C_3$-$C_{18}$alkyl, $C_3$-$C_{12}$cycloalkyl, phenyl, $C_1$-$C_{12}$alkyl substituted by one or more phenoxy, phthalimido or phenyl; or $R_5$ is $C_2$-$C_{12}$alkyl which is interrupted by one or more O.

Preferably $R_5$ is $C_3$-$C_{15}$alkyl, $C_3$-$C_{12}$cycloalkyl, $C_2$-$C_{12}$alkyl which is interrupted by one or more O or $R_5$ is $C_1$-$C_6$alkyl substituted by phenyl, phenoxy or phthalimido.

$R_6$ and $R_7$ for example each independently of one another are hydrogen, $C_1$-$C_{12}$alkyl, $C_1$-$C_4$haloalkyl, phenyl-$C_1$-$C_4$alkyl, $C_2$-$C_8$alkenyl or $C_3$-$C_6$cycloalkyl, or $R_6$ and $R_7$ independently of each other are phenyl or naphthyl, which phenyl or naphthyl is unsubstituted or is substituted by one or more $C_1$-$C_6$alkyl, $C_1$-$C_4$haloalkyl, halogen, CN, $NO_2$, $C_1$-$C_6$alkylsulfanyl, $C_1$-$C_6$alkoxy, phenyl or COO($C_1$-$C_6$alkyl); or $R_6$ and $R_7$, together with the N-atom to which they are attached, form a 5- or 6-membered ring via $C_2$-$C_8$alkylene, which $C_2$-$C_8$alkylene ring is uninterrupted or interrupted by one or more O, S, $N(C_1$-$C_8$alkyl), NH, or CO.

Or $R_6$ and $R_7$ for example each independently of one another are hydrogen, $C_1$-$C_{12}$alkyl, $C_1$-$C_4$haloalkyl, phenyl-$C_1$-$C_4$alkyl, $C_2$-$C_8$alkenyl or $C_3$-$C_6$cycloalkyl, or $R_6$ and $R_7$ independently of each other are phenyl, which phenyl is unsubstituted or is substituted by one or more $C_1$-$C_6$alkyl; or $R_6$ and $R_7$, together with the N-atom to which they are attached, form a 5- or 6-membered ring via $C_2$-$C_5$alkylene, which $C_2$-$C_5$alkylene ring is uninterrupted or interrupted by one or more O.

Or $R_6$ and $R_7$ for example each independently of one another are hydrogen, $C_1$-$C_{12}$alkyl, phenyl-$C_1$-$C_4$alkyl, $C_3$-$C_6$cycloalkyl or phenyl which is unsubstituted or is substituted by one or more $C_1$-$C_6$alkyl; or $R_6$ and $R_7$, together with the N-atom to which they are attached, form a morpholino ring.

Or $R_6$ and $R_7$ for example each independently of one another are hydrogen, $C_1$-$C_6$alkyl or phenyl which is unsubstituted or is substituted by one or more $C_1$-$C_6$alkyl.

Or $R_6$ and $R_7$ for example each independently of one another are hydrogen, $C_1$-$C_{12}$alkyl or phenyl.

Preferably $R_6$ and $R_7$ are hydrogen or phenyl.

Preferred are compounds of the formula (I) as defined above, wherein
$R_1$ is $O(CO)R_4$, $COOR_5$ or $CONR_6R_7$;
n is 1 or 2;
$R_2$ is $C_1$-$C_8$alkyl, $C_3$-$C_6$cycloalkyl, benzyl, which is unsubstituted or is substituted by one or more $C_1$-$C_6$alkyl;
$R_3$ is $C_1$-$C_8$alkyl, $C_3$-$C_6$cycloalkyl, $C_1$-$C_8$haloalkyl or $C_2$-$C_8$alkenyl;
or $R_3$ is benzyl or phenyl, which benzyl or phenyl is unsubstituted or substituted by one or more $C_1$-$C_6$alkyl;
$R_4$ is $C_1$-$C_8$alkyl, $C_3$-$C_6$cycloalkyl, $C_1$-$C_8$haloalkyl or $C_2$-$C_8$alkenyl;
or $R_4$ is benzyl or phenyl, which benzyl or phenyl is unsubstituted or substituted by one or more $C_1$-$C_6$alkyl;
$R_5$ is $C_3$-$C_{18}$alkyl, $C_3$-$C_{12}$cycloalkyl;
or $R_5$ is $C_1$-$C_6$alkyl substituted by one or more phenylsulfanyl, phenoxy, $N(C_1$-$C_6$alkyl$)_2$, $N($phenyl$)_2$, phthalimido, phenyl or phenyl substituted by one or more $C_1$-$C_{12}$alkyl;
or $R_5$ is $C_2$-$C_{12}$alkyl which is interrupted by one or more O;
or $R_5$ is phenyl;
$R_6$ and $R_7$ each independently of one another are hydrogen, $C_1$-$C_{12}$alkyl, $C_3$-$C_6$cycloalkyl,
or $R_6$ and $R_7$ independently of each other are phenyl, which phenyl is unsubstituted or is substituted by one or more $C_1$-$C_6$alkyl.

Further interesting are compounds of the formula (I) as defined above, wherein
$R_1$ is $O(CO)R_4$, $COOR_5$ or $CONR_6R_7$;
n is 1 or 2;
$R_2$ is $C_1$-$C_8$alkyl or benzyl, which is unsubstituted or is substituted by one or more $C_1$-$C_6$alkyl;
$R_3$ is $C_1$-$C_8$alkyl, $C_3$-$C_6$cycloalkyl, benzyl or phenyl which phenyl is unsubstituted or substituted by one or more $C_1$-$C_6$alkyl;
$R_4$ is $C_1$-$C_8$alkyl, $C_3$-$C_6$cycloalkyl, benzyl or phenyl which phenyl is unsubstituted or substituted by one or more $C_1$-$C_6$alkyl;
$R_5$ is $C_3$-$C_{18}$alkyl, $C_3$-$C_{12}$cycloalkyl;
or $R_5$ is $C_1$-$C_6$alkyl substituted by one or more phenylsulfanyl, phenoxy, $N(C_1$-$C_6$alkyl$)_2$, $N($phenyl$)_2$, phthalimido, phenyl or phenyl substituted by one or more $C_1$-$C_{12}$alkyl;
or $R_5$ is $C_2$-$C_{12}$alkyl which is interrupted by one or more O;
$R_6$ and $R_7$ each independently of one another are hydrogen, $C_1$-$C_{12}$alkyl, $C_3$-$C_6$cycloalkyl,
or $R_6$ and $R_7$ independently of each other are phenyl.

Interesting are compounds of the formula I as described above, wherein
$R_1$ is $O(CO)R_4$, $COOR_5$ or $CONR_6R_7$;
n is 1 or 2;
$R_2$ is $C_1$-$C_4$alkyl or benzyl;
$R_3$ is benzyl, phenyl or phenyl substituted by one or more $C_1$-$C_6$alkyl;
$R_4$ is benzyl, phenyl or phenyl substituted by one or more $C_1$-$C_6$alkyl;
$R_5$ is $C_3$-$C_{18}$alkyl or $C_3$-$C_{12}$cycloalkyl,
or $R_5$ is $C_2$-$C_{12}$alkyl which is interrupted by one or more O,
or $R_5$ is $C_1$-$C_6$alkyl substituted by phenylsulfanyl, phenoxy, $N(C_1$-$C_6$alkyl$)_2$, $N($phenyl$)_2$, phthalimido, phenyl or phenyl substituted by one or more $C_1$-$C_{12}$alkyl;
$R_6$ and $R_7$ each independently of one another are hydrogen, $C_1$-$C_6$alkyl or phenyl, or together with the N-atom to which they are attached for a morpholino ring.

Emphasis has to be laid on compounds of the formula I as described above, wherein
$R_1$ is $O(CO)R_4$, $COOR_5$ or $CONR_6R_7$;
n is 1 or 2
$R_2$ is methyl, ethyl or benzyl $R_3$ is benzyl, phenyl or phenyl substituted by $C_1$-$C_6$alkyl, in particular by methyl;

$R_4$ is benzyl, phenyl or phenyl substituted by one or more $C_1$-$C_6$alkyl, in particular by one or more methyl;

$R_5$ is $C_3$-$C_{18}$alkyl or $C_3$-$C_{12}$cycloalkyl, or $R_5$ is $C_2$-$C_{12}$alkyl which is interrupted by one or more O, or $R_5$ is $C_1$-$C_6$alkyl substituted by phenyl, phenoxy or phthalimido;

$R_6$ and $R_7$ each independently of one another are hydrogen or phenyl

In particular interesting are the compounds OS1-OS18 as shown in the examples below.

The compounds of formula (I) as defined above can be used in principle to polymerize all types of ethylenically unsaturated compounds.

In particular the compounds of the formula (I) can be used as thermal radical initiators. Accordingly subject of the invention is a polymerizable composition comprising, (a) a monomeric, oligomeric or polymeric compound having at least one ethylenically unsaturated double bond; and (b) at least one oxime sulfonate compound of formula I as defined above.

Suitable ethylenically unsaturated compounds (a) are monomers or oligomers that can be polymerized in a manner known per se using the methods of free-radical polymerization.

The term "(meth)acrylate" in the context of the present application is meant to refer to the acrylate as well as to the corresponding methacrylate.

Preferably, compound (a) is selected from esters of α,β-ethylenically unsaturated monocarboxylic and dicarboxylic acids with $C_1$-$C_{20}$alkanols, vinylaromatics, esters of vinyl alcohol with $C_1$-$C_{30}$monocarboxylic acids, ethylenically unsaturated nitriles, vinyl halides, vinylidene halides, monoethylenically unsaturated carboxylic and sulfonic acids, esters of α,β-ethylenically unsaturated monocarboxylic and dicarboxylic acids with $C_2$-$C_{30}$ alkanediols, amides of α,β-ethylenically unsaturated monocarboxylic and dicarboxylic acids with $C_2$-$C_{30}$amino alcohols which contain a primary or secondary amino group, primary amides of α,β-ethylenically unsaturated monocarboxylic acids and their N-alkyl and N,N-dialkyl derivatives, N-vinyllactams, open-chain N-vinylamide compounds, esters of allyl alcohol with $C_1$-$C_{30}$monocarboxylic acids, esters of α,β-ethylenically unsaturated monocarboxylic and dicarboxylic acids with amino alcohols, amides of α,β-ethylenically unsaturated monocarboxylic and dicarboxylic acids with diamines which contain at least one primary or secondary amino group, N,N-diallylamines, N,N-diallyl-N-alkylamines, vinyl- and allyl-substituted nitrogen heterocycles, vinyl ethers, $C_2$-$C_8$monoolefins, nonaromatic hydrocarbons having at least two conjugated double bonds, polyether(meth) acrylates, heterocyclyl-($C_2$-$C_4$-alkyl) (meth)acrylates, silyl group-containing (meth)acrylates, and mixtures thereof.

Suitable ethylenically unsaturated carboxylic acids and sulfonic acids or their derivatives are acrylic acid, methacrylic acid, ethacrylic acid, α-chloroacrylic acid, crotonic acid, maleic acid, maleic anhydride, itaconic acid, citraconic acid, mesaconic acid, glutaconic acid, aconitic acid, fumaric acid, the monoesters of monoethylenically unsaturated dicarboxylic acids having 4 to 10, preferably 4 to 6, C atoms, e.g., monomethyl maleate, vinylsulfonic acid, allylsulfonic acid, sulfoethyl acrylate, sulfoethyl methacrylate, sulfopropyl acrylate, sulfopropyl methacrylate, 2-hydroxy-3-acryloyloxypropylsulfonic acid, 2-hydroxy-3-methacryloyloxypropylsulfonic acid, styrenesulfonic acid, and 2-acrylamido-2-methylpropanesulfonic acid.

Suitable derivatives of ethylenically unsaturated carboxylic acids and sulfonic acids are their salts. Suitable salts of acrylic acid or methacrylic acid are, for example, ($C_1$-$C_4$-alkyl)$_4$ammonium or ($C_1$-$C_4$-alkyl)$_3$NH salts, e. g. the tetramethylammonium, tetraethylammonium, trimethylammonium or triethylammonium salts, the trimethyl-2-hydroxyethylammonium or triethyl-2-hydroxyethylammonium salts, the dimethyl-2-hydroxyethylammonium or diethyl-2-hydroxyethylammonium salts.

Suitable esters of α,β-ethylenically unsaturated monocarboxylic and dicarboxylic acids with $C_1$-$C_{20}$alkanols are methyl (meth)acrylate, methyl ethacrylate, ethyl (meth)acrylate, ethyl ethacrylate, n-propyl (meth)acrylate, isopropyl (meth)acrylate, n-butyl (meth)acrylate, sec-butyl (meth) acrylate, tert-butyl (meth)acrylate, tert-butyl ethacrylate, n-hexyl (meth)acrylate, n-heptyl (meth)acrylate, n-octyl (meth)acrylate, 1,1,3,3-tetramethylbutyl (meth)acrylate, ethylhexyl (meth)acrylate, n-nonyl (meth)acrylate, n-decyl (meth)acrylate, n-undecyl (meth)acrylate, tridecyl (meth) acrylate, myristyl (meth)acrylate, pentadecyl (meth)acrylate, palmityl (meth)acrylate, heptadecyl (meth)acrylate, nonadecyl (meth)acrylate, arachidyl (meth)acrylate, behenyl (meth)acrylate, lignoceryl (meth)acrylate, cerotinyl (meth) acrylate, melissinyl (meth)acrylate, palmitoleyl (meth)acrylate, oleyl(meth)acrylate, linolyl (meth)acrylate, linolenyl (meth)acrylate, stearyl (meth)acrylate, lauryl (meth)acrylate, and mixtures thereof.

Preferred vinylaromatics are styrene, 2-methylstyrene, 4-methylstyrene, 2-(n-butyl)styrene, 4-(n-butyl)styrene, 4-(n-decyl)styrene, and, with particular preference, styrene.

Suitable esters of vinyl alcohol with $C_1$-$C_{30}$monocarboxylic acids are, for example, vinyl formate, vinyl acetate, vinyl propionate, vinyl butyrate, vinyl laurate, vinyl stearate, vinyl propionate, versatic acid vinyl esters, and mixtures thereof.

Suitable ethylenically unsaturated nitriles are acrylonitrile, methacrylonitrile, and mixtures thereof.

Suitable vinyl halides and vinylidene halides are vinyl chloride, vinylidene chloride, vinyl fluoride, vinylidene fluoride, and mixtures thereof.

Suitable esters of α,β-ethylenically unsaturated monocarboxylic and dicarboxylic acids with $C_2$-$C_{30}$alkanediols are, for example, 2-hydroxyethyl acrylate, 2-hydroxyethyl methacrylate, 2-hydroxyethyl ethacrylate, 2-hydroxypropyl acrylate, 2-hydroxypropyl methacrylate, 3-hydroxypropyl acrylate, 3-hydroxypropyl methacrylate, 3-hydroxybutyl acrylate, 3-hydroxybutyl methacrylate, 4-hydroxybutyl acrylate, 4-hydroxybutyl methacrylate, 6-hydroxyhexyl acrylate, 6-hydroxyhexyl methacrylate, 3-hydroxy-2-ethylhexyl acrylate, 3-hydroxy-2-ethylhexyl methacrylate, etc.

Suitable primary amides of α,β-ethylenically unsaturated monocarboxylic acids and their N-alkyl and N,N-dialkyl derivatives are acrylamide, methacrylamide, N-methyl (meth)acrylamide, N-ethyl(meth)acrylamide, N-propyl (meth)acrylamide, N-(n-butyl)(meth)acrylamide, N-(tert-butyl)(meth)acrylamide, N-(n-octyl)(meth)acrylamide, N-(1,1,3,3-tetramethylbutyl)(meth)acrylamide, N-ethylhexyl(meth)acrylamide, N-(n-nonyl)(meth)acrylamide, N-(n-decyl)(meth)acrylamide, N-(n-undecyl)(meth)acrylamide, N,N-dimethyl(meth)acrylamide, N,N-diethyl(meth) acrylamide, morpholinyl(meth)acrylamide, etc.

Suitable N-vinyllactams and their derivatives are, for example, N-vinylpyrrolidone, N-vinylpiperidone, N-vinylcaprolactam, etc.

Suitable open-chain N-vinylamide compounds are, for example, N-vinylformamide, N-vinyl-N-methylformamide, N-vinylacetamide, N-vinylpropionamide, N-vinylbutyramide, etc.

Suitable esters of α,β-ethylenically unsaturated monocarboxylic and dicarboxylic acids with amino alcohols are N,N-dimethylaminomethyl (meth)acrylate, N,N-dimethylaminoethyl (meth)acrylate, N,N-diethylaminoethylacrylate, N,N-dimethylaminopropyl (meth)acrylate, N,N-diethylaminopropyl (meth)acrylate and N,N-dimethylaminocyclohexyl (meth)acrylate.

Suitable amides of α,β-ethylenically unsaturated monocarboxylic and dicarboxylic acids with diamines which contain at least one primary or secondary amino group are N-[2-(dimethylamino)ethyl]acrylamide, N-[2-(dimethylamino)ethyl]methacrylamide, N-[3-(dimethylamino)propyl]acrylamide, N-[3-(dimethylamino)propyl]methacrylamide, N-[4-(dimethylamino)butyl]acrylamide, N-[4-(dimethylamino)-butyl]methacrylamide, N-[2-(diethylamino)ethyl]acrylamide, N-[4-(dimethylamino)cyclohexyl]acrylamide, N-[4-(dimethylamino)cyclohexyl]methacrylamide, etc.

Suitable monomers (a) are, furthermore, N,N-diallylamines and N,N-diallyl-N-alkylamines and their acid addition salts and quaternization products. Alkyl here is preferably $C_1$-$C_{24}$ alkyl. Preference is given to N,N-diallyl-N-methylamine and to N,N-diallyl-N,N-dimethylammonium compounds, such as the chlorides and bromides, for example.

Further suitable monomers (a) are vinyl- and allyl-substituted nitrogen heterocycles, such as N-vinylimidazole, N-vinyl-2-methylimidazole, and vinyl- and allyl-substituted heteroaromatic compounds, such as 2- and 4-vinylpyridine, 2- and 4-allylpyridine, and the salts thereof.

Suitable $C_2$-$C_8$ monoolefins and nonaromatic hydrocarbons having at least two conjugated double bonds are, for example, ethylene, propylene, isobutylene, isoprene, butadiene, etc.

Examples of silyl group-containing (meth)acrylates are silyloxy-$C_2$-$C_4$-(meth)alkyl acrylates, e.g. 2-trimethylsilyloxyethyl acrylate or methacrylate (TMS-HEA, TMS-HEMA). Examples of $(C_1$-$C_4$-alkyl$)_3$-silyl-$C_2$-$C_4$ alkyl (meth)acrylates are 2-trimethylsilylethyl acrylate or methacrylate and 3-trimethylsilyl-n-propyl acrylate or methacrylate.

In particular, compound (a) is selected from acrylic acid, methacrylic acid, maleic anhydride, acrylic acid derivatives, styrene, vinyl acetate, vinyl halides and vinylidene halides, acrolein, vinylpyrrolidone, vinylimidazole, alkenes, conjugated dienes and mixtures thereof.

Examples of heterocycyl-($C_2$-$C_4$-alkyl) (meth)acrylates are 2-(N-morpholinyl, 2-pyridyl, 1-imidazolyl, 2-oxo-1-pyrrolidinyl, 4-methylpiperidin-1-yl or 2-oxoimidazolidin-1-yl) ethyl acrylate or methacrylate.

Suitable polyether (meth)acrylates (a) are compounds of the general formula (A)

$$H_2C=\underset{Rb}{\underset{|}{C}}-\underset{O}{\underset{\|}{C}}-Y-(CH_2CH_2O)_k-(CH_2CH(CH_3)O)_l-Ra, \quad (A)$$

in which the sequence of the alkylene oxide units is arbitrary,
k and l independently of one another are an integer from 0 to 100, the sum of k and l being at least 3, Ra is hydrogen, $C_1$-$C_{30}$ alkyl, $C_5$-$C_8$ cycloalkyl or $C_6$-$C_{14}$ aryl,
Rb is hydrogen or $C_1$-$C_8$ alkyl,
Y is O or $NR^c$, where
$R^c$ is hydrogen, $C_1$-$C_{30}$ alkyl or $C_5$-$C_5$ cycloalkyl.

Preferably k is an integer from 3 to 50, more particularly 4 to 25. Preferably I is an integer from 3 to 50, more particularly 4 to 25.

Preferably Ra in the formula (A) is hydrogen, methyl, ethyl, n-propyl, isopropyl, n-butyl, sec-butyl, n-pentyl, n-hexyl, octyl, 2-ethylhexyl, decyl, lauryl, palmityl or stearyl.

Preferably Rb is hydrogen, methyl, ethyl, n-propyl, isopropyl, n-butyl, sec-butyl, tert-butyl, n-pentyl or n-hexyl, more particularly hydrogen, methyl or ethyl. With particular preference Rb is hydrogen or methyl.

Preferably Y in the formula (A) is O.

The polymerizable composition according to the invention preferably comprises the component (a) in an amount of from 0.01 to 50% by weight, more preferably 0.1 to 40% by weight, in particular 0.5 to 30% by weight, based on the total weight of the composition.

The composition according to the invention preferably comprises at least one photoinitiator (c) as further component.

The composition according to the invention preferably comprises at least one binder polymer (d) as further component.

The composition according to the invention preferably comprises at least one further component (e) selected from
(e1) pigments,
(e2) dyes,
(e3) fillers,
(e4) dispersants,
(e5) sensitizers,
(e6) thermosetting compounds, being different from compounds of the formula (I) and binder polymers (d),
mixtures thereof.

The composition according to the invention preferably comprises at least one additive (f) selected from solvents, reinforcing materials, flow control assistants, UV stabilizers, heat stabilizers, weatherability improvers, rheology modifiers, flame retardants, antioxidants, discoloration inhibitors, biocides, antistatic agents, plasticizers, lubricants, slip additives, wetting agents, film-forming assistants, adhesion promoters, corrosion inhibitors, antifreeze agents, defoamers, mold release agents, etc., and mixtures thereof.

Suitable photoinitiators (c) are described in the following with regard to a polymerizable composition comprising an alkaline developable resin (d). This disclosure is incorporated here for all polymerizable compositions of the invention.

Photoinitiators (c) are preferably used in an amount of from 0.001% to 15% by weight, more preferably from 0.01 to 10% by weight, based on the total weight of the polymerizable composition according to the invention.

Suitable binder polymers (d) are e.g. physically drying polymer compositions, self-crosslinking polymer compositions, UV-curable polymer compositions, thermosetting polymer compositions, polymer compositions crosslinkable by addition of a crosslinker (2-component dispersions), or dual-cure systems. Suitable thermosetting polymer compositions are described in the following as component (e6).

In a preferred embodiment the binder polymer component (d) comprises at least one alkaline developable resin. Suitable alkaline developable resins (d) are described in detail in the following.

Binder polymers (d) are preferably used in an amount of from 0.5% to 98% by weight, more preferably from 1 to 95% by weight, in particular from 2 to 90% by weight, based on the total weight of the polymerizable composition according to the invention.

Suitable colorants, i.e. pigments (e1) and dyes (e2) are described in the following with regard to a polymerizable composition comprising an alkaline developable resin (d). This disclosure is incorporated here for all polymerizable compositions of the invention.

Suitable fillers (e3) are organic and inorganic fillers, examples being aluminosilicates, such as feldspars, silicates, such as kaolin, talc, mica, magnesite, alkaline earth metal carbonates, such as calcium carbonate, in the form of calcite or chalk, for example, magnesium carbonate, dolomite, alkaline earth metal sulfates, such as calcium sulfate, silicon dioxide, etc. Suitable organic fillers are, for example, textile fibers, cellulose fibers, polyethylene fibers or wood flour. In coating materials, of course, finely divided fillers are preferred. The fillers may be used as individual components. In practice, mixtures of fillers have also proven particularly appropriate, examples being calcium carbonate/kaolin, calcium carbonate/talc. For further details refer to Römpp-Lexikon, Lacke and Druckfarben, Georg Thieme Verlag, 1998, pages 250 ff., "fillers".

Fillers (e3) are preferably used in an amount of from 0% to 95% by weight, more preferably from 0.5 to 90% by weight, in particular from 1 to 80% by weight, and especially 4% to 75% by weight, based on the total weight of the polymerizable composition according to the invention.

The term dispersant (=component e4) as used herein is understood in a broad sense. Dispersant are dispersing agents (including polymeric dispersants), surfactants, texture improving agents, and the like. Suitable dispersants (e4) are described in the following with regard to a polymerizable composition comprising an alkaline developable resin (d). This disclosure is incorporated here for all polymerizable compositions of the invention.

Where the polymerizable compositions of the invention comprise at least one dispersant (e4), it is preferably used in an amount of 0.01% to 50% by weight, preferably 0.1% to 30% by weight, based on the total weight of the polymerizable composition.

Suitable (photo)sensitizers (e5) are described in the following with regard to a polymerizable composition comprising an alkaline developable resin (d). This disclosure is incorporated here for all polymerizable compositions of the invention.

Sensitizers (e5) are preferably used in an amount of from 0.001% to 15% by weight, more preferably from 0.01 to 10% by weight, based on the total weight of the polymerizable composition according to the invention.

Suitable thermosetting compounds (e6) have at least one group selected from an epoxy group, oxetane group and vinyl ether group.

Suitable compounds (e6) are:
compounds comprising an oxygen- or sulphur-containing saturated heterocycle,
ethylenically unsaturated compounds which are polymerisable by a cationic mechanism,
prepolymers of phenol-formaldehyde resins, acrylic resins, alkyd resins or polyester resins containing heat curable functional groups,
mixtures of heat curable compounds and compounds polymerisable by a different mechanism, e.g. free radicals or UV irradiation,
mixtures thereof.

Compounds (e6) which comprise an oxygen- or sulphur-containing saturated heterocycle preferably comprise at least one heterocycle having 3, 4, 5 or 6 ring members. Preferred compounds (e6) which comprise an oxygen- or sulphur-containing saturated heterocycle are selected from compounds containing at least one epoxy group, oxetanes, oxolanes, cyclic acetals, cyclic lactones, thiiranes, thietanes and mixtures thereof.

Suitable compounds (e6) containing one epoxy group are ethylene oxide, propylene oxide, styrene oxide, phenyl glycidyl ether, butyl glycidyl ether, etc.

In a preferred embodiment of the invention, compound (e6) is selected from epoxy resins. The term "epoxy resin" as utilized in the description of the curable compositions of the present invention, is understood in a broad sense and includes any monomeric, dimeric, oligomeric or polymeric epoxy material containing a plurality (2, 3, 4, 5, 6 or more than 6) of epoxy groups. The term "epoxy resins" also encompasses prepolymers which comprise two or more epoxide groups, wherein some of the epoxide groups (oxiran rings) may also have been opened to a hydroxyl group. The term also identifies part-cured epoxy resins, i.e., epoxy resins which have been crosslinked by means of suitable hardeners. If component (a) is a part cured epoxy resin, it still contains heat curable epoxy groups that are still capable of undergoing cationic polymerization. The term "epoxy resins" also encompasses modified epoxy resins, such as esterified or etherified epoxy resins, obtainable for example by reaction with carboxylic acids or alcohols. Again, modified epoxy resins that are employed in a composition according to the invention still contain heat curable epoxy groups that are still capable of undergoing cationic polymerization. A complete definition of the term "epoxy resins" is found for example in Ullmann's Encyclopedia of Industrial Chemistry, 5th edition, on CD-ROM, 1997, Wiley-VCH, in the "Epoxy Resins" section.

The majority of commercial epoxy resins are prepared by coupling epichlorohydrin onto compounds which possess at least two reactive hydrogen atoms, such as polyphenols, monoamines and diamines, aminophenols, heterocyclic imides and amides, aliphatic diols or polyols or dimeric fatty acids. Epoxy resins derived from epichlorohydrin are referred to as glycidyl-based resins.

The majority of epoxy resins available commercially at the present time derive from the diglycidyl ether of bisphenol A (DGEBA resins) and possess the general formula

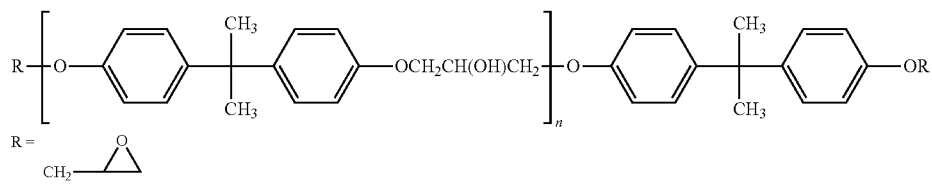

in which n stands for 0 to approximately 40.

Other important epoxy resins are phenol-based and cresol-based epoxy novolaks, examples being epoxy resins which derive from the diglycidyl ether of bisphenol F. Novolaks are prepared by the acid-catalyzed condensation of formaldehyde and phenol or cresol. The epoxidation of the novolaks leads to epoxy novolaks.

Other classes of glycidyl-based epoxy resins derive from glycidyl ethers of aliphatic diols, such as butane-1,4-diol, hexane-1,6-diol, pentaerythritol or hydrogenated bispheno) A; aromatic glycidylamines, an example being the triglycidyl adduct of p-aminophenol or the tetraglycidylamine of methylenedianilide; heterocyclic glycidylimides and amides, e.g., triglycidyl isocyanurate; and glycidyl esters, such as the diglycidyl ester of dimeric linoleic acid, for example.

The epoxy resins (e6) may also derive from other epoxides (non-glycidyl ether epoxy resins). Examples are the diepoxides of cycloaliphatic dienes, such as 3,4-epoxycyclohexylmethyl 3,4-epoxycyclohexanecarboxylate and 4-epoxyethyl-1,2-epoxycyclohexane.

Suitable oxetanes (e6) are trimethylene oxide, 3,3-dimethyloxetane, 3,3-di(chloromethyl) oxetane, etc.

Suitable oxolanes (e6) are tetrahydrofuran, 2,3-dimethyl-tetrahydrofuran, etc.

Suitable cyclic acetals (e6) are trioxan, 1,3-dioxolane, 1,3,6-trioxacyclooctane, etc.

Suitable cyclic lactones (e6) are β-propiolactone, ε-caprolactone, the alkyl derivatives of β-propiolactone and ε-caprolactone, etc.

Suitable thiiranes (e6) are ethylene sulfide, 1,2-propylene sulphide, thioepichlorohydrin, etc.

Suitable thietanes (e6) are 1,3-propylene sulphide, 3,3-dimethylthietane, etc.

The thermosetting compounds (e6) can be cured by thermal curing promoters. Suitable thermal curing promotors can be selected by the skilled artisan by the nature of the reactive functional groups in the binder. Suitable thermal curing promotors catalysts are e.g. sulfonium and phosphonium salts of organic or inorganic acids, imidazole and imidazole derivatives, quaternary ammonium compounds, and amines. The thermal curing promotors, where desired, are preferably used in an amount of from 0.001% by weight to about 10% by weight, based on the total weight of the polymerizable composition according to the invention.

It has been found that the afore-mentioned compounds of the formula (I) are in particular advantageous as thermal curing promoters for radically polymerizable compositions. In a special embodiment, they are used in resist formulations to manufacture color filters for a variety of display applications and for image sensors such as charge coupled device (CCD) and complementary metal-oxide semiconductor (CMOS). The polymerizable compositions according to the invention can further be used for manufacturing spacers such as transparent column spacer and black column spacer, which control a cell gap of the liquid crystal part in liquid crystal display panels. The polymerizable compositions according to the invention are also suitable as overcoat layer for color filters and LCDs, sealants for LCDs and OLEDs, insulation/passivation layers for LCDs, OLEDs, touch panels and flexible displays, bank/pixel definition layer of OLEDs, insulation for metal wiring/transparent conductive film for touch panels, coating for touch panels such as anti-fingerprint, hard coat and optical coat, decorative ink for touch panels, protective film for touch panels, etching resists for touch panels, resists or photosensitive compositions to generate structures or layers in the manufacturing processes of plasma-display panels, electroluminescence displays and LCDs, solder resists, and as a photoresist material used for forming dielectric layers in a sequential build-up layer of a printed circuit board. The use of compounds of the formula (I) results in a sufficiently high C=C conversion surprisingly at lower temperature and/or in shorter time in the thermal curing (post baking) process which takes place after the photo curing process both in comparison to corresponding compositions lacking these compounds (I) and in comparison to corresponding compositions comprising other thermal curing promoters (TCPs) known from the prior art.

According to a special embodiment, the polymerizable composition according to the invention comprises at least one binder polymer (d), wherein component (d) is selected from alkaline developable resins. Alkaline developable resins comprise functional groups that provide the resin with good alkaline solubility. They are suitable for all types of applications comprising a development step, wherein the uncured resin is dissolved in an alkaline developer solution.

Thus, the invention relates to a polymerizable composition comprising:
(a) at least one acrylate monomer,
(b) at least one oxime sulfonate compound of the formula I as defined above,
(c) at least one photoinitiator, and
(d) at least one alkaline developable resin.

Acrylate Monomer (a)

The polymerizable composition according to the invention preferably comprises the component (a) in an amount of from about 2 to 80% by weight, more preferably from about 5 to 70% by weight, based on the whole solid contents of the polymerizable composition (i.e. the amount of all components without the solvent(s)).

The acrylate monomer (a) is preferably selected from compounds that contain one or more (e.g. 1, 2, 3 or 4) acryloyl and/or methacryloyl moieties.

The term "acrylate monomer" encompasses also acrylate oligomers that contain one or more (e.g. 1, 2, 3 or 4) acryloyl and/or methacryloyl moieties.

Examples of compounds (a) containing a double bond are (meth)acrylic acid, alkyl(meth)acrylates, hydroxyalkyl (meth)acrylates or aminoalkyl(meth)acrylates. Preferred compounds (a) are for example methyl(meth)acrylate, ethyl (meth)acrylate, n-butyl(meth)acrylate, isobutyl(meth)acrylate, tert-butyl(meth)acrylate, n-propyl(meth)acrylate, isopropyl(meth)acrylate, n-hexyl(meth)acrylate, cyclohexyl (meth)acrylate, 2-ethylhexyl(meth)acrylate, isobornyl (meth)acrylate, benzyl(meth)acrylate, 2-hydroxyethyl (meth)acrylate, 2-hydroxypropyl(meth)acrylate, methoxyethyl(meth)acrylate, ethoxyethyl(meth)acrylate, glycerol(meth)acrylate, phenoxyethyl(meth)acrylate, methoxydiethylene glycol(meth)acrylate, ethoxydiethylene glycol(meth)acrylate, polyethylene glycol(meth)acrylate, polypropylene glycol(meth)acrylate, glycidyl(meth)acrylate, N, N-dimethylaminoethyl(meth)acrylate, N, N-diethylaminoethyl(meth)acrylate, and mixtures thereof.

Other examples of compounds (a) are (meth)acrylonitrile, (meth)acrylamide, N-substituted (meth)acrylamides, vinyl esters, vinyl ethers, styrene, alkylstyrenes, hydroxystyrenes, halostyrenes, N-vinylpyrrolidone, N-vinylcaprolactam, N-vinylacetamide, N-vinylformamide, vinyl chloride, vinylidene chloride, and mixtures thereof.

Suitable N-substituted (meth)acrylamides are e.g. N,N-dimethyl (meth)acrylamide, N,N-diethyl (meth)acrylamide, N,N-dibutyl (meth)acrylamide, N-methyl(meth)acrylamide, N-ethyl(meth)acrylamide, N-butyl(meth)acrylamide, N-(meth)acryloylmorpholine, and mixtures thereof Suitable vinyl esters are as vinyl acetate, vinyl propionate and mixtures thereof. A suitable vinyl ether is isobutyl vinyl ether.

Examples of polyunsaturated compounds (a) of relatively high molecular mass (oligomers) are polyesters, polyurethanes, polyethers and polyamides, which contain ethylenically unsaturated carboxylate groups. Particularly suitable examples are esters of an ethylenically unsaturated carboxylic acid with a polyol and/or polyepoxide.

Examples of unsaturated carboxylic acids are acrylic acid, methacrylic acid, crotonic acid, itaconic acid, cinnamic acid, and unsaturated fatty acids, such as linolenic acid or oleic acid. Acrylic acid and methacrylic acid are preferred.

Suitable polyols are aromatic, in particular, aliphatic and cycloaliphatic polyols. Examples of aromatic polyols are hydroquinone, 4,4'-dihydroxydiphenyl, 2,2-bis(4-hydroxyphenyl)methane, 2,2-bis(4-hydroxyphenyl)propane, 2,2-bis(4-hydroxyphenyl)hexafluoropropane, 9,9-bis(4hydroxyphenyl)fluorene, novolacs and resols. Examples of aliphatic and cycloaliphatic polyols are alkylenediols having preferably 2 to 12 C atoms, such as ethylene glycol, 1,2- or 1,3-propanediol, 1,2-, 1,3- or 1,4-butanediol, pentanediol, hexanediol, octanediol, dodecanediol, diethylene glycol, triethylene glcyol, polyethylene glycols having molecular weights of preferably from 200 to 1500, 1,3-cyclopentanediol, 1,2-, 1,3- or 1,4-cyclohexanediol, 1,4-dihydroxymethylcyclohexane, glycerol, triethanolamine, trimethylolethane, trimethylolpropane, pentaerythritol, pentaerythritol monooxalate, dipentaerythritol, ethers of pentaerythritol with ethylene glycol or propylene glycol, ethers of dipentaerythritol with ethylene glycol or propylene glycol, sorbitol, 2,2-bis[4-(2-hydroxyethoxy)phenyl]methane, 2,2-bis[4-(2-hydroxyethoxy)phenyl]propane and 9,9-bis[4-(2-hydroxyethoxy)phenyl]fluorene.

Further suitable polyols are polymers and copolymers containing hydroxy groups in the polymer chain or in side groups, examples being homopolymers or copolymers comprising vinyl alcohol or comprising hydroxyalkyl (meth)acrylates.

Further suitable polyols are esters and urethanes having hydroxyl end groups.

The polyols may be partially or completely esterified with one unsaturated carboxylic acid or with different unsaturated carboxylic acids. In partial esters the free hydroxyl groups may be modified, for example etherified or esterified with other carboxylic acids.

Examples of esters based on polyols are trimethylolpropane tri(meth)acrylate, trimethylolpropane tri(acryloyloxypropyl)ether, trimethylolethane tri(meth)acrylate, ethylene glycol di(meth)acrylate, diethylene glycol di(meth)acrylate, triethylene glycol di(meth)acrylate, tetraethylene glycol di(meth)acrylate, tetramethylene glycol di(meth)acrylate, neopentyl glycol di(meth)acrylate, pentaerythritol di(meth)acrylate, pentaerythritol tri(meth)acrylate, pentaerythritol tetra(meth)acrylate, pentaerythritol tri(meth)acrylate monooxalate, dipentaerythritol di(meth)acrylate, dipentaerythritol tri(meth)acrylate, dipentaerythritol tetra(meth)acrylate, dipentaerythritol penta(meth)acrylate, dipentaerythritol hexa(meth)acrylate, dipentaerythritol penta(meth)acrylate mono(2-hydroxyethyl) ether, tripentaerythritol octa(meth)acrylate, 1,3-butanediol di(meth)acrylate, 1,4-butanediol diitaconate, hexanediol di(meth)acrylate, 1,4-cyclohexanediol di(meth)acrylate, sorbitol tri(meth)acrylate, sorbitol tetra(meth)acrylate, sorbitol penta(meth)acrylate, sorbitol hexa(meth)acrylate, oligoester (meth)acrylates, glycerol di(meth)acrylate and tri(meth)acrylate, di(meth)acrylates of polyethylene glycol with a molecular weight of from 200 to 1500, pentaerythritol diitaconate, dipentaerythritol trisitaconate, dipentaerythritol pentaitaconate, dipentaerythritol hexaitaconate, ethylene glycol diitaconate, propylene glycol diitaconate, 1,3-butanediol diitaconate, 1,4-butanediol diitaconate, tetramethylene glycol diitaconate, sorbitol tetraitaconate, ethylene glycol dicrotonate, tetramethylene glycol dicrotonate, pentaerythritol dicrotonate, ethylene glycol dimaleate, tiethylene glycol dimaleate, pentaerythritol dimaleate, sorbitol tetramaleate, or mixtures thereof.

Other examples are pentaerythritol and dipentaerythritol derivatives shown in the following formula (XII) and (XIII):

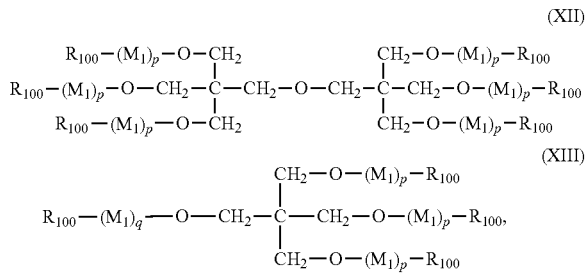

wherein
$M_1$ is —($CH_2CH_2O$)— or —[$CH_2CH(CH_3)O$]—,
$R_{100}$ is —$COCH{=}CH_2$ or —$COC(CH_3){=}CH_2$,
each p is independently 0 to 6,
the sum of all variables p is 3 to 24,
each q is independently 0 to 6, and
the sum of all variables q is 2 to 16.

Examples of polyepoxides are those based on the above-mentioned polyols and epichlorohydrin. Typical examples are bis(4-glycidyloxyphenyl)methane, 2,2-bis(4-glycidyloxyphenyl)propane, 2,2-bis(4-glycidyloxyphenyl)hexafluoropropane, 9,9-bis(4-glycidyloxyphenyl)fluorene, bis[4-(2-glycidyloxyethoxy)phenyl]methane, 2,2-bis[4-(2-glycidyloxyethoxy)phenyl]propane, 2,2-bis[4-(2-glycidyloxyethoxy)phenyl]hexafluoropropane, 9,9-bis[4-(2-glycidyloxyethoxy)phenyl]fluorene, bis[4-(2-glycidyloxypropoxy)phenyl]methane, 2,2-bis[4-(2- glycidyloxypropoxy)phenyl]propane, 2,2-bis[4-(2-glycidyloxypropoxy)phenyl]hexafluoropropane, 9,9-bis[4-(2-glycidyloxypropoxy)phenyl]fluorene, glycerol diglycidyl ether and glycidyl ethers of phenol and cresol novolacs.

Typical examples based on polyepoxides are 2,2-bis[4-{(2-hydroxy-3-acryloxy)propoxy}phenyl]propane, 2,2-bis[4-{(2-hydroxy-3-acryloxy)propoxyethoxy}phenyl]propane, 9,9-bis[4-{(2-hydroxy-3-acryloxy)propoxy}phenyl]fluorene, 9,9-bis[4-{(2-hydroxy-3-acryloxy)propoxyethoxy}phenyl]fluorine, glycerol 1,3-diglycerolate diacrylate and reaction products of epoxy resins based on novolacs with (meth)acrylic acid.

Preferred multifunctional (meth)acrylate monomers or oligomers include pentaerythritol tetraacrylate, dipentaerythritol pentaacrylate, dipentaerythritol hexaacrylate, di-trimethylolpropane tetraacrylate, pentaerythritol triacrylate, tris(2-hydroxy ethyl) isocyanurate triacrylate.

A particularly preferred acrylate monomer (a) is dipentaerythritol-hexaacrylate (DPHA). A further particularly preferred acrylate monomer (a) is dipentaerythritol-pentaacrylate (DPPA).

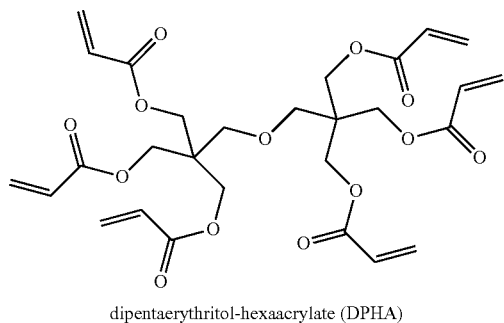

dipentaerythritol-hexaacrylate (DPHA)

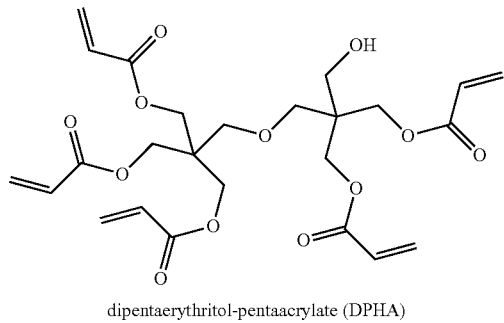

dipentaerythritol-pentaacrylate (DPHA)

Examples of commercially available compounds (a) having two acryloyl or methacryloyl moietyies are Aronix®M-210, Aronix®M-240, Aronix®M-6200 (TOAGOSEI Co., LDT., KAYARAD HDDA, KAYARAD HX-220, KAYARAD HX-620, KAYARAD R-526, KAYARAD UX-2201, KAYARAD MU-2100 (NIPPON KAYAKU Co., LTD.), VISCOAT-260, VISCOAT-355HP (OSAKA ORGANIC CHEMICAL INDUSTRY LTD.).

Examples of commercially available compounds (a) having three or more acryloyl or methacryloyl moietyies are Aronix®M-309, Aronix®M-400, Aronix®M-1310, Aronix®M-1960, Aronix®M-7100, Aronix®M-8530, Aronix®TO-1450 (TOAGOSEI Co., LDT.), KAYARAD TMPTA, KAYARAD DPHA, KAYARAD DPCA-20, KAYARAD MAX-3510 (NIPPON KAYAKU Co., LTD.), VISCOAT-295, VISCOAT-300, VISCOAT-GPT, VISCOAT-3PA, VISCOAT-400 (OSAKA ORGANIC CHEMICAL INDUSTRY LTD.).

Examples of commercially available urethane acrylate monomers (a) having two or more acryloyl or methacryloyl moietyies are NEW FRONTIER R-1150 (DAI-ICHI KOGYO SEIYAKU CO., LTD.) KAYARAD DPHA-40H, KAYARAD UX-5000 (NIPPON KAYAKU Co., LTD.), UN-9000H (Negami Chemical Industrial Co., Ltd.).

Photoinitiator (c)

The choice of a suitable photoinitiator (c) is usually not critical. The photoinitiator (c) is for example selected from benzophenone, benzophenone derivatives, bisimidazole, bisimidazole derivatives aromatic α-hydroxyketones, benzylketals, aromatic α-aminoketones, phenylglyoxalic acid esters, mono-acylphosphinoxides, bis-acyl phosphinoxides, tris-acylphosphinoxides, oximesters derived from aromatic ketones and/or oxime esters of the carbazol type.

Examples of photoinitiators (c) are
camphorquinone (1,7,7-trimethyl-bicyclo[2.2.1]heptane-2,3-dione); benzophenone and benzophenone derivatives, such as 2,4,6-trimethylbenzophenone, 2-methylbenzophenone, 3-methylbenzophenone, 4-methylbenzophenone, 2-methoxycarbonylbenzophenone, 4,4'-bis(chloromethyl) benzophenone, 4-chlorobenzophenone, 4-phenylbenzophenone, 3,3'-dimethyl-4-methoxy-benzophenone, [4-(4-methylphenylthio)phenyl]-phenylmethanone, methyl-2-benzoylbenzoate, 3-methyl-4'-phenylbenzophenone, 2,4,6-trimethyl-4'-phenylbenzophenone, 4,4'-bis(dimethylamino) benzophenone, 4,4'-bis(diethylamino)benzophenone;
thioxanthones and thioxanthone derivatives, e.g. polymeric thioxanthones like OMNIP-OL TX(diester of 2-carboxymethoxy thioxanthone and polytetramethyleneglycol 250);
ketal compounds, as for example benzildimethylketal (Irgacure® 651);
acetophenone and acetophenone derivatives, for example α-hydroxycycloalkyl phenyl ketones or α-hydroxyalkyl phenyl ketones, such as for example 2-hydroxy-2-methyl-1-phenyl-propanone (Irgacure® 1173), 1-hydroxy-cyclohexyl-phenyl-ketone (Irgacure® 184), 1-(4-dodecylbenzoyl)-1-hydroxy-1-methyl-ethane, 1-(4-isopropylbenzoyl)-1-hydroxy-1-methyl-ethane, 1-[4-(2-hydroxyethoxy)-phenyl]-2-hydroxy-2-methyl-1-propan-1-one (Irgacure® 2959), 2-hydroxy-1-{4-[4-(2-hydroxy-2-methyl-propionyl)-benzyl]-phenyl}-2-methyl-propan-1-one (Irgacure®127); 2-hydroxy-1-{4-[4-(2-hydroxy-2-methyl-propionyl)-phenoxy]-phenyl}-2-methyl-propan-1-one;
dialkoxyacetophenones, α-hydroxyacetophenones or α-aminoacetophenones, e.g. (4-methylthiobenzoyl)-1-methyl-1-morpholinoethane (Irgacure® 907), (4-morpholinobenzoyl)-1-benzyl-1-dimethylaminopropane (Irgacure® 369), (4-morpholinobenzoyl)-1-(4-methylbenzyl)-1-dimethylaminopropane (Irgacure® 379), (4-(2-hydroxyethyl)aminobenzoyl)-1-benzyl-1-dimethylaminopropane), (3,4-dimethoxybenzoyl)-1-benzyl-1-dimethylaminopropane;
4-aroyl-1,3-dioxolanes, benzoin alkyl ethers and benzil ketals, e.g. dimethyl benzil ketal;
phenylglyoxalic esters and derivatives thereof, e.g. methyl α-oxo benzeneacetate, oxophenyl-acetic acid 2-(2-hydroxy-ethoxy)-ethyl ester, dimeric phenylglyoxalic esters, e.g. oxophenyl-acetic acid 1-methyl-2-[2-(2-oxo-2-phenyl-acetoxy)-propoxy]-ethyl ester (Irgacure® 754);
ketosulfones, e.g. ESACURE KIP 1001 M;
oximeesters, e.g. 1,2-octanedione 1-[4-(phenylthio)phenyl]-2-(O-benzoyloxime), ethanone 1-[9-ethyl-6-(2-methylbenzoyl)-9H-carbazol-3-yl]-1-(O-acetyloxime), ethanone 1-[9-ethyl-6-(2-methyl-4-(2,2-dimethyl-1,3-dioxolanyl) methoxybenzoyl)-9H-carbazol-3-yl]-1-(O-acetyloxime), methanone, [8-[[(acetyloxy)imino][2-(2,2,3,3-tetrafluoro-propoxy)phenyl]methyl]-11-(2-ethylhexyl)-11H-benzo[a]carbazol-5-yl](2,4,6-trimethylphenyl), N-acetoxy-N-{3-[9-ethyl-6-(naphthalene-1-carbonyl)-9H-carbazol-3-yl]-1-methyl-3-acetoxyimino-propyl}-acetamide,
9H-thioxanthene-2-carboxaldehyde 9-oxo-2-(O-acetyloxime), [(E)-[1-(cyclohexylmethyl)-2-oxo-2-(4-phenylsulfanylphenyl)ethylidene]amino] cyclopropanecarboxylate), [(E)-[1-(cyclohexylmethyl)-2-oxo-2-(4-phenylsulfanylphenyl)ethylidene]amino] acetate, [(E)-[1-(o-tolyl)-2-oxo-2-(4-phenylsulfanylphenyl)ethylidene]amino] acetate, [(E)-1-[9-ethyl-6-(thiophene-2-carbonyl)carbazol-3-yl]
ethylideneamino] acetate, [(E)-1-[9-ethyl-6-(thiophene-2-carbonyl)carbazol-3-yl]propylideneamino] acetate, the oxime esters described in WO 07/062963, WO 07/071797, WO 07/071497, WO 05/080337, JP2010-049238, WO2008078678, JP2010-15025 and JP2010-49238 peresters, e.g. benzophenone tetracarboxylic peresters as described for example in EP 126541;
monoacylphosphine oxides, e.g. (2,4,6-trimethylbenzoyl)diphenylphosphine oxide (Irgacure® TPO), ethyl (2,4,6 trimethylbenzoyl phenyl) phosphinic acid ester;
bisacylphosphine oxides, e.g. bis(2,6-dimethoxy-benzoyl)-(2,4,4-trimethyl-pentyl)phosphine oxide, bis(2,4,6-trimethylbenzoyl)-phenylphosphine oxide (Irgacure® 819), bis(2,4,6-trimethylbenzoyl)-2,4-dipentoxyphenylphosphine oxide;
trisacylphosphine oxides;
halomethyltriazines, e.g. 2-[2-(4-methoxy-phenyl)-vinyl]-4,6-bis-trichloromethyl-[1,3,5]-triazine, 2-(4-methoxy-phenyl)-4,6-bis-trichloromethyl-[1,3,5]triazine, 2-(3,4-dimethoxyphenyl)-4,6-bis-trichloromethyl-[1,3,5]triazine, 2-methyl-4,6-bis-trichloromethyl-[1,3,5]triazine;
hexaarylbisimidazole/coinitiators systems, e.g. ortho-chlorohexaphenyl-bisimidazole combined with 2-mercaptobenzthiazole, ferrocenium compounds, or titanocenes, e.g. bis(cyclopentadienyl)-bis(2,6-difluoro-3-pyrryl-phenyl) titanium (Irgacure®784). Further, borate compounds can be used as coinitiators.

As additional photoinitiators oligomeric compounds such as for example oligomeric alpha hydroxyl ketones e.g. 2-hydroxy-1-{1-[4-(2-hydroxy-2-methyl-propionyl)-phenyl]-1,3,3-trimethyl-indan-5-yl}-2-methyl-propan-1-one, ESACURE KIP provided by Fratelli Lamberti, or oligomeric alpha amino ketones may be employed as well.

Examples of commercially available oxime esters are TR-TBG-304, TR-TBG-305, TR-TBG-309, TR-TBG-311, TR-TBG-313, TR-TBG-314, TR-TBG-316, TR-TBG-317, (Changzhou Tronly New Electronic Materials Co., LDT.).

Examples of commercially available oxime esters are TR—
Specific examples of photoinitiators (c) are:
(2-Benzyl-2-(dimethylamino)-1-[4-(4-morpholinyl)phenyl]-1-butanone), (2-(4-methylbenzyl)-2-(dimethylamino)-1-[4-(4-morpholinyl)phenyl]-1-butanone, 1,2-octanedione, 1-[4-(phenylthio)phenyl]-2-(O-benzoyloxime), ethanone 1-[9-ethyl-6-(2-methylbenzoyl)-9H-carbazol-3-yl]-1-(O-acetyloxime).

Alkaline Developable Resin (d)

The polymerizable composition according to the invention preferably comprises the component (d) in an amount of from 2 to 98% by weight, more preferably from 5 to 90% by weight, in particular from 10 to 80% by weight, based on the whole solid contents of the polymerizable composition (i.e. the amount of all components without the solvent(s)).

Preferably, the alkaline developable resin has free carboxylic groups. The acid number is preferably from 50 to 600 mg KOH/g, more preferably 100 to 300 mg KOH/g. The acid numbers stated here are the acid number according to DIN EN 12634.

Examples of alkali developable resins are acrylic polymers having carboxylic acid function as a pendant group, such as copolymers obtained by copolymerizing an ethylenic unsaturated carboxylic acid such as (meth)acrylic acid, 2-carboxyethyl (meth)acrylic acid, 2-carboxypropyl (meth)acrylic acid, itaconic acid, citraconic acid, mesaconic acid, fumaric acid, crotonic acid, maleic acid, maleic anhydride, fumaric anhydride, citraconic acid, mesaconic acid, itaconic acid, half-ester of maleic acid, cinnamic acid, mono[2-(meth)acryloyloxyethyl] succinate, mono[2-(meth)acryloyloxyethyl] adipate, mono[2-(meth)acryloyloxyethyl] phthalate, mono[2-(meth)acryloyloxyethyl] hexahydrophthalate, mono[2-(meth)acryloyloxyethyl] maleate, mono[2-(meth)acryloyloxypropyl] succinate, mono[2-(meth)acryloyloxypropyl] adipate, mono[2-(meth)acryloyloxypropyl] phthalate, mono[2-(meth)acryloyloxypropyl] hexahydrophthalate, mono[2-(meth)acryloyloxypropyl] maleate, mono[2-(meth)acryloyloxybutyl] succinate, mono[2-(meth)acryloyloxybutyl] adipate, mono[2-(meth)acryloyloxybutyl] phthalate, mono[2-(meth)acryloyloxybutyl] hexahydrophthalate, mono[2-(meth)acryloyloxybutyl] maleate, 3-(alkylcarbamoyl)acrylic acid, α-chloroacrylic acid, maleic acid, monoesterified maleic acid, citraconic acid and ω-carboxypolycaprolactone mono(meth)acrylate, with one or more monomers selected from esters of (meth)acrylic acid, such as methyl (meth)acrylate, ethyl (meth)acrylate, propyl (meth)acrylate, butyl (meth)acrylate, benzyl (meth)acrylate, 2-ethylhexyl (meth)acrylate, hydroxyethyl (meth) acrylate, hydroxypropyl (meth)acrylate, tetrahydrofurfuryl (meth)acrylate, hydroxybutyl (meth)acrylate, glycerol mono(meth)acrylate, dihydroxypropyl (meth)acrylate, allyl (meth)acrylate, cyclohexyl (meth)acrylate, phenyl (meth)acrylate, methoxyphenyl (meth)acrylate, methoxyethyl (meth)acrylate, phenoxyethyl (meth)acrylate, methoxydiethyleneglycol (meth)acrylate, methoxytriethyleneglycol (meth)acrylate, methoxypropyl (meth)acrylate, methoxydipropyleneglycol (meth)acrylate, (3-trimetoxysilyl)propyl(meth)acrylate, (meth)acrylic acid trimethyl silyl ester, (meth)acrylate, isobornyl (meth)acrylate, dicyclopentadienyl (meth)acrylate, 2-hydroxy-3-phenoxypropyl (meth)acrylate, tricyclo[5.2.1.0$^{2,6}$]decan-8-yl (meth)acrylate, aminoethyl (meth)acrylate, N,N-dimethylaminoethyl (meth) acrylate, aminopropyl (meth)acrylate, N,N-dimethylaminopropyl (meth)acrylate, glycidyl (meth)acrylate, 2-methylglycidyl (meth)acrylate, 3,4-epoxybutyl (meth)acrylate, 6,7-epoxyheptyl (meth)acrylate; vinyl aromatic compounds, such as styrene, α-methylstyrene, vinyltoluene, p-chlorostyrene, polychlorostyrene, fluorostyrene, bromostyrene, ethoxymethyl styrene, methoxystyrene, 4-methoxy-3-methystyrene, dimethoxystyrene, vinylbenzyl methyl ether, vinylbenzyl glycidyl ether, indene, 1-methylindene, 1-ethenyl-4-silylbenzen, 1-ethenyl-4-trimethylsilyl-benzene, t-buthyl dimethylsilyl p-vinyl phenyl ether; amide type unsaturated compounds, such as (meth)acrylamide, diacetone acrylamide, N-methylolacrylamide, N-butoxymethacrylamide, N,N-dimethyl (meth)acrylamide, N, N-diethyl (meth)acrylamide, N,N-dibutyl (meth)acrylamide, N,N-diethylhexyl (meth)acrylamide, N, N-dicyclohexyl (meth)acrylamide, N,N-diphenyl (meth)acrylamide, N-methyl-N-phenyl (meth)acrylamide, N-hydroxyethyl-N-methyl (meth)acrylamide, N-methyl (meth)acrylamide, N-ethyl (meth)acrylamide, N-propyl (meth)acrylamide, N-butyl (meth)acrylamide, N-hydroxyethyl (meth)acrylamide, N-heptyl (meth)acrylamide, N-octyl (meth)acrylamide, N-ethylhexyl (meth)acrylamide, N-hydroxyethyl (meth)acrylamidecyclohexyl, N-benzyl (meth)acrylamide, N-phenyl (meth)acrylamide, N-tolyl (meth)acrylamide, N-hydroxyphenyl (meth)acrylamide, N-naphthyl (meth)acrylamide, N-phenylsulfonyl (meth)acrylamide, N-methylphenylsulfonyl (meth)acrylamide and N(meth)acryloylmorpholine; acetal ester or ketal ester compounds, such as norbornene, 2,3-di-trimetylsilanyloxycarbonyl-5-norbornene, 3-di-trietylsilanyloxycarbonyl-5-norbornene, 2,3-di-t-butyldimethylsilanyloxycarbonyl-5-norbornene, 2,3-di-trimethylgermyloxycarbonyl-5-norbornene, 2,3-di-triethylgelmyloxycarbonyl-5-norbornene, 2,3-di-t-butyldimethylgermyloxycarbonyl-5-norbornene, 2,3-di-t-butyloxycarbonyl-5-norbornene, 2,3-di-benzyloxycarbonryl-5-norbornene, 2,3-di-tetrahydrofurane-2-yloxycarbonyl-5-norbornene, 2,3-di-cyclopentyloxycarbonyl-5-norbornene, 2,3-di-cyclohexyloxycarbonyl-5-norbornene, 2,3-di-cycloheptyloxycarbonyl-5-norbornene, 2,3-di-1-methoxyethoxycarbonyl-5-norbornene, 2,3-di-1-t-buthoxyethoxycarbonyl-5-norbornene, 2,3-di-1-benzyloxyethoxycarbonyl-5-norbornene, 2,3-di-(cyclohexyl)(ethoxy)methoxycarbonyl-norbornene, 2,3-di-1-methyl-1-methoxyethoxycarbonyl-5-norbornene, 2,3-di-1-methyl-1-i-butoxyethoxycarbonyl-5-norbornene, 2,3-di-(benzyl)(ethoxy)methoxycarbonyl-5-norbornene;
1-alkylcycloalkylester compounds, such as 1-metylcyclopropane(meth)acrylate, 1-methylcyclobutane(meth)acrylate, 1-methylcyclopentyl(meth)acylate, 1-methylcyclohexyl(meth)acrylate, 1-methylcycloheptane(meth)acrylate, 1-methylcyclooctane(meth)acrylate, 1-methylcyclononane (meth)acrylate, 1-ethylcyclodecane(meth)acrylate, 1-ethylcyclopuropane(meth)acrylate, 1-ethylcyclobutane(meth)acrylate, 1-ethylcyclopentyl(meth)acrylate, 1-ethylcyclohexyl(meth)acrylate, 1-ethylcycloheptane(meth)acrylate, 1-ethylcyclooctane(meth)acrylate, 1-ethylcyclononane(meth)acrylate, 1-ethylcyclodecane(meth)acrylate, 1-(iso)puropylcyclopuropane(meth)acrylate, 1-(iso)propylcyclopropane(meth)acrylate, 1-(iso)puropylcyclopentyl(meth)acrylate, 1-(iso)propylcyclohexyl(meth)acrylate, 1-(iso)propylcycloheptane(meth)acrylate, 1-(iso)propylcyclooctane(meth)acrylate, 1-(iso)propylcyclononane(meth)acrylate 1-(iso)propylcyclodecane(meth)acrylate, 1-(iso)butylcyclopuropane(meth)acrylate, 1-(iso)butylcyclobutane(meth)acrylate, 1-(iso)butylcyclopentyl(meth)acrylate, 1-(iso)butylcyclohexyl(meth)acrylate, 1-(iso)butylcyclohexyl(meth)acrylate, 1-(iso)butylcyclooctane(meth)acrylate, 1-(iso)-butylcyclononane(meth)acrylate, 1-(iso)butylcyclodecanyl(meth)acrylate, 1-(iso)pentylcyclopuropanyl(meth)acrylate, 1-(iso)pentylcyclopentyl(meth)acrylate, 1-(iso)pentylcyclopentyl(meth)acrylate, 1-(iso)pentylcyclohexyl(meth)acrylate, 1-(iso)Pentylcycloheptanyl(meth)acrylate, 1-(iso)pentylcyclooctane(meth)acrylate, 1-(iso)Pentylcyclononyl(meth)acrylate, 1-(iso)pentylcyclodecanyl(meth)acrylate, 1-(iso)octylcyclopuropanyl (meth)acrylate, 1-(iso)octylcyclobutabtyl(meth)acrylate, 1-(iso)octylcyclooctyl(meth)acrylate, 1-(iso)octylcycloheptanyl(meth)acrylate, 1-(iso)octylcycloheptanyl(meth)acrylate, 1-(iso)octylcyclooctanyl(meth)acrylate, 1-(iso)octylcyclononanyl(meth)acrylate, 1-(iso)octylcyclodecanyl(meth)acrylate; methacryl acids, such as 3-(methacryloyloxymethyl)oxetane, 3-(methacryloyloxyethyl)-3-ethyloxetane, 3-(methacryloyloxymethyl)-2-methyloxetane, 3-(methacryloyloxymethyl)-2-methyloxetane, 3-(methacryloyloxymethyl)-2-trifrollomethyloxetane, 3-(methacryloyloxynethyl)-2-pentaflouroethyloxetane, 3-(methacryloyloxymethyl)-2-phenyloxetane, 3-(methacryloyloxymethyl)-2,2-difrollooxetane, 3-(methacryloyloxymethyl)-2,2,4,-trifrollooxetane, 3-(methacryloyloxymethyl)-2,2,4,4-tetrafrollooxetane, 3-(methacryloyloxyethyl)oxetane, 3-(methacryloyloxyethyl)-3-ethyloxetane, 2-ethyl-3-(methacryloyloxyethyl)oxetane, 3-(methacryloyloxyethyl)-2-trifluoromethyloxetane, 3-(methacryloyloxyethyl)-2-pentafluoroethyloxetane, 3-(methacryloyloxyethyl)-2-phenyloxetane, 2,2-difluoro-3-(methacryloyloxyethyl)oxetane, 3-(methacryloyloxyethyl)-2,2,4-trifrollooxetane, 3-(methacryloyloxyethyl)-2,2,4,4,-tetrafluorooxetane; polycyclic compounds or anhydride, such as 5-carboxybicyclo[2.2.1]hept-2-ene, 5,6-dicarbocybicyclo[2.2.1]hept-2-ene, 5-carboxy-5-methylbicyclo[2.2.1]hept-2-ene, 5-carboxy-6-ethylbicyclo[2.2.1]hept-2-ene, 5-carboxy-6-methylbicyclo[2.2.1]hept-2-ene, 5-carboxy-6-ethylbicyclo[2.2.1]hept-2-ene, 5,6-dicarboxybicyclo[2.2.1]hept-2-eneanhydride; vinyl or allyl esters, such as vinyl acetate, vinyl propionate, vinyl butylate, vinyl pivalate, vinyl benzoate, vinyl trimethylacetate, vinyl diethylacetate, vinyl barate, vinyl caproate, vinyl chloroacetate, vinyl dichloroacetate, vinyl methoxyacetate, vinyl butoxyacetate, vinyl phenylacetate, vinyl acetate, vinyl acetoacetate, vinyl lactate, vinyl phenylbutylate, vinyl cyclohexylcarboxylate, vinyl salicylate, vinyl chlorobenzoate, vinyl tetrachlorobenzoate, vinyl naphthoate, vinyl triethoxysilane, allyl acetate, allyl propionate, allyl butylate, allyl pivalate, allyl benzoate, allyl caproate, allyl stearate, allyl acetoacetate, allyl lactate; vinyl or allyl ethers, such as vinyl methyl ether, vinyl ethyl ether, vinyl hexyl ether, vinyl octyl ether, vinyl ethylhexyl ether, vinyl methoxyethyl ether, vinyl ethoxyethyl ether, vinyl chloroethyl ether, vinyl hydroxyethyl ether, vinyl ethybutyl ether, vinyl hydroxyethoxyethyl ether, vinyl dimethylaminoethyl ether, vinyl diethylaminoethyl ether, vinyl butylaminoethyl ether, (ethenyloxy)methyl silane, vinyl benzyl ether, vinyl tetrahydrofurfuryl ether, vinyl phenyl ether, vinyl tolyl ether, vinyl chlorophenyl ether, vinyl chloroethyl ether, vinyl dichlorophenyl ether, vinyl naphthyl ether, vinyl anthryl ether, allyl glycidyl ether; crotonates, such as butyl crotonate, hexyl crotonate, glycerine monocrotonate; itaconates, such as dimethyl itaconate, diethyl itaconate, dibutyl itaconate; and maleates or fumarates, such as dimethyl mareate, dibutyl fumarate; polyolefin type compounds, such as butadiene, isoprene, chloroprene and the like; methacrylonitrile, methyl isopropenyl ketone, vinyl acetate, vinyl propionate, vinyl pivalate, maleimide, N-phenylmaleimide, N-methylphenylmaleimide, N-methoxyphenylmaleimide, N-cyclohexylmaleimide, N-alkylmaleimide, maleic anhydride, polystyrene macromonomer, polymethyl (meth)acrylate macromonomer, polybutyl (meth)acrylate macromonomer. Examples of copolymers are copolymers of acrylates and methacrylates with acrylic acid or methacrylic acid and with styrene or substituted styrene, phenolic resins, for example novolak, (poly)hydroxystyrene, and copolymers of hydroxystyrene with alkyl acrylates, acrylic acid and/or methacrylic acid. Preferable examples of copolymers are copolymers of methyl (meth)acrylate/(meth)acrylic acid, copolymers of benzyl (meth)acrylate/(meth)acrylic acid, copolymers of methyl (meth)acrylate/ethyl (meth)acrylate/ (meth)acrylic acid, copolymers of benzyl (meth)acrylate/ (meth)acrylic acid/styrene, copolymers of benzyl (meth) acrylate/(meth)acrylic acid/hydroxyethyl (meth)acrylate, copolymers of benzyl (meth)acrylate/(meth)acrylic acid/ glycidyl (meth)acrylate, copolymers of benzyl (meth)acrylate/(meth)acrylic acid/3-(methacryloyloxymethyl)oxetane, copolymers of methyl (meth)acrylate/butyl (meth)acrylate/ (meth)acrylic acid/styrene, copolymers of methyl (meth) acrylate/benzyl (meth)acrylate/(meth)acrylic acid/hydroxyphenyl (meth)acrylate, copolymers of methyl (meth) acrylate/(meth)acrylic acid/polymethyl (meth)acrylate macromonomer, copolymers of benzyl (meth)acrylate/(meth)acrylic acid/polymethyl (meth)acrylate macromonomer, copolymers of tetrahydrofurfuryl (meth)acrylate/styrene/(meth)acrylic acid, copolymers of methyl (meth) acrylate/(meth)acrylic acid/polystyrene macromonomer, copolymers of benzyl (meth)acrylate/(meth)acrylic acid/polystyrene macromonomer, copolymers of benzyl (meth)acrylate/(meth)acrylic acid/2-hydroxyethyl (meth)acrylate/polystyrene macromonomer, copolymers of benzyl (meth)acrylate/(meth)acrylic acid/2-hydroxypropyl (meth)acrylate/polystyrene macromonomer, copolymers of benzyl (meth)acrylate/(meth)acrylic acid/2-hydroxy-3-phenoxypropyl (meth)acrylate/polymethyl (meth)acrylate macromonomer, copolymers of methyl (meth)acrylate/(meth)acrylic acid/2-hydroxyethyl (meth)acrylate/polystyrene macromonomer, copolymers of benzyl (metha)crylate/(meth)acrylic acid/2-hydroxyethyl (meth)acrylate/polymethyl (meth)acrylate macromonomer, copolymers of N-phenylmaleimide/benzyl (meth)acrylate/(meth)acrylic acid and styrene, copolymers of benzyl (meth)acrylate/(meth)acrylic acid/N-phenylmaleimide/mono[2-(meth)acryloyloxyethyl] succinate/styrene, copolymers of allyl (meth)acrylate/(meth) acrylic acid/N-phenyl-maleimide/mono-[2-(meth)acryloyloxyethyl] succinate/styrene, copolymers of benzyl (meth) acrylate/(meth)acrylic acid/N-phenylmaleimide/glycerol mono(meth)acrylate/styrene, copolymers of benzyl (meth) acrylate/ω-carboxypolycaprolactone mono(meth)acrylate/(meth)acrylic acid/N-phenylmaleimide/glycerol mono (meth)acrylate/styrene, and copolymers of benzyl (meth) acrylate/(meth)acrylic acid/N-cyclohexylmaleimide/styrene. Example of commercial product is Ripoxy SPC-2000 provided by Showa Highpolymer.

As mentioned before, the alkaline developable resin (d) has preferably free carboxylic groups, which provide the compounds with good alkaline solubility. However, it is also possible to employ functional groups that are different from carboxylic groups, in order to obtain a resin with good alkaline solubility. Examples for such groups are phenolic groups, sulfonic acid groups, anhydride groups, and combinations thereof.

Typical examples of the aforementioned acid anhydride are dibasic acid anhydrides such as for example maleic anhydride, succinic anhydride, itaconic anhydride, phthalic anhydride, tetrahydrophthalic anhydride, hexahydrophthalic anhydride, methylhexahydrophthalic anhydride, endo-methylenetetrahydrophthalic anhydride, methyl-endo-methylenetetrahydrophthalic anhydride, chlorendic anhydride, and methyltetrahydrophthalic anhydride. Suitable are also aromatic polycarboxylic anhydrides, for example trimellitic anhydride, pyromelic anhydride and benzophenone tetracarboxylic dianhydride. Suitable are also polycarboxylic anhydride derivatives such as 5-(2,5-dioxotetrahydrofuryl)-3-methyl-3-cyclohexene-1, 2-dicarboxylic anhydride.

Further examples of alkaline developable resins (d) are polymers or oligomers having at least two ethylenically unsaturated groups and at least one carboxyl function within the molecule structure, such as a resin obtained by the reaction of a saturated or unsaturated polybasic acid anhydride with a product of the reaction of an epoxy compound and an unsaturated monocarboxylic acid (for example, EB9696 from UCB Chemicals; KAYARAD TCR1025 from Nippon Kayaku Co. LTD.; NK OLIGO EA-6340, EA-7440 from Shin-Nakamura Chemical Co., Ltd.). Other examples of such binders are described in JP2002-206014A, JP2004-69754A, JP2004-302245A, JP2005-77451A, JP2005-316449A, JP2005-338328A and JP375406562.

Further examples of alkaline developable resins (d) are the above-mentioned polymers or oligomers having at least one ethylenically unsaturated groups Further examples of alkaline developable resins (d) are reaction products obtained by adding an epoxy group containing unsaturated compound to a part of the carboxyl groups of a carboxylic acid group containing polymer (for ex., ACA200, ACA200M, ACA210P, ACA230AA, ACA250, ACA300, ACA320 from Daicel Chemical Industries, Ltd. and Ripoxy SPC-1000 provided by Showa Highpolymer). As the carboxylic acid containing polymer, the abovementioned binder polymers which are resulting from the reaction of an unsaturated carboxylic acid compound with one or more polymerizable compounds, for example, copolymers of (meth)acrylic acid, benzyl (meth)acrylate, styrene and 2-hydroxyethyl (meth)acrylate, copolymers of (meth)acrylic acid, styrene and α-methystyrene, copolymers of (meth)acrylic acid, N-phenylmaleimide, styrene and benzyl (meth)acrylate, copolymers of (meth)acrylic acid and styrene, copolymers of (meth)acrylic acid and benzyl (meth) acrylate, copolymers of tetrahydrofurfuryl (meth)acrylate, styrene and (meth)acrylic acid and the like.

Examples of the unsaturated compounds having an epoxy group are given below in the formula (V-1)-(V-15);

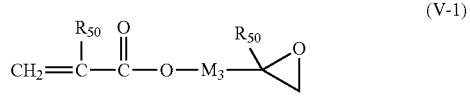

(V-1)

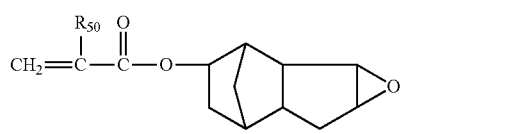

(V-2)

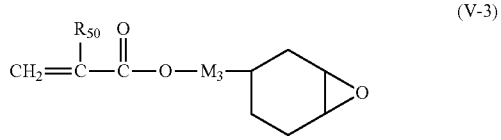

(V-3)

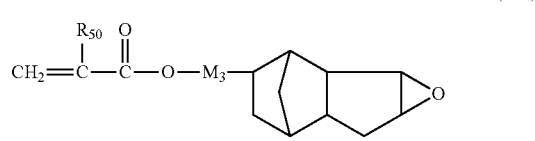

(V-4)

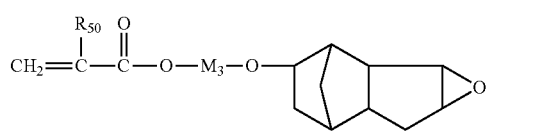

(V-5)

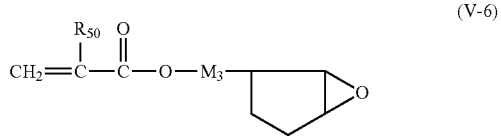

(V-6)

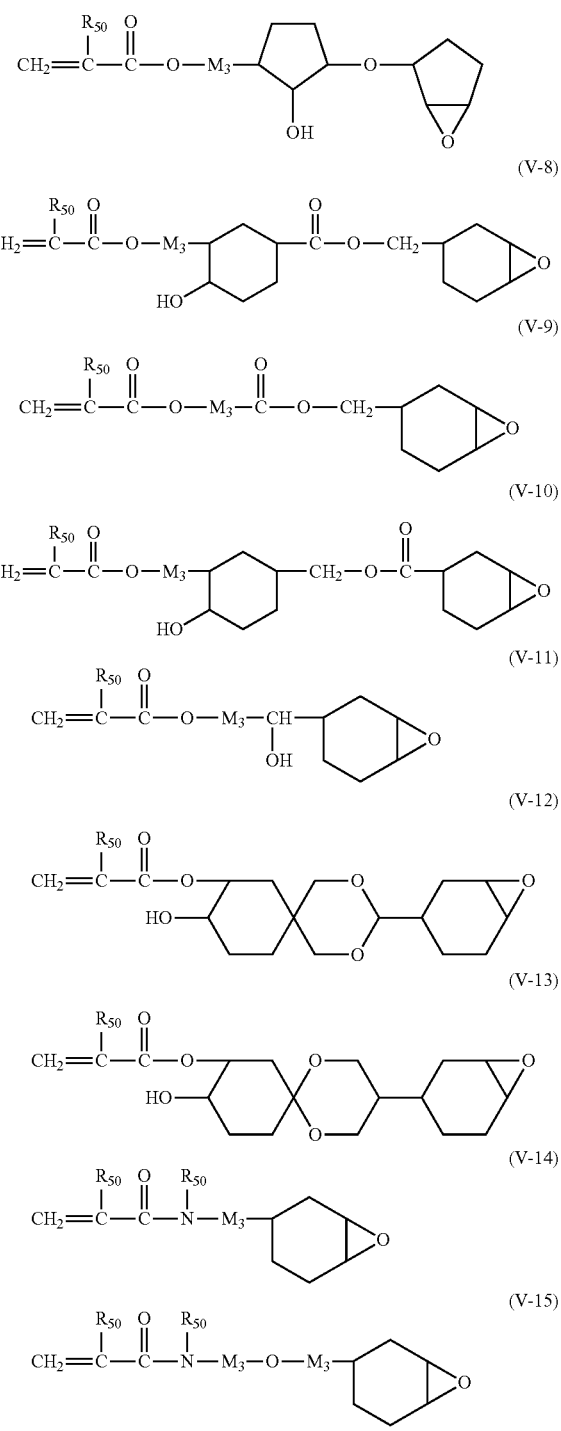

(V-7) (V-8) (V-9) (V-10) (V-11) (V-12) (V-13) (V-14) (V-15)

wherein $R_{50}$ is hydrogen or a methyl group, and $M_3$ is substituted or unsubstituted alkylene having 1 to 10 carbon atoms.

Among these compounds, compounds having alicyclic epoxy groups are particularly preferred, because these compounds have a high reactivity with carboxyl group-containing resins, accordingly the reaction time can be shortened. These compounds further do not cause gelation in the process of reaction and make it possible to carry out the reaction stably. On the other hand, glycidyl acrylate and glycidyl methacrylate are advantageous from the viewpoint of sensitivity and heat resistance because they have a low molecular weight and can give a high conversion of esterification.

Concrete examples of the abovementioned compounds are, for example a reaction product of a copolymer of styrene, α-methyl styrene and acrylic acid or a copolymer of methyl methacrylate and acrylic acid with 3,4-epoxycyclohexylmethyl (meth)acrylate.

Further examples are products obtained by addition reaction of an epoxy group containing unsaturated compound to a part of or all of the carboxyl groups of a carboxylic acid group containing polymer followed by further reaction with polybasic acid anhydride (for ex., Ripoxy SPC-3000 provided by Showa Highpolymer).

Unsaturated compounds having a hydroxy group such as 2-hydroxyethyl (meth)acrylate and glycerol mono(meth)acrylate can be used instead of the above mentioned epoxy group containing unsaturated compounds as the reactant for carboxylic acid group containing polymers.

Further examples are half esters of anhydride containing polymers, for example reaction products of a copolymer of maleic anhydride and one or more other polymerizable compounds with (meth)acrylates having an alcoholic hydroxyl group such as 2-hydroxyethyl (meth)acrylate or having an epoxy group for example such as the compounds described in the formula (V-1)-(V-15).

Reaction products of polymers having alcoholic hydroxyl groups such as copolymers of 2-hydroxyethyl (meth)acrylate, (meth)acrylic acid, benzyl methacylate and styrene, with (meth)acrylic acid or (meth)acryl chloride can also be used.

Further examples are reaction products of a polyester with terminal unsaturated groups, which is obtained from the reaction of a dibasic acid anhydride and a compound having at least two epoxy groups followed by further reaction with an unsaturated compound, with a polybasic acid anhydride.

Further examples are resins obtained by the reaction of a saturated or unsaturated polybasic acid anhydride with a reaction product obtained by adding epoxy group containing (meth)acrylic compound to all of the carboxyl groups of a carboxylic acid containing polymer as mentioned above.

Further example is polyimide resin having ethylenically unsaturated groups and at least one carboxyl function. The polyimide binder resin in the present invention can be a polyimide precursor, for example, a poly(amic acid).

Specific examples of alkali developable resins (d) are:
Acrylpolymer type resins such as

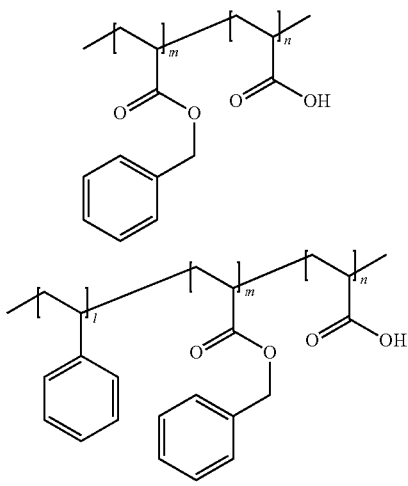

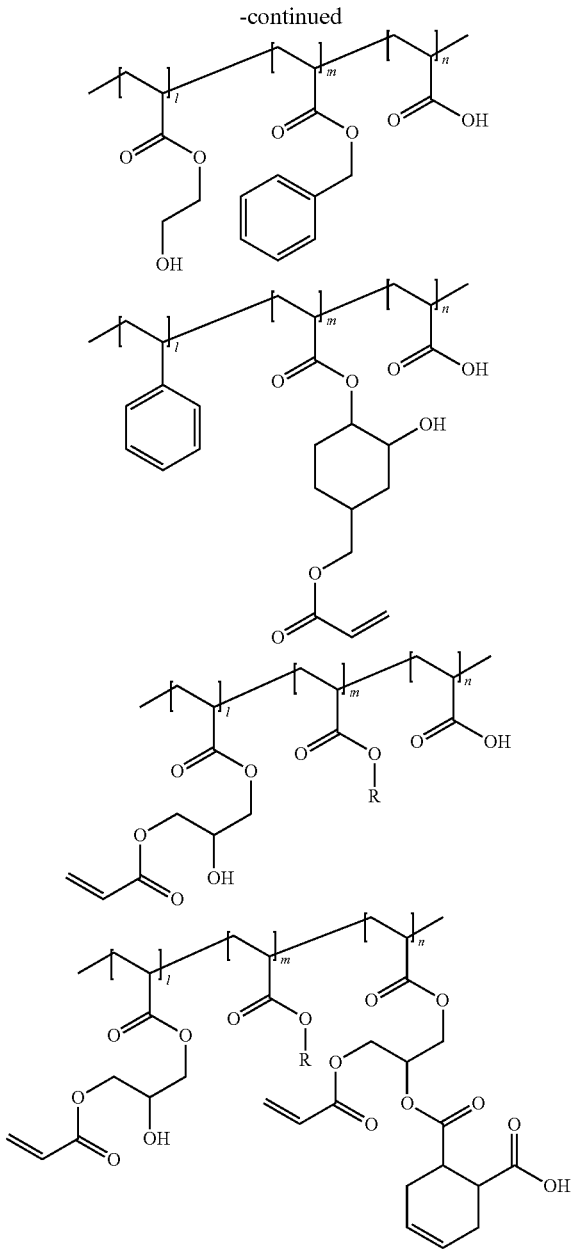

Cardo type resin (fluorene epoxy acrylate based resin)

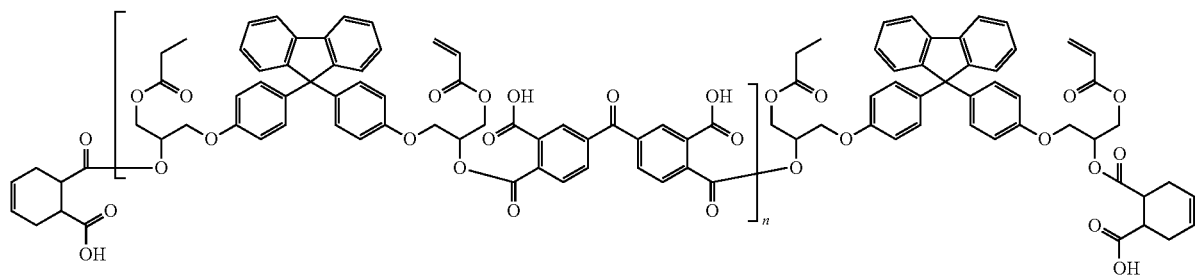

The polymerizable composition according to the invention and in particular the polymerizable composition comprising as component (d) at least one alkaline developable resin may contain further components (e) and/or (f), as mentioned in the following:

Colorants:

Pigments (e1) and/or dyes (e2) may be present. The pigments which can be comprised in the composition according to the present invention, including a pigmented color filter resist composition, are preferably processed pigments.

The red pigment (e1) comprises, for example, an anthraquinone type pigment alone, a diketopyrolopyrole type pigment alone, a mixture of them or a mixture consisting of at least one of them and a disazo type yellow pigment or an isoindoline type yellow pigment, in particular C. I. Pigment Red 177 alone, C. I. Pigment Red 254 alone, a mixture of C. I. Pigment Red 177 and C. I. Pigment Red 254 or a mixture consisting of at least one member of C. I. Pigment Red 177, C. I. Pigment Red 242 and C. I. Pigment Red 254, and C. I. Pigment Yellow 83 or C. I. Pigment Yellow 139 ("C.I." refers to the Color Index, known to the person skilled in the art and publicly available).

Further suitable examples for the pigment are C.I. Pigment Red 9, 97, 105, 122, 123, 144, 149, 168, 176, 179, 180, 185, 202, 207, 209, 214, 222, 244, 255, 264, 272 and C.I. Pigment Yellow 12, 13, 14, 17, 20, 24, 31, 53, 55, 93, 95, 109, 110, 128, 129, 138, 139, 150, 153, 154, 155, 166, 168, 185, 199, 213 and C.I. Pigment Orange 43 and 71. Examples of the dyes for red color are C. I. Solvent Red 25, 27, 30, 35, 49, 83, 89, 100, 122, 138, 149, 150, 160, 179, 218, 230, C. I. Direct Red 20, 37, 39, 44, and C. I. Acid Red 6, 8, 9, 13, 14, 18, 26, 27, 51, 52, 87, 88, 89, 92, 94, 97, 111, 114, 115, 134, 145, 151, 154, 180, 183, 184, 186, 198, C. I. Basic Red 12, 13, C. I. Disperse Red 5, 7, 13, 17 and 58. The Red dyes can be used in combination with yellow and/or orange dyes. The green pigment (e1) comprises for instance a halogenated phthalocyanine type pigment alone or its mixture with a bisazo type yellow pigment, an quinophthalone type yellow pigment or a metal complex, in particular C. I. Pigment Green 7 alone, C. I. Pigment Green 36 alone, C. I. Pigment 58 alone, or a mixture consisting of at least one member of C. I. Pigment Green 7, C. I. Pigment Green 36, Pigment Green 58 and C. I. Pigment Yellow 83, C. I. Pigment Yellow 138 or C. I. Pigment Yellow 150. Other suitable green pigments are C.I. Pigment Green 15, 25 and 37. Examples for suitable green dyes are C. I. Acid Green 3, 9, 16, C. I. Basic Green 1 and 4.

Examples for suitable blue pigments (e1) are phthalocyanine type pigments, used either alone or in combination with an dioxazine type violet pigment, for instance, C. I. Pigment Blue 15:6 alone, a combination of C. I. Pigment Blue 15:6 and C. I. Pigment Violet 23. Further examples for blue pigments are such of C. I. Pigment Blue 15:3, 15:4, 16, 22, 28 and 60. Other suitable pigments are C. I. Pigment Violet 14, 19, 23, 29, 32, 37, 177 and C. I. Orange 73.

The blue dye (e2) comprises, for example, a methine type dye, an anthraquinone type dye, an azo type dye, a metal complex azo type dye, a triarylmethane type dye or a phthalocyanine type dye.

Examples for suitable blue dyes are C. I. Solvent Blue 11, 25, 37, 45, 49, 68, 78, 94, C. I. Direct Blue 25, 86, 90, 108, C. I. Acid Blue 1, 3, 7, 9, 15, 83, 90, 103, 104, 158, 161, C. I. Basic Blue 1, 3, 7, 9, 25, 105, C. I. Disperse Blue 198 and Mordant Blue 1.

The pigment (e1) of the photopolymeric composition for black matrix preferably comprises at least one member selected from the group consisting of carbon black, titanium black, iron oxide, lactone, lactam and perylene. Preferred example is carbon black.

However, a mixture of other pigments which, in total, give the black appearance, can also be used. For example, also C. I. Pigment Black 1, 7, 31 and 32, Irgaphor® black S0100 (BASF SE), be used alone or in combination.

Other examples of the dyes (e2) used for color filter are C. I. Solvent Yellow 2, 5, 14, 15, 16, 19, 21, 33, 56, 62, 77, 83, 93, 162, 104, 105, 114, 129, 130, 162, C. I. Disperse Yellow 3, 4, 7, 31, 54, 61, 201, C. I. Direct Yellow 1, 11, 12, 28, C. I. Acid Yellow 1, 3, 11, 17, 23, 38, 40, 42, 76, 98, C. I. Basic Yellow 1, C. I. Solvent Violet 13, 33, 45, 46, C. I. Disperse Violet 22, 24, 26, 28, 31, C. I. Acid Violet 49, C. I. Basic Violet 2, 7, 10, C. I. Solvent Orange 1, 2, 5, 6, 37, 45, 62, 99, C. I. Acid Orange 1, 7, 8, 10, 20, 24, 28, 33, 56, 74, C. I. Direct Orange 1, C. I. Disperse Orange 5, C. I. Direct Brown 6, 58, 95, 101, 173, C. I. Acid Brown 14, C. I. Solvent Black 3, 5, 7, 27, 28, 29, 35, 45 and 46.

In some special cases of manufacturing color filters, complementary colors, yellow, magenta, cyan and optionally green, are used instead of red, green and blue. As yellow for this type of color filters, the abovementioned yellow pigments and dyes can be employed. Examples of the colorants suitable for magenta color are C. I. Pigment Red 122, 144, 146, 169, 177, C. I. Pigment Violet 19 and 23. Examples of cyan color are aluminum phthalocyanine pigments, titanium phthalocyanine pigments, cobalt phthalocyanine pigments, and tin phthalocyanine pigments.

The pigments (e1) in the color filter resist composition have preferably a mean particle diameter smaller than the wavelength of visible light (400 nm to 700 nm). Particularly preferred is a mean pigment diameter of <100 nm.

The concentration of the pigment (e1) in the total solid component (pigments of various colors and resin) is for example in the range of 5% to 80% by weight, in particular in the range of 20% to 65% by weight.

The concentration of the dye (e2) in the total solid component (dyes of various colors and resin) is for example in the range of 0.5% to 95% by weight, in particular in the range of 0.5% to 70% by weight.

If necessary, the pigments may be stabilized in the photosensitive composition by pretreatment of the pigments with a dispersant to improve the dispersion stability of the pigment in the liquid formulation. Suitable additives are described below.

Additives:

Additives are optional present such as dispersing agents (e4), surfactant, adhesion promoters, photosensitizer and the like.

It is preferred to apply a surface treatment to the pigments in order to make the pigment easy to disperse and to stabilize the resultant pigment dispersion. The surface treatment reagents are, for example, surfactants, polymeric dispersants, general texture improving agents, pigment derivatives and mixtures thereof. It is especially preferred when the colorant composition according to the invention comprises at least one polymeric dispersant and/or at least pigment derivative.

Suitable surfactants include anionic surfactants such as alkylbenzene- or alkylnahthalene-sulfonates, alkylsulfosuccinates or naphthalene formaldehyde sulfonates; cationic surfactants including, for example, quaternary salts such as benzyl tributyl ammonium chloride; or nonionic or amphoteric surfactants such as polyoxyethylene surfactants and alkyl- or amidopropyl betaines, respectively.

Illustrative examples of the surfactant include polyoxyethylene alkyl ethers such as polyoxyethylene lauryl ether, polyoxyethylene stearyl ether and polyoxyethylene oleyl ether; polyoxyethylene alkylphenyl ethers such as polyoxyethylene octylphenyl ether and polyoxyethylene nonylphenyl ether; polyethylene glycol diesters such as polyethylene glycol dilaurate and polyethylene glycol distearate; sorbitan fatty acid esters; fatty acid modified polyesters; tertiary amine modified polyurethanes; polyethyleneimines; those available under the trade names of KP (a product of Shin-Etsu Chemical Co., Ltd), Polyflow (a product of KYOEISHA CHEMICAL Co., Ltd), F-Top (a product of Tochem Products Co., Ltd), MEGAFAC (a product of Dainippon Ink & Chemicals, Inc.), Fluorad (a product of Sumitomo 3M Ltd), Asahi Guard and Surflon (products of Asahi Glass Co., Ltd); and the like.

These surfactants may be used alone or in admixture of two or more.

The surfactant is generally used in an amount of 50 parts or less by weight, preferably 0 to 30 parts by weight, based on 100 parts by weight of the colorant composition.

Polymeric dispersants (e4) include high molecular weight polymers with pigment affinic groups. Examples are: statistical co-polymers comprised from, for instance, styrene derivatives, (meth)acrylates and (meth)acrylamides, and such statistical co-polymers modified by post modification; block co-polymers and/or comb polymers comprised from, for instance, styrene derivatives, (meth)acrylates and (meth)acrylamides, and such block co-polymers and/or comb polymers modified by post modification; polyethylenimines, which for instance is crafted with polyesters; polyamines, which for instance is crafted with polyesters; and many kinds of (modified) polyurethanes.

Polymeric dispersants may also be employed. Suitable polymeric dispersants are, for example, BYK's DISPERBYK® 101, 115, 130, 140, 160, 161, 162, 163, 164, 166, 168, 169, 170, 171, 180, 182, 2000, 2001, 2009, 2020, 2025, 2050, 2090, 2091, 2095, 2096, 2150, BASF's EFKA® 4008, 4009, 4010, 4015, 4046, 4047, 4050, 4055, 4060, 4080, 4300, 4310, 4330, 4340, 4400, 4401, 4402, 4403, 4406, 4500, 4510, 4520, 4530, 4540, 4550, 4560, Ajinomoto Fine Techno's PB®711, 821, 822, 823, 824, 827, Lubrizol's SOLSPERSE® 1320, 13940, 17000, 20000, 21000, 24000, 26000, 27000, 28000, 31845, 32500, 32550, 32600, 33500, 34750, 36000, 36600, 37500, 39000, 41090, 44000, 53095 and combinations thereof.

It is preferred to use ® EFKA® 4046, 4047, 4060, 4300, 4310, 4330, 4340, DISPERBYK® 161, 162, 163, 164, 165, 166, 168, 169, 170, 2000, 2001, 2020, 2050, 2090, 2091, 2095, 2096, 2105, 2150, PB®711, 821, 822, 823, 824, 827, SOLSPERSE® 24000, 31845, 32500, 32550, 32600, 33500, 34750, 36000, 36600, 37500, 39000, 41090, 44000, 53095 and combinations thereof as dispersant.

Suitable texture improving agents are, for example, fatty acids such as stearic acid or behenic acid, and fatty amines such as laurylamine and stearylamine. In addition, fatty alcohols or ethoxylated fatty alcohols, polyols such as aliphatic 1,2-diols or epoxidized soy bean oil, waxes, resin acids and resin acid salts may be used for this purpose.

Suitable pigment derivatives are, for example, copper phthalocyanine derivatives such as BASF's EFKA® 6745, Lubrizol's SOLSPERSE® 5000, 12000, BYK's SYNERGIST 2100 and azo derivatives such as EFKA® 6750, SOLSPERSE® 22000 and SYNERGIST 2105.

The above mentioned dispersants and surfactants for pigments are for example employed in compositions of the present invention which are used as resist formulations, in particular in color filter formulations.

Subject of the invention also is a photopolymerizable composition as described above as further additive comprising a dispersant or a mixture of dispersants as well as a photopolymerizable composition as described above as further additive comprising a pigment, a mixture of pigments, a dye, a mixture of dyes or a mixture of at least one dye and at least one pigment.

In the invention, the content of the dispersing agent is preferably from 1 to 80% by mass, more preferably from 5 to 70% by mass, even more preferably from 10 to 60% by mass, based on the mass of the pigment.

Adhesion Improving Agent:

The curable composition of the invention may contain an adhesion improving agent for increasing adhesion to a hard surface, such as of a support. The adhesion improving agent may be a silane coupling agent, a titanium coupling agent or the like.

Photosensitizer:

Photopolymerization can also be accelerated by adding further photosensitizers or coinitiators which shift or broaden the spectral sensitivity. These are, in particular, aromatic compounds, for example benzophenone and derivatives thereof, thioxanthone and derivatives thereof, anthraquinone and derivatives thereof, coumarin and phenothiazine and derivatives thereof, and also 3-(aroylmethylene)thiazolines, rhodanine, camphorquinone, but also eosine, rhodamine, erythrosine, xanthene, thioxanthene, acridine, e.g. 9-phenylacridine, 1,7-bis(9-acridinyl)heptane, 1,5-bis(9-acridinyl)pentane, cyanine and merocyanine dyes.

Specific examples of such compounds are

1. Thioxanthones

Thioxanthone, 2-isopropylthioxanthone, 2-chlorothioxanthone, 1-chloro-4-propoxythioxanthone, 2-dodecylthioxanthone, 2,4-diethylthioxanthone, 2,4-dimethylthioxanthone, 1-methoxycarbonylthioxanthone, 2-ethoxycarbonylthioxanthone, 3-(2-methoxyethoxycarbonyl)-thioxanthone, 4-butoxycarbonylthioxanthone, 3-butoxycarbonyl-7-methylthioxanthone, 1-cyano-3chlorothioxanthone, 1-ethoxycarbonyl-3-chlorothioxanthone, 1-ethoxycarbonyl-3-ethoxythioxanthone, 1-ethoxycarbonyl-3-aminothioxanthone, 1-ethoxycarbonyl-3-phenylsulfuryl-thioxanthone, 3,4-di-[2-(2-methoxyethoxy)ethoxycarbonyl]-thioxanthone, 1,3-dimethyl-2-hydroxy-9Hthioxanthen-9-one 2-ethylhexylether, 1-ethoxycarbonyl-3-(1-methyl-1-morpholinoethyl)-thioxanthone, 2-methyl-6-dimethoxymethyl-thioxanthone, 2-methyl-6-(1,1-dimethoxybenzyl)-thioxanthone, 2-morpholinomethylthioxanthone, 2-methyl-6-morpholinomethylthioxanthone, N-allylthioxanthone-3,4-dicarboximide, N-octylthioxanthone-3,4-dicarboximide, N-(1,1,3,3-tetramethylbutyl)thioxanthone-3,4-dicarboximide, 1-phenoxythioxanthone, 6-ethoxycarbonyl-2methoxythioxanthone, 6-ethoxycarbonyl-2-methylthioxanthone, thioxanthone-2-carboxylic acid polyethyleneglycol ester, 2-hydroxy-3-(3,4-dimethyl-9-oxo-9H-thioxanthon-2-yloxy)-N,N,N-trimethyl-1-propanaminium chloride;

2. Benzophenones benzophenone, 4-phenyl benzophenone, 4-methoxy benzophenone, 4,4'-dimethoxy benzophenone, 4,4'-dimethyl benzophenone, 4,4'-dichlorobenzophenone 4,4'-bis(dimethylamino)benzophenone, 4,4'-bis(diethylamino)benzophenone, 4,4'-bis(methylethylamino)benzophenone, 4,4'-bis(p-isopropylphenoxy)benzophenone, 4-methyl benzophenone, 2,4,6-trimethylbenzophenone, 4-(4-methylthiophenyl)-benzophenone, 3,3'-dimethyl-4-methoxy benzophenone, methyl-2-benzoylbenzoate, 4-(2-hydroxyethylthio)-benzophenone, 4-(4-tolylthio)benzophenone, 1-[4-(4-benzoylphenylsulfanyl)phenyl]-2-methyl-2-(toluene-4-sulfonyl)-propan-1-one, 4-benzoyl-N,N,N-trimethylbenzenemethanaminium chloride, 2-hydroxy-3-(4-benzoylphenoxy)-N,N,N-trimethyl-1-propanaminium chloride monohydrate, 4-(13-acryloyl1,4,7,10,13-pentaoxatridecyl)benzophenone, 4-benzoyl-N,N-dimethyl-N-[2-(1-oxo-2-propenyl)oxy]ethyl-benzenemethanaminium chloride;

3. Coumarins

Coumarin 1, Coumarin 2, Coumarin 6, Coumarin 7, Coumarin 30, Coumarin 102, Coumarin 106, Coumarin 138, Coumarin 152, Coumarin 153, Coumarin 307, Coumarin 314, Coumarin 314T, Coumarin 334, Coumarin 337, Coumarin 500, 3-benzoyl coumarin, 3-benzoyl-7-methoxycoumarin, 3-benzoyl-5,7-dimethoxycoumarin, 3-benzoyl-5,7-dipropoxycoumarin, 3-benzoyl-6,8-dichlorocoumarin, 3-benzoyl-6-chloro-coumarin, 3,3'-carbonyl-bis[5,7-di(propoxy)coumarin], 3,3'-carbonyl-bis(7-methoxycoumarin), 3,3'-carbonyl-bis(7-diethylamino-coumarin), 3-isobutyroylcoumarin, 3-benzoyl-5,7-dimethoxy-coumarin, 3-benzoyl-5,7-diethoxy-coumarin, 3-benzoyl-5,7-dibutoxycoumarin, 3-benzoyl-5,7-di(methoxyethoxy)-coumarin, 3-benzoyl-5,7-di(allyloxy)coumarin, 3-benzoyl-7-dimethylaminocoumarin, 3-benzoyl-7-diethylaminocoumarin, 3-isobutyroyl-7-dimethylaminocoumarin, 5,7-dimethoxy-3-(1-naphthoyl)-coumarin, 5,7-diethoxy-3-(1-naphthoyl)-coumarin, 3-benzoylbenzo[f]coumarin, 7-diethylamino-3-thienoylcoumarin, 3-(4-cyanobenzoyl)-5,7-dimethoxycoumarin, 3-(4-cyanobenzoyl)-5,7-dipropoxycoumarin, 7-dimethylamino-3-phenylcoumarin, 7-diethylamino-3-phenylcoumarin, the coumarin derivatives disclosed in JP 09-179299-A and JP 09-325209-A, for example 7-[{4-chloro-6-(diethylamino)-S-triazine-2-yl}amino]-3-phenylcoumarin;

4. 3-(aroyl methylene)-thiazolines 3-methyl-2-benzoylmethylene-β-naphthothiazoline, 3-methyl-2-benzoylmethylene-benzothiazoline, 3-ethyl-2-propionylmethylene-β-naphthothiazoline;

5. Rhodanines 4-dimethylaminobenzalrhodanine, 4-diethylaminobenzalrhodanine, 3-ethyl-5-(3-octyl-2-benzothiazolinylidene)-rhodanine, the rhodanine derivatives, formulae [1], [2], [7], disclosed in JP 08-305019A;

6. Other Compounds acetophenone, 3-methoxyacetophenone, 4-phenylacetophenone, benzil, 4,4'-bis(dimethylamino)benzil, 2-acetylnaphthalene, 2-naphthaldehyde, dansyl acid derivatives, 9,10-anthraquinone, anthracene, pyrene, aminopyrene, perylene, phenanthrene, phenanthrenequinone, 9-fluorenone, dibenzosuberone, curcumin, xanthone, thio michler's ketone, α-(4-dimethylaminobenzylidene) ketones, e.g. 2,5-bis(4-diethylaminobenzylidene)cyclopentanone, 2-(4-dimethylamino-benzylidene)-indan-1-one, 3-(4-dimethylamino-phenyl)-1-indan-5-yl-propenone, 3-phenylthiophthalimide, N-methyl-3,5-di(ethylthio)-phthalimide, N-methyl-3,5-di(ethylthio)phthalimide, phenothiazine, methylphenothiazine, amines, e.g. N-phenylglycine, ethyl 4-dimethylaminobenzoate, butoxyethyl 4-dimethylaminobenzoate, 4-dimethylaminoacetophenone, triethanolamine, methyldiethanolamine, dimethylaminoethanol, 2-(dimethylamino)ethyl benzoate, poly(propylenegylcol)-4-(dimethylamino) benzoate.

A photosensitizer may be selected from the group consisting of benzophenone and its derivatives, thioxanthone and its derivatives, anthraquinone and its derivatives, or coumarin and its derivatives.

Accelerator:

To accelerate the photopolymerization, it is possible to add amines, for example triethanolamine, N-methyldiethanolamine, ethyl-p-dimethylaminobenzoate, 2-(dimethylamino)ethyl benzoate, 2-ethylhexyl-p-dimethylaminobenzoate, octyl-para-N,N-dimethylaminobenzoate, N-(2-hydroxyethyl)-N-methyl-para-toluidine or Michler's ketone. The action of the amines can be intensified by the addition of aromatic ketones of the benzophenone type. Examples of amines which can be used as oxygen scavengers are substituted N,N-dialkylanilines, as are described in EP339841. Other accelerators, coinitiators and autoxidizers are thiols, thioethers, disulfides, phosphonium salts, phosphine oxides or phosphines, as described, for example, in EP438123, in GB2180358 and in JP Kokai Hei 6-68309.

The choice of additive(s) is made depending on the field of application and on properties required for this field. The additives described above are customary in the art and accordingly are added in amounts which are usual in the respective application.

Thermal Inhibitor:

Thermal inhibitors are intended to prevent premature polymerization, examples being hydroquinone, hydroquinone derivatives, p-methoxyphenol, β-naphthol or sterically hindered phenols, such as 2,6-di-tert-butyl-p-cresol. In order to increase the stability on storage in the dark it is possible, for example, to use copper compounds, such as copper naphthenate, stearate or octoate, phosphorus compounds, for example triphenylphosphine, tributylphosphine, triethylphosphine, triphenyl phosphate or tribenzyl phosphate, quaternary ammonium compounds, for example tetramethylammonium chloride or trimethylbenzylammonium chloride, or hydroxylamine derivatives, for example N-diethylhydroxylamine. To exclude atmospheric oxygen during the polymerization it is possible to add paraffin or similar wax-like substances which, being of inadequate solubility in the polymer, migrate to the surface in the beginning of polymerization and form a transparent surface layer which prevents the ingress of air. It is also possible to apply an oxygen-impermeable layer. Light stabilizers which can be added in a small quantity are UV absorbers, for example those of the hydroxyphenylbenzotriazole, hydroxyphenylbenzophenone, oxalamide or hydroxyphenyl-s-triazine type. These compounds can be used individually or in mixtures, with or without sterically hindered amines (HALS).

Solvents:

Examples of suitable solvents are ketones, ethers and esters, such as methyl ethyl ketone, isobutyl methyl ketone, cyclopentanone, cyclohexanone, N-methylpyrrolidone, dioxane, tetrahydrofuran, ethylene glycol monomethyl ether, ethylene glycol monoethyl ether, ethylene glycol monopropyl ether, ethylene glycol monobutyl ether, ethylene glycol dimethyl ether, ethylene glycol diethyl ether, ethylene glycol dipropyl ether, propylene glycol monomethyl ether, propylene glycol monoethyl ether, propylene glycol monopropyl ether, propylene glycol monobutyl ether, propylene glycol dimethyl ether, propylene glycol diethyl ether, propylene glycol dipropyl ether, diethylene glycol monomethyl ether, diethylene glycol monoethyl ether, diethylene glycol dimethyl ether, diethylene glycol diethyl ether, ethylene glycol monomethyl ether acetate, ethylene glycol monoethyl ether acetate, ethylene glycol monopropyl ether acetate, ethylene glycol monobutyl ether acetate, propylene glycol monomethyl ether acetate, propylene glycol monoethyl ether acetate, propylene glycol monopropyl ether acetate, 2-methoxybutyl acetate, 3-methoxybutyl acetate, 4-methoxybutyl acetate, 2-methyl-3-methoxybutyl acetate, 3-methyl-3-methoxybutyl acetate, 3-ethyl-3-methoxybutyl acetate, 2-ethoxybutyl acetate, 4-ethoxybutyl acetate, 4-propoxybutyl acetate, 2-methoxypentyl acetate, 3-methoxypentyl acetate, 4-methoxypentyl acetate, 2-methyl-3-methoxypentyl acetate, 3-methyl-3-methoxypentyl acetate, 3-methyl-4-methoxypentyl acetate, 4-methyl-4-methoxypentyl acetate, ethyl acetate, n-butyl acetate, ethyl propionate, propyl propionate, butyl propionate, ethyl 3-ethoxypropionate, methyl 3-methoxypropionate, 2-heptanone, 2-pentanone, and ethyl lactate.

Hybrid System:

The compositions according to this invention can comprise additionally a crosslinking agent which is activated by an acid or a base, for example as described in JP 10 221843-A, and a compound which generates acid or base thermally or by actinic radiation and which activates a crosslinking reaction. Use is made, in addition to the free-radical hardeners, of cationic photo or thermal initiators such as sulfonium-, phosphonium- or iodonium salts, for example IRGACURE® 250, San-Aid SI series, SI-60L, SI-80L, SI-100L, SI-110L, SI-145, SI-150, SI-160, SI-180L produced by Sanshin Chemical, cyclopentadienyl-arene-iron (II) complex salts, for example ($\eta^6$-iso-propylbenzene)($\eta^5$-cyclopentadienyl)iron(II) hexafluorophosphate, as well as oxime sulfonic acid esters, for example described in EP 780729. Also pyridinium and (iso)quinolinium salts as described e.g. in EP 497531 and EP 441232 may be used in combination with the new compounds of formula (I). Examples of bases are imidazole and its derivatives for example Curezole OR series and CN series provided by Shikoku Chemicals.

The crosslinking agents which can be activated by acid or base include compounds having epoxy or oxetane groups. There may be used a solid or liquid known epoxy or oxetane compound and said compound is used depending on required characteristics. A preferred epoxy resin is a bisphenol S type epoxy resin such as BPS-200 produced by Nippon Kayaku Co., Ltd., EPX-30 produced by ACR Co., Epiculon EXA-1514 produced by Dainippon Ink & Chemicals Inc., etc.; a bisphenol A type epoxy resin such as Epiculon N-3050, N-7050, N-9050 produced by Dainippon Ink & Chemicals Inc., XAC-5005, GT-7004, 6484T, 6099; a bisphenol F type epoxy resin such as YDF-2004, YDF2007 produced by Tohto Kasei Co., etc.; a bisphenol fluorene type epoxy resin such as OGSOL PG, PG-100, EG, EG-210 produced by Osaka Gas Chemicals; a diglycidyl phthalate resin such as Blemmer DGT produced by Nippon Oil and Fats Co., Ltd., etc.; a heterocyclic epoxy resin such as TEPIC produced by Nissan Chemical Industries, Ltd., Araldite PT810 produced by Ciba Specialty Chemicals Inc., etc.; a bixylenol type epoxy resin such as YX-4000 produced by Yuka Shell Co., etc.; a biphenol type epoxy resin such as YL-6056 produced by Yuka Shell Co., etc.; a tetraglycidyl xylenoylethane resin such as ZX-1063 produced by Tohto Kasei Co., etc.; a novolak type epoxy resin such as EPPN- 201, EOCN-103, EOCN-1020, EOCN-1025 and BRRN produced by Nippon Kayaku Co., Ltd., ECN-278, ECN-292 and ECN-299 produced by Asahi Chemical Industry Co., Ltd., GY-1180, ECN-1273 and ECN-1299 produced by Ciba Specialty Chemicals Inc., YDCN-220L, YDCN-220HH, YDCN-702, YDCN-704, YDPN-601 and YDPN-602 produced by Tohto Kasei Co., Epiculon-673, N-680, N-695, N-770 and N-775 produced by Dainippon Ink & Chemicals Inc., etc.; a novolak type epoxy resin of bisphenol A such as EPX-8001, EPX-8002, EPPX-8060 and EPPX-8061 produced by Asahi Chemical Industry Co., Ltd., Epiculon N-880 produced by Dainippon Ink & Chemicals Inc., etc.; a chelate type epoxy resin such as EPX-49-69 and EPX-49-30 produced by Asahi Denka Kogyo K.K., etc.; a glyoxal type epoxy resin such as YDG-414 produced by Tohto Kasei Co., etc.; an amino group-containing epoxy resin such as YH-1402 and ST-110 produced by Tohto Kasei Co., YL-931 and YL-933 produced by Yuka Shell Co., etc.; a rubber-modified epoxy resin such as Epiculon TSR-601 produced by Dainippon Ink & Chemicals Inc., EPX-84-2 and EPX-4061 produced by Asahi Denka Kogyo K.K., etc.; a dicyclopentadiene phenolic type epoxy resin such as DCE-400 produced by Sanyo-Kokusaku Pulp Co., Ltd., etc.; a silicone-modified epoxy resin such as X-1359 produced by Asahi Denka Kogyo K.K., etc.; an e-caprolactone-modified epoxy resin such as Plaque G-402 and G-710 produced by Dicel Chemical Industries, Ltd., etc. and others. Further, partially esterified compounds of these epoxy compounds (e.g. esterified by (meth)acrylates) can be used in combination. Examples of oxetane compounds are 3-ethyl-3-hydroxymethyloxetane (oxetane alcohol), 2-ethylhexyloxetane, xylene bisoxetane, 3-ethyl-3[[(3-ethyloxetane-3-yl) methoxy]methyl]oxetane (Aron Oxetane series) provided by Toagosei.

The polymerizable compositions according to the invention, comprising at least one compound of the formula (I) are especially suitable for the following applications:

resists to manufacture color filters for a variety of display applications,
spacers for LCD,
overcoat layers for color filters or LCD,
sealants for LCD and OLED,
insulation/passivation layers for LCD, OLED, touch panels and flexible displays.
bank/pixel definition layer of OLED
insulation for metal wiring/transparent conductive film for touch panel
coating for touch panel such as anti-fingerprint, hard coat and optical coat
decorative ink for touch panel
protective film for touch panel
etching resists for touch panel The polymerizable compositions according to the invention, comprising at least one compound of the formula (I) are for example also suitable for the following applications:

optical films for a variety of display applications, such as hard coats, anti-reflective films, anti-glare films, retardation films, NIR absorbing films, prism sheets, brightness enhancement films and the like,
other resists, photosensitive compositions or thermosetting compositions to generate structures or layers in the manufacturing processes of plasma-display panels, electroluminescence displays, organic light-emitting diode displays (OLED), touch panels, flexible displays and LCD,
solder resists,
photoresist materials used for forming dielectric layers in a sequential build-up layer of a printed circuit board,
photoresists for electronics, electroplating resists, etch resists, both liquid and dry films,
anisotropy conducting adhesive, (An anisotropic conductive adhesive contains conductive particles dispersed in a resin composition and can be used for electrical joining of electronic or electric parts. They can be employed to join fine circuits, for example a liquid crystal display (LCD) and a tape carrier package (TCP) or a TCP and a printed circuit board (PCB), and the like.),
polymerization to form oligomers, co-oligomers, polymers and copolymers, for example, random block, multi-block, star or gradient copolymers,
controlled degradation of polymers and controlled build-up of the molecular weight or crosslinking,
coating agent for buildings, building materials, automobile parts, electrical instruments, precision instrument, etc.,
pressure-sensitive adhesive optical films including an optical film and a pressure-sensitive adhesive layer, e.g. for LCD and organic electroluminescence (EL) displays,
adhesives and printed circuit boards having adhesive layer, e.g. used as automobile parts, electrical instruments and the like,
dental materials,
sealer for building and building materials.

The invention further relates to the use of the photoresist composition to manufacture color filters for a variety of display applications and for image sensors such as charge coupled device (CCD) and complementary metal-oxide semiconductor (CMOS), spacers for LCD, overcoat layer for color filter and LCD, sealant for LCD and OLED, optical films for a variety of display applications, insulation/passivation layer for LCD, organic light-emitting diode displays (OLED), touch panels and flexible displays, bank/pixel definition layer of OLED, insulation for metal wiring/transparent conductive film for touch panel, coating for touch panel such as anti-fingerprint, hard coat and optical coat, decorative ink for touch panel, protective film for touch panel, etching resists for touch panel, resists or photosensitive compositions to generate structures or layers in the manufacturing processes of plasma-display panels, electroluminescence displays OLED, touch panels, flexible displays and LCD, solder resists, as a photoresist material used for forming dielectric layers in a sequential build-up layer of a printed circuit board.

The compositions according to the invention are particularly suitable for the production of color filters or color mosaic systems, such as described, for example, in EP 320 264. The color filters can be used, for example, for flat panel display technology such as LCD, electroluminescent display and plasma display, for image sensors such as CCD and CMOS, and the like.

Subject of the invention also is a color filter.

The color filters usually are prepared by forming red, green and blue pixels and optionally a black matrix on a glass substrate. In these processes photocurable compositions according to the invention can be employed. A particularly preferred method of use comprises adding of the coloring matters, dyes and pigments of red, green and blue colors to the light-sensitive resin composition of the present invention, coating of the substrate with the composition, drying of the coating with a short heat treatment, patternwise exposure of the coating (i.e. through a suitable mask) to actinic radiation and subsequent development of the pattern in a suitable aqueous alkaline developer solution and a heat treatment. Thus, by subsequently applying a red, green, blue and black pigmented coating, in any desired order, on top of each other with this process a color filter layer with red, green and blue color pixels and black matrix can be produced.

At the photolithography, suitable radiation from about 150 nm to 600 nm, for example 190-600 nm (UV-VIS region) is chosen, for example, in sunlight or light from artificial light sources. Consequently, a large number of very different types of light sources are employed. Both point sources and arrays ("lamp carpets") are suitable. Examples are carbon arc lamps, xenon arc lamps, super high-, high-, medium- and low-pressure mercury lamps, possibly with metal halide dopes (metal-halogen lamps), microwave-stimulated metal vapor lamps, excimer lamps, superactinic fluorescent tubes, fluorescent lamps, argon incandescent lamps, electronic flashlights, photographic flood lamps, light emitting diodes (LED), electron beams and X-rays. The distance between the lamp and the substrate to be exposed in accordance with the invention may vary depending on the intended application and the type and output of lamp, and may be, for example, from 2 cm to 150 cm. Laser light sources, for example excimer lasers, such as KrF lasers for example at 248 nm, ArF-lasers for example at 193 nm and $F_2$ lasers for exposure at 157 nm are also suitable. Lasers in the visible region can also be employed.

In addition to a process in which the light-sensitive resin composition is coated on a substrate and dried, the light-sensitive resin composition of the present invention can be used as well for a layer transfer material. That is, the light-sensitive resin composition is layer-wise provided directly on a temporary support, preferably on a polyethylene terephthalate film, or on a polyethylene terephthalate film on which an oxygen-shielding layer and a peeling layer or the peeling layer and the oxygen-shielding layer are provided. Usually, a removable cover sheet made of a synthetic resin is laminated thereon for a protection in handling. Further, there can be applied as well a layer structure in which an alkali soluble thermoplastic resin layer and an intermediate layer are provided on a temporary support and further a light-sensitive resin composition layer is provided thereon (JP 5-173320-A).

The above cover sheet is removed in use and the light-sensitive resin composition layer is laminated on a permanent support. Subsequently, peeling is carried out between those layer and a temporary support when an oxygen-shielding layer and a peeling layer are provided, between the peeling layer and the oxygen-shielding layer when the peeling layer and the oxygen-shielding layer are provided, and between the temporary support and the light-sensitive resin composition layer when either the peeling layer or the oxygen-shielding layer is not provided, and the temporary support is removed.

The developer solution can be used in all forms known to the person skilled in the art, for example in form of a bath solution, puddle, or a spraying solution. In order to remove the non-cured portion of the light-sensitive resin composition layer, there can be combined the methods such as rubbing with a rotary brush and rubbing with a wet sponge. Usually, the temperature of the developing solution is preferably at and around room temperature to 40° C. The developing time is changeable according to the specific kind of the light-sensitive resin composition, the alkalinity and temperature of the developing solution, and the kind and concentration of the organic solvent in the case where it is added. Usually, it is 10 seconds to 2 minutes. It is possible to put a rinsing step after the development processing.

A final heat treatment is preferably carried out after the development processing. Accordingly, a support having a layer which is photopolymerized by exposing (hereinafter referred to as a photocured layer) is heated in an electric furnace and a drier, or the photocured layer is irradiated with an infrared lamp or heated on a hot plate. The heating temperature and time depend on the composition used and the thickness of the formed layer. In general, heating is preferably applied at about 120° C. to about 250° C., for about 2 to about 60 minutes.

Examples for color filter resists, the composition of such resists and the processing conditions are given by T. Kudo et al., Jpn. J. Appl. Phys. Vol. 37 (1998) 3594; T. Kudo et al., J. Photopolym. Sci. Technol. Vol 9 (1996) 109; K. Kobayashi, Solid State Technol. November 1992, p. S15-S18; U.S. Pat. Nos. 5,368,976; 5,800,952; 5,882,843; 5,879, 855; 5,866,298; 5,863,678; JP 06-230212-A; EP320264; JP 09-269410-A; JP 10-221843-A; JP 01-090516-A; JP 10-171119-A, U.S. Pat. Nos. 5,821,016, 5,847,015, 5,882, 843, 5,719,008, EP881541, or EP902327.

Instead of forming a black matrix using a photosensitive composition and patterning the black photosensitive composition photolithographically by patternwise exposure to form the black pattern separating the red green and blue colored areas on the transparent substrate it is alternatively possible to use an inorganic black matrix. Such inorganic black matrix can be formed from deposited (i.e. sputtered) metal (i.e. chromium) film on the transparent substrate by a suitable imaging process, for example utilizing photolithographic patterning by means of an etch resist, etching the inorganic layer in the areas not protected by the etch resist and then removing the remaining etch resist.

The photosensitive or thermosetting composition of the present invention can also be used to form such overcoat layers, because a cured film of the composition is excellent in flatness, hardness, chemical and thermal resistance, transparency especially in a visible region, adhesion to a substrate, and suitability for forming a transparent conductive film, e.g., an ITO film, thereon. In the production of a protective layer, there has been a demand that unnecessary parts of the protective layer, for example on scribing lines for cutting the substrate and on bonding pads of solid image sensors should be removed from the substrate as described in JP57-42009-A, JP1-130103-A and JP1-134306-A. In this regard, it is difficult to selectively form a protective layer with good precision using the above-mentioned thermosetting resins. The photosensitive composition, however, allows to easily remove the unnecessary parts of the protective layer by photolithography.

The photosensitive compositions according to the invention can further be used for manufacturing spacers, which control a cell gap of the liquid crystal part in liquid crystal display panels. Since the properties of light transmitted or reflected through the liquid crystal layer in a liquid crystal display are dependent on the cell gap, the thickness accuracy and uniformity over the pixel array are critical parameters for the performance of the liquid crystal display unit. By using photolithographic process, columns of a resin can be formed as spacers in the region between the pixel array region and the counter electrode to form a prescribed cell gap. Photosensitive materials having adhesive properties with photolithography are commonly used, for instance, in the manufacturing process of color filters. This method is advantageous compared with the conventional method using spacer beads in the points that location, number and height of the spacers may be controlled freely. In a color liquid crystal display panel, such spacers are formed in the non-imaging area under black matrix of color filter elements. Therefore, the spacers formed using photosensitive compositions do not decrease brightness and optical aperture. A transparent column spacer has been widely used in the LCD technology, but the transparent spacer disturbs polarized light reducing the contrast ratio. One of a possible solution is to mix with a black colorant not to scatter but to absorb the polarized light, i.e. a black column spacer. Black column spacer is also used in the LCD technology. In case of black column spacer, one or more further black colorants or mixture of other color colorants described above colorant (e1)(e2) is used.

Photosensitive compositions for producing protective layer with spacers for color filters are disclosed in JP 2000-81701-A and dry film type photoresists for spacer materials are also disclosed in JP 11-174459-A and JP 11-174464-A. As described in the documents, the photosensitive compositions, liquid and dry film photoresists, are comprising at least an alkaline or acid soluble binder polymer, a radically polymerizable monomer, and a curing promoter. In some cases, thermally crosslinkable components such as epoxide and carboxylic acid may additionally be included.

The steps to form spacers using a photosensitive composition are as follows:
a photosensitive composition is applied to the substrate, for instance a color filter panel and after the substrate is pre-baked, it is exposed to light through a mask. Then, the substrate is developed with a developer and patterned to form the desired spacers. When the composition contains some thermosetting components, usually a post-baking is carried out to thermally cure the composition.

The photocurable compositions according to the invention are suitable for producing spacers for liquid crystal displays (as described above).

The compositions according to the invention are also suitable for manufacturing interlayer insulating layers or dielectric layers in a liquid crystal display, and more particularly in specific LCD structures such as color filter on array type and reflection type LCDs.

The compositions according to the invention are also suitable for insulative electrical machinery to coat the windings and seal the stator windings of electrical inductive devices, such as motors, are wound with magnet wire having enamel or other insulative coating from the environment.

The photosensitive thermosetting resin composition and a method of forming a solder resist pattern by the use thereof, and more particularly relates to a novel photosensitive thermosetting resin composition useful as materials for the production of printed circuit boards, the precision fabrication of metallic articles, the etching of glass and stone articles, the relief of plastic articles, and the preparation of printing plates and particularly useful as a solder resist for printed circuit boards and to a method of forming a solder resist pattern by the steps of exposing a layer of the resin composition selectively to an actinic ray through a photomask having a pattern and developing the unexposed part of the layer.

The solder resist is a substance which is used during the soldering of a given part to a printed circuit board for the purpose of preventing molten solder from adhering to irrelevant portions and protecting circuites. It is, therefore, required to possess such properties as high adhesion, insulation resistance, resistance to soldering temperature, resistance to solvents, resistance to solvents, resistance to alkalis, resistance to acids, and resistance to plating. Subject of the invention also is a solder resist comprising a composition as described above.

Preferred is the use of the compositions, comprising thermosetting elements described as compound according to the invention, in an image-forming process, e.g. a process for the preparation of solder masks, wherein
1.) the components of the composition as described above are mixed,
2.) the resulting composition is applied to the substrate ("coating of substrate"),
3.) the solvent, if present, is evaporated, at elevated temperature, e.g. at a temperature between 80-90° C.,
4.) the coated substrate is patternwise exposed to electromagnetic radiation through a negative mask (thereby initiating the reaction of the acrylate)
5.) the irradiated sample is developed, by washing with aqueous alkaline solution and thereby removing the uncured areas and
6.) the sample is thermally cured, e.g. at a temperature of about 150° C.

This process is another object of the invention.

The heating step (6) usually is carried out at temperature of at least 100° C. and not more than 200° C., preferably at temperatures of 130-170° C., e.g. at 150° C.

The photosensitive or thermosetting coating composition of the present invention can also be used to form such coating layers, which is required adherence property, thermal resistance, flexibility, adhesiveness, electrical insulating property and humidity resistance for building, building materials, automobile parts, electrical instrument, precision instrument and the like.

The compositions according to the invention are also suitable for dental materials are also disclosed in U.S. Pat. No. 6,410,612 and JP60011409. As described in the documents, the photosensitive or thermosetting compositions comprise some kind of acrylic resin and polymerization initiator.

An anisotropic conductive adhesive is a circuit connecting material, in which conductive particles are dispersed in an insulating adhesive component, which adheres mechanically circuits disposed in the opposite direction, and simultaneously interposes a conductive particle between the circuit electrodes to establish an electrical connection. As an insulating adhesive component, a thermoplastic resin and a thermosetting resin are usable, and the thermosetting resin is more preferably used in terms of connection reliability.

In case of employing the thermosetting resin as an adhesive component, a connection is made by interposing an anisotropic conductive adhesive between connected to be members, which is then heat-compressed.

The invention, as described above, provides compositions for producing pigmented and non-pigmented paints and varnishes, powder coatings, printing inks, printing plates, adhesives, dental compositions. Photoresists for electronics like electroplating resist, etch resist, both liquid and dry films, solder resist, as resists to manufacture color filters for a variety of display applications or to generate structures in the manufacturing processes of plasma-display panels (c.g. barrier rib, phosphor layer, electrode), electroluminescence, displays and LCD) (e.g. Interlayer insulating layer, spacers, microlens array), as composition for encapsulating electrical and electronic components, for producing magnetic recording materials, micromechanical parts, waveguides, optical switches, plating masks, etch masks, color proofing systems, glass fiber cable coatings, screen printing stencils, for producing three-dimensional objects by means of stereo-lithography, and as image recording material, especially for holographic recordings, microelectronic circuits, decolorizing materials, decolorizing materials for image recording materials, for image recording materials using microcapsules.

Interesting a process for the thermal polymerization of a composition containing ethylenically unsaturated double bonds, which comprises heating a composition as described above.

In particular a process, which comprises heating a composition as described above in the range from 80° C. to 260° C.

Subject of the invention also is the use of a composition as described above as resists to manufacture color filters, spacers for LCD, overcoat layers for color filter and LCD, sealants for LCD and OLED, optical films, anisotropy conducting adhesives for LCD, insulation/passivation layers for LCD, organic light-emitting diode displays (OLED), touch panels and flexible displays, bank/pixel definition layer of OLED, insulation for metal wiring/transparent conductive film for touch panel, coating for touch panel such as anti-fingerprint, hard coat and optical coat, decorative ink for touch panel, protective film for touch panel, etching resists for touch panel, resists or photosensitive compositions to generate structures or layers in the manufacturing processes of plasma-display panels, electroluminescence displays, organic light-emitting diode displays (OLED), touch panels, flexible displays and LCD, solder resists, as a photoresist material used for forming dielectric layers in a sequential build-up layer of a printed circuit board.

The compounds of the general formula I have at least one of the following advantageous properties:
  enabling of reduction of curing time;
  enabling of reduction of curing temperature;
  thermal stability,
  high compatibility with the composition to be polymerized,
  high cross-linking density
  high curing speed
  low shrinkage
  storage stability and
  long pot-life.

The examples which follow illustrate the invention in more detail, without restricting the scope said examples only. Parts and percentages are, as in the remainder of the description and in the claims, by weight, unless stated otherwise. Where alkyl radicals having more than three carbon atoms are referred to in the examples without any mention of specific isomers, the n-isomers are meant in each case.

PREPARATION EXAMPLES

Preparation of OS1OS1 is prepared as described in the following scheme.

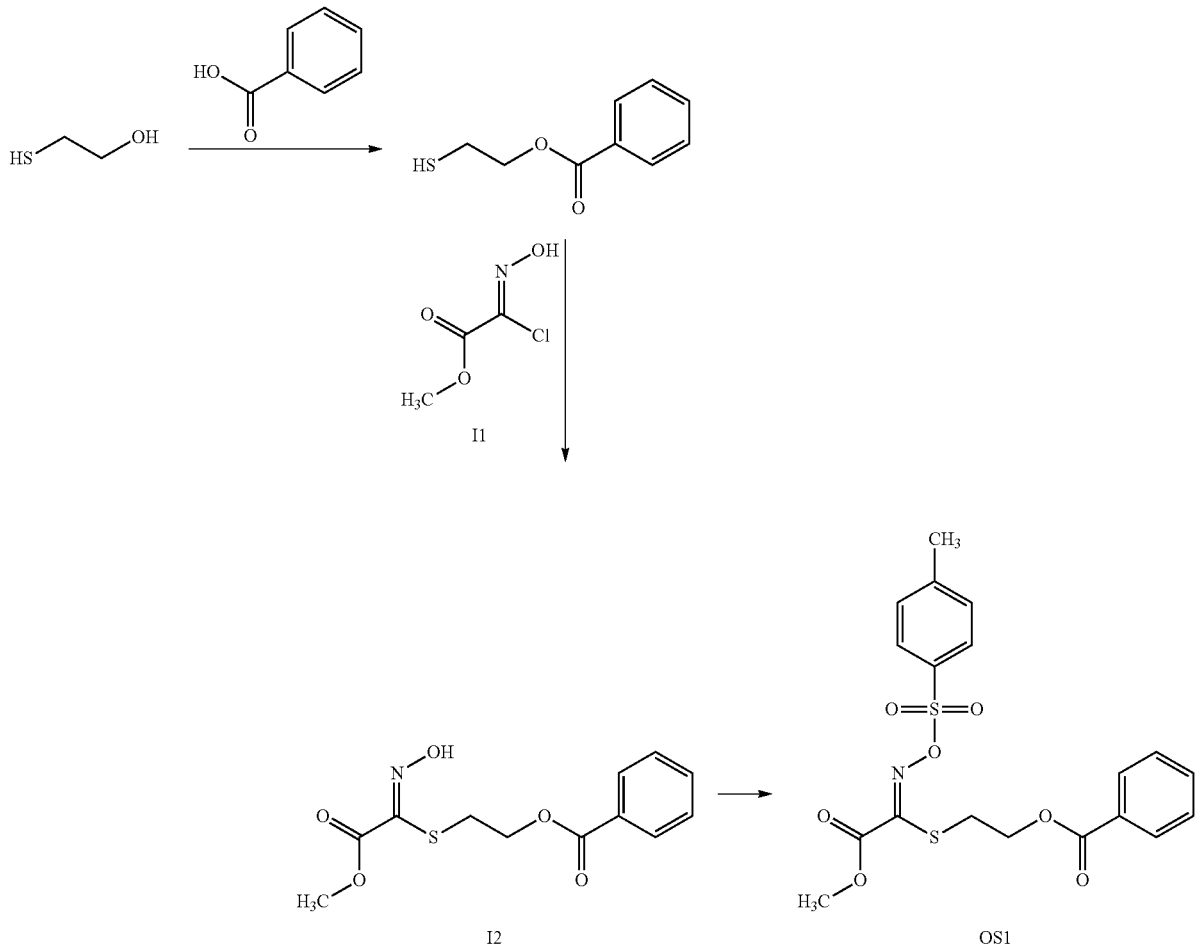

(1.1) Preparation of 2-benzoyloxyethylthiol 11.8 g of 2-mercaptoethanol and 12.2 g of benzoic acid are combined in 50 mL of xylene. To this solution are added 0.36 g of Ti(O"Bu)$_4$, and the mixture is heated to reflux for 18 hours. The resulting water is removed by Dean-Stark trap during reflux. After cooling down, water and ethyl acetate are added to the reaction mixture. The organic layer is separated from the aq. layer and washed with water twice and then brine, followed by drying over anhydrous MgSO$_4$. 18.4 g of colorless oil is obtained and used for next reaction without further purification.

(1.2) Preparation of Intermediate I2

6.87 g of intermediate I1, which is prepared according to the procedure described in WO2012101245, and 11.4 g of 2-benzoyloxyethylthiol are dissolved in 40 mL of ethyl acetate. To this solution are added 6.38 g of triethyl amine in 10 mL of ethyl acetate dropwise over 20 min. under cooling with an ice bath. After completion of the addition, the reaction mixture is further stirred at room temp. for 1.5 hours. After adding water, the organic layer is separated from the aq. layer and washed with water twice and then brine, followed by drying over anhydrous MgSO$_4$. After concentration of the organic layer, the resulting pale brown solid is washed with a mixture of t-buthyl methyl ether and hexane, and 8.54 g of white solid is obtained.

(1.3) Preparation of OS1

8.36 g of intermediate I2 and 5.94 g of p-toluenesulfonyl chloride are dissolved in 60 mL of ethyl acetate. To this solution are added 3.29 g of triethyl amine in 5 mL of ethyl acetate dropwise over 10 min. under cooling with an ice bath. After completion of the addition, the reaction mixture is further stirred at room temp. for 14 hours. After adding water, the organic layer is separated from the aq. layer and washed with water twice and then brine, followed by drying over anhydrous MgSO$_4$. After concentration of the organic layer, the resulting solid is recrystallized from a mixture of CH$_2$Cl$_2$ and hexane, and 7.88 g of white solid is obtained.

Preparation of OS13

OS13 is prepared as described in the following scheme.

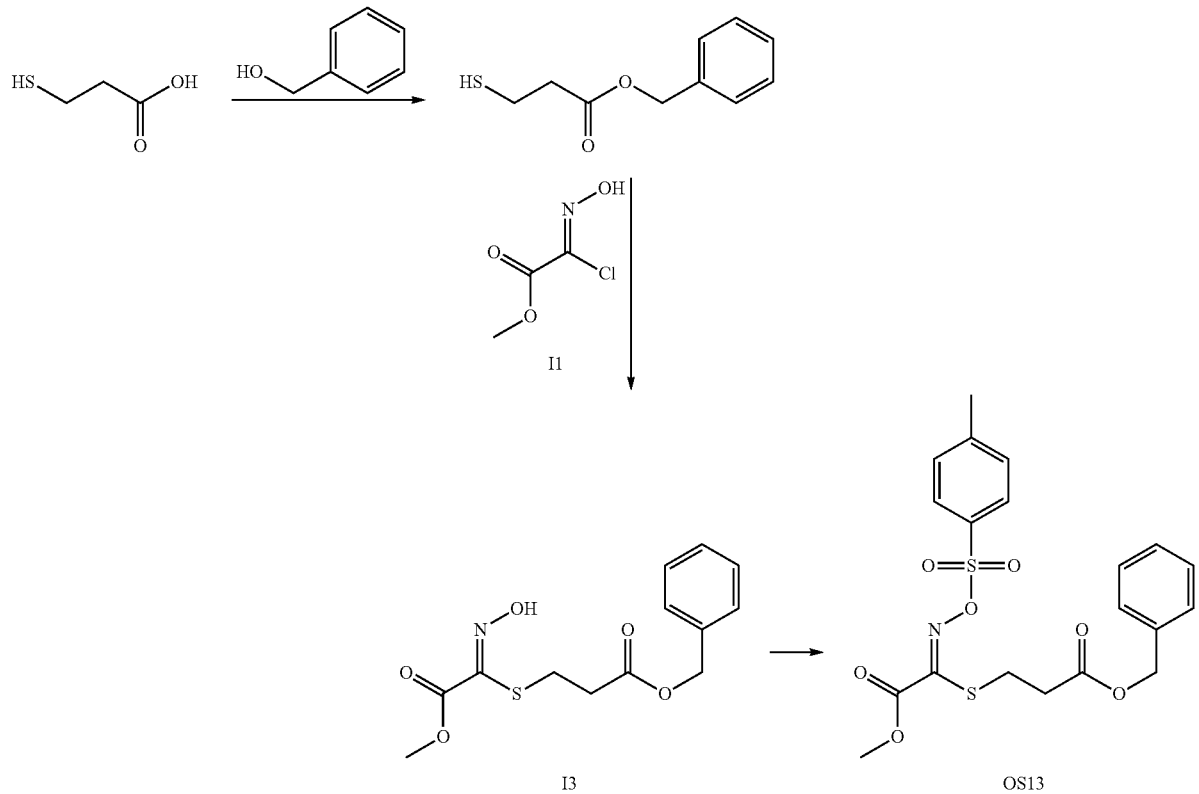

(I3.1) Preparation of Benzyl 2-mercaptopropanoate 2.19 g of 2-mercaptopropanoic acid and 2.28 g of benzyl alcohol are combined in 10 mL of toluene. To this solution are added 3 drops of conc. H$_2$SO$_4$, and the mixture is heated to reflux for 100 minutes. The resulting water is removed by Dean-Stark trap during reflux. After cooling down, water and ethyl acetate are added to the reaction mixture. The organic layer is separated from the aq. layer and washed with water twice, NaHCO$_3$ aq. solution and then brine, followed by drying over anhydrous MgSO$_4$. 3.95 g of colorless oil is obtained and used for next reaction without further purification.

(13.2) Preparation of Intermediate I3

The intermediate I3 is prepared by the procedure given for example 1.2 and obtained as pale yellow oil.

(13.3) Preparation of Intermediate OS13

The title compound is prepared by the procedure given for example 1.3. The title compound is obtained as colorless resin.

The following novel oxime sulfonate compounds are prepared in a similar manner.

| Oxime sulfonate (OS) | Structure | $^1$H NMR in CDCl$_3$ |
|---|---|---|
| OS1 | 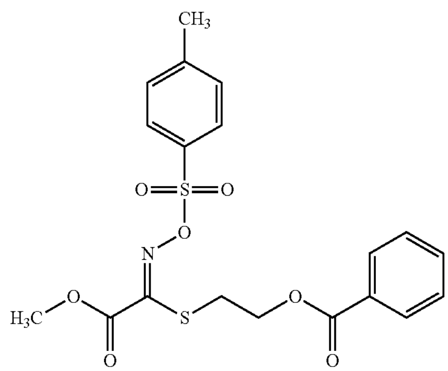 [SMILES: COC(=O)/C(=N/OS(=O)(=O)c1ccc(C)cc1)SCCOC(=O)c1ccccc1] | 2.44 (s, 3H), 3.35 (t, 2H), 3.84 (s, 3H), 4.45 (t, 2H), 7.33 (d, 2H), 7.44 (t, 2H), 7.59 (t, 1H), 7.86 (d, 2H), 8.02 (d, 2H) |
| OS2 | 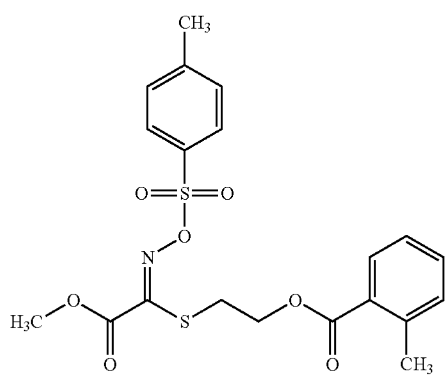 [SMILES: COC(=O)/C(=N/OS(=O)(=O)c1ccc(C)cc1)SCCOC(=O)c1ccccc1C] | 2.45 (s, 3H), 2.56 (s, 3H), 3.35 (t, 2H), 3.81 (s, 3H), 4.42 (t, 2H), 7.20-7.30 (m, 2H), 7.34 (d, 2H), 7.42 (t, 1H), 7.83-7.90 (m, 3H) |
| OS3 | 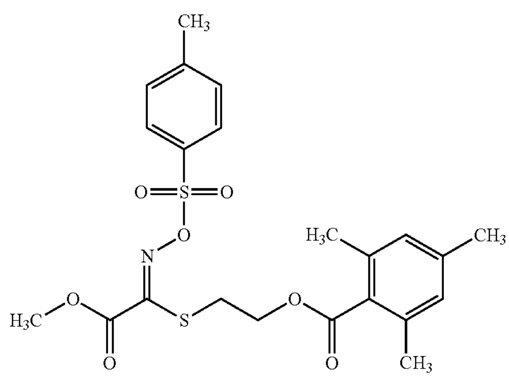 | 2.20 (s, 6H), 2.28 (s, 3H), 2.47 (s, 3H), 3.36 (t, 2H), 3.58 (s, 3H), 4.41 (t, 2H), 6.83 (s, 2H), 7.35 (d, 2H), 7.87 (d, 2H) |

-continued

| Oxime sulfonate (OS) | Structure | $^1$H NMR in CDCl$_3$ |
|---|---|---|
| OS4 | 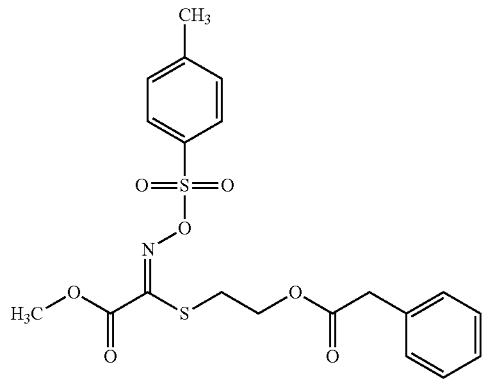 [SMILES: COC(=O)/C(=N/OS(=O)(=O)c1ccc(C)cc1)SCCOC(=O)Cc1ccccc1] | 2.44 (s, 3H), 3.22 (t, 2H), 3.58 (s, 2H), 3.87 (s, 3H), 4.21 (t, 2H), 7.22-7.37 (m, 7H), 7.87 (d, 2H) |
| OS5 | 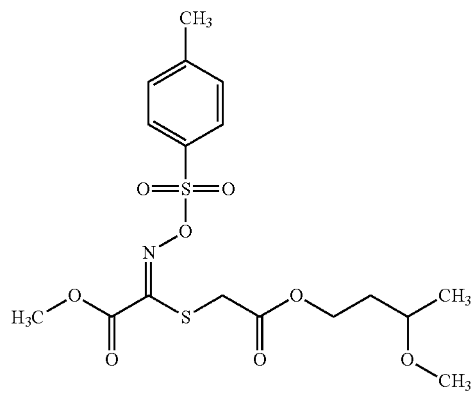 | 1.14 (d, 3H), 1.73-1.76 (m, 2H), 2.46 (s, 3H), 3.26 (s, 3H), 3.31-3.41 (m, 1H), 3.82 (s, 2H), 3.84 (s, 3H), 4.20 (t, 2H), 7.35 (d, 2H), 7.87 (d, 2H) |
| OS6 | 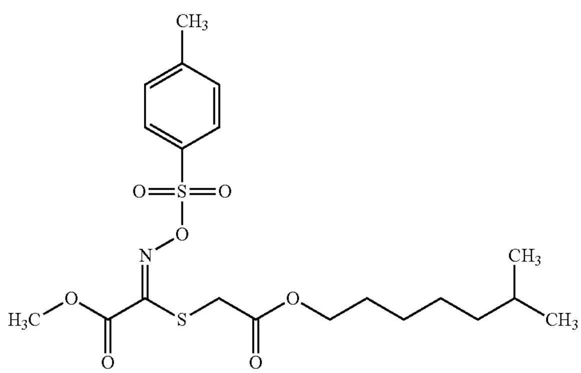 [SMILES: COC(=O)/C(=N/OS(=O)(=O)c1ccc(C)cc1)SCC(=O)OCCCCCC(C)C] | 0.76-1.62 (m, 15H), 2.46 (s, 3H), 3.83 (s, 2H), 3.84 (s, 3H), 4.06-4.13 (m, 2H), 7.35 (d, 2H), 7.87 (d, 2H) |
| OS7 | 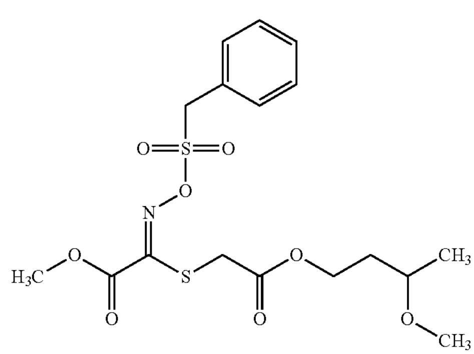 | 1.17 (d, 3H), 1.74-1.84 (m, 2H), 3.31 (s, 2H), 3.36-3.44 (m, 1H), 3.87 (s, 2H), 3.94 (s, 3H), 4.25 (t, 2H), 4.59 (s, 2H), 7.49 (br, 5H) |

-continued

| Oxime sulfonate (OS) | Structure | ¹H NMR in CDCl₃ |
|---|---|---|
| OS8 | 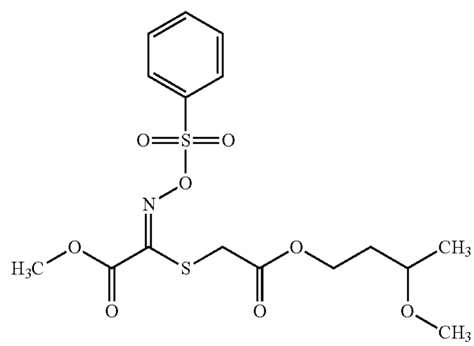 | 1.13 (d, 3H), 1.70-1.79 (m, 2H), 3.28 (s, 3H), 3.32-3.41 (m, 1H), 4.20 (t, 2H), 7.57 (t, 2H), 7.69 (t, 1H), 7.99 (d, 2H) |
| OS9 | 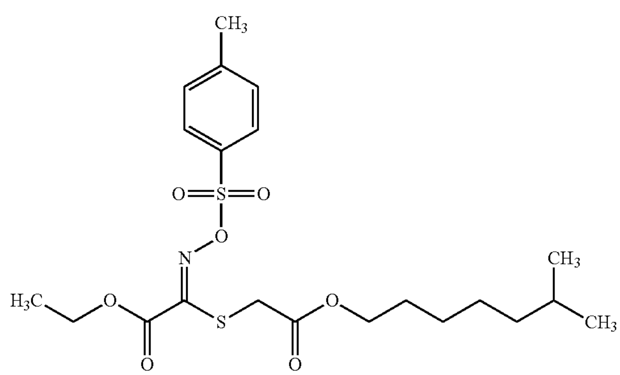 [SMILES: CCOC(=O)/C(=N/OS(=O)(=O)c1ccc(C)cc1)SCC(=O)OCCCCCC(C)C] | 0.83-1.66 (m, 15H), 2.46 (s, 3H), 3.82 (s, 2H), 4.06-4.14 (m, 2H), 4.29 (q, 2H), 7.34 (d, 2H), 7.87 (d, 2H) |
| OS10 | 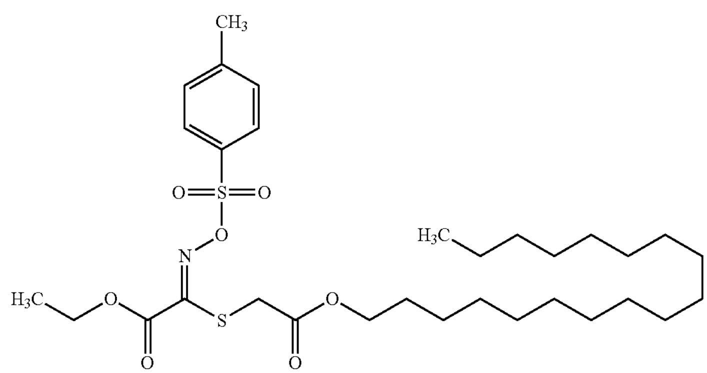 [SMILES: CCCCCCCCCCCCCCCCCCOC(=O)CS/C(=N\OS(=O)(=O)c1ccc(C)cc1)C(=O)OCC] | 0.88 (t, 3H), 1.26-1.66 (m, 35H), 2.46 (s, 3H), 3.82 (s, 2H), 4.08 (t, 2H), 4.29 (q, 2H), 7.34 (d, 2H), 7.87 (d, 2H) |
| OS11 | 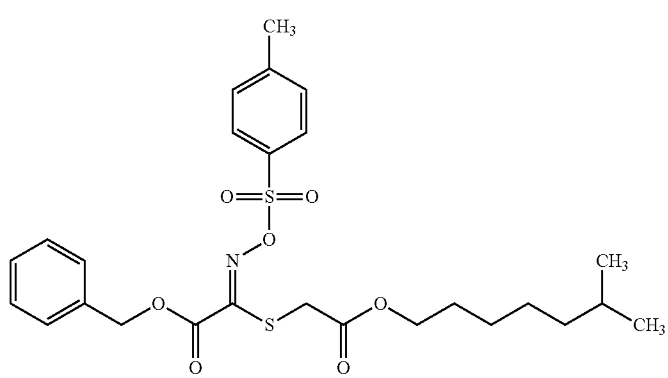 [SMILES: Cc1ccc(S(=O)(=O)O/N=C(\SCC(=O)OCCCCCC(C)C)C(=O)OCc2ccccc2)cc1] | 0.82-1.66 (m, 15H), 2.44 (s, 3H), 3.79 (s, 2H), 3.97-4.07 (m, 2H), 7.33 (d, 2H), 7.37 (br, 5H), 7.85 (d, 2H) |

-continued
| Oxime sulfonate (OS) | Structure | ¹H NMR in CDCl₃ |
|---|---|---|
| OS12 | 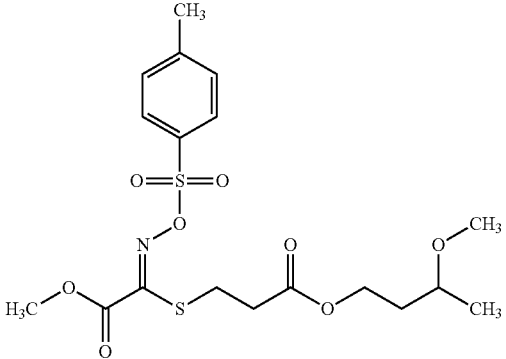 | 1.16 (d, 3H), 1.74-1.83 (m, 2H), 2.45 (s, 3H), 2.64 (t, 2H), 3.19 (t, 2H), 3.31 (s, 3H), 3.38-3.42 (m, 1H), 4.20 (t, 2H), 7.35 (d, 2H), 7.85 (d, 2H) |
| OS13 | 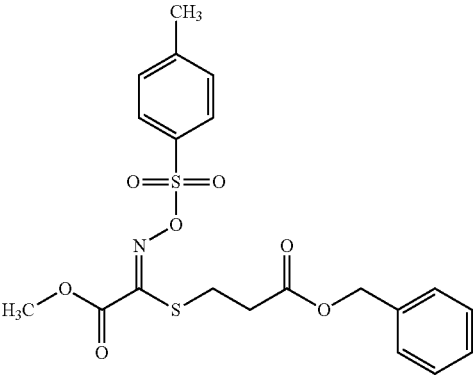 [SMILES: COC(=O)/C(=N/OS(=O)(=O)c1ccc(C)cc1)SCCC(=O)OCc1ccccc1] | 2.44 (s, 3H), 2.69 (t, 2H), 3.20 (t, 2H), 3.85 (s, 3H), 5.13 (s, 2H), 7.30-7.41 (m, 7H), 7.85 (d, 2H) |
| OS14 | 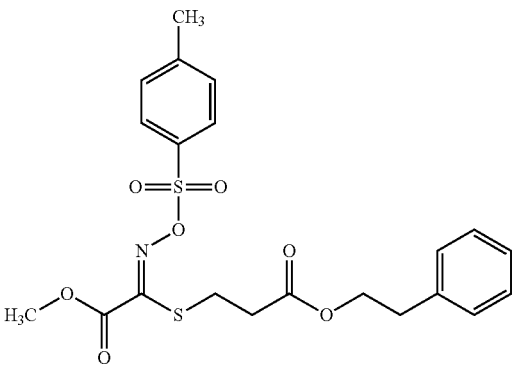 [SMILES: COC(=O)/C(=N/OS(=O)(=O)c1ccc(C)cc1)SCCC(=O)OCCc1ccccc1] | 2.44 (s, 3H), 2.62 (t, 2H), 2.93 (t, 2H), 3.14 (t, 2H), 3.86 (s, 3H), 4.31 (t, 2H), 7.17-7.27 (m, 3H), 7.28-7.36 (m, 4H), 7.85 (d, 2H) |
| OS15 | 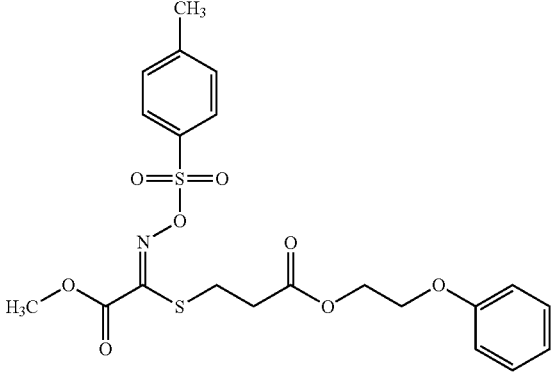 [SMILES: COC(=O)/C(=N/OS(=O)(=O)c1ccc(C)cc1)SCCC(=O)OCCOc1ccccc1] | 2.45 (s, 3H), 2.70 (t, 2H), 3.19 (t, 2H), 3.86 (s, 3H), 4.17 (dd, 2H), 4.45 (dd, 2H), 6.91 (d, 2H), 6.98 (t, 1H), 7.30 (t, 2H), 7.34 (d, 2H), 7.85 (d, 2H) |

-continued

| Oxime sulfonate (OS) | Structure | $^1$H NMR in CDCl$_3$ |
|---|---|---|
| OS16 | [structure] | 2.45 (s, 3H), 2.62 (t, 2H), 3.14 (t, 2H), 3.87 (s, 3H), 3.95 (t, 2H), 4.34 (t, 2H), 7.34 (d, 2H), 7.72-7.78 (m, 2H), 7.82-7.90 (m, 4H) |
| OS17 | [structure] | 1.25-1.50 (m, 20H), 1.63-1.76 (m, 2H), 2.45 (s, 3H), 2.61 (t, 2H), 3.17 (t, 2H), 3.88 (s, 3H), 4.98-5.07 (m, 1H), 7.34 (d, 2H), 7.86 (d, 2H) |
| OS18 | [structure] | 2.45 (s, 3H), 2.73 (t, 2H), 3.31 (t, 2H), 3.88 (s, 3H), 7.13 (t, 1H), 7.30-7.37 (m, 4H), 7.50 (d, 2H), 7.85 (d, 2H) |

Application Examples

Preparation of Acrylate Formulation (Clear)

| | |
|---|---|
| 3.8 parts by weight | solvent (PGMEA) |
| 2.6 parts by weight | alkaline developable binder, 37.8% solution (Ripoxy SPC-2000, provided by Showa Highpolymer) |
| 1.0 parts by weight | multifunctional acrylate (DPHA, provided by UCB Chemicals) |

Thermal Curing Tests of Acrylate Formulation
Thermogravimetric Analysis of Dry Film Containing Oxime Sulfonate: Test A The oxime sulfonate to be tested and additionally Irgacure® 369 (12.5 wt % in solid, provided by BASF) as photoinitiator are added to the above clear resist composition and mixed. The mixture is applied to a glass substrate using a spin coater (1H-DX2, MIKASA). The solvent is removed by heating at 80° C. for 2 min in a convection oven. Exposure is then carried out using a 250 W super high pressure mercury lamp (USHIO, USH-250BY) at a distance of 15 cm. The total exposure dose determined by measuring the light intensity with an optical power meter (ORC UV Light Measure Model UV-M02 with UV-35 detector) is 150 mJ/cm$^2$. The thickness of the dry film is approximately 2.5 µm. The coating film is flaked and filled the aluminum cell with approximately 5 mg. Thermal weight loss is measured by thermogravimetric analysis (Shimadzu, DTAG-60/60H). The rate of temperature increase is 10° C./minutes and the flaked film in the aluminum cell is baked at 230° C. for 30 minutes. The lower weight loss is required to reduce contamination of a baking equipment or a substrate in use.

The results of the tests are given in table 1.

Thermal Curing Tests of Acrylate Formulation after Photocuring: Test B

The oxime sulfonate to be tested and additionally Irgacure® 369 (12.5 wt % in solid) as photoinitiator are added to the above clear resist composition and mixed. The mixture is applied to a Si Wafer using a spin coater (1H-DX2, MIKASA). The solvent is removed by heating at 80° C. for 2 min in a convection oven. Exposure is then carried out using a 250 W super high pressure mercury lamp (USHIO, USH-250BY) at a distance of 15 cm. The total exposure dose determined by measuring light intensity with an optical power meter (ORC UV Light Measure Model UV-M02 with UV-35 detector) is 150 mJ/cm². The thickness of the dry film is approximately 2.5 μm. The coating is further baked at 180° C. for 30 min. The conversion of the acrylic group in baking is determined by measuring IR absorption at 810 cm$^{-1}$, with a FT-IR spectrometer (FT-720, HORIBA) before and after baking. The results of the tests are given in table 1.

TABLE 1

| Oxime sulfonate (OS) | Concentration of OS (wt % in solid contents of composition) | Molecular weight | Percentage of weight loss/% | Conversion of acrylate/% |
|---|---|---|---|---|
| OS1 | 5 | 437.5 | 7.9 | 69.5 |
| OS2 | 5 | 451.5 | 7.6 | 70.1 |
| OS3 | 5 | 479.6 | 7.9 | 70.2 |
| OS4 | 5 | 451.5 | 7.3 | 68.3 |
| OS5 | 5 | 433.5 | 7.7 | 67.8 |
| OS6 | 5 | 459.9 | 7.1 | 69.2 |
| OS8 | 5 | 419.5 | 7.4 | 70.0 |
| OS9 | 5 | 473.6 | 7.3 | 66.3 |
| OS10 | 5 | 613.9 | 7.6 | 66.0 |
| OS11 | 5 | 535.7 | 8.2 | 67.9 |
| OS12 | 5 | 447.5 | 7.7 | 68.3 |
| OS13 | 5 | 451.5 | 6.9 | 69.7 |
| OS14 | 5 | 465.6 | 6.9 | 70.1 |
| OS15 | 5 | 481.6 | 7.2 | 68.9 |
| OS16 | 5 | 534.6 | 8.2 | 70.1 |
| OS17 | 5 | 527.7 | 5.9 | 67.8 |
| OS18 | 5 | 436.5 | 7.4 | 69.9 |
| No OS | 0 | 0 | 7.7 | 64.6 |
| Comparison Example 1 | 5 | 497.7 | 10.4 | 62.8 |
| Comparison Example 2 | 5 | 377.4 | 8.8 | 69.8 |

Comparison example 1

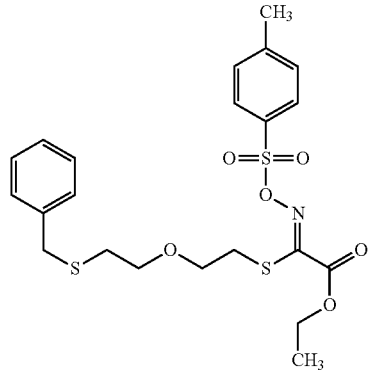 [SMILES: CCOC(=O)/C(=N/OS(=O)(=O)c1ccc(C)cc1)SCCOCCSCc1ccccc1]

Comparison example 2

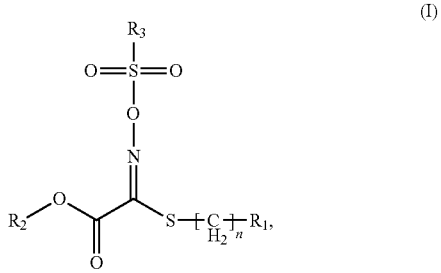

The invention claimed is:

1. A compound of formula (I)

$$\text{(I)}$$

wherein:
R₁ is O(CO)R₄, COOR₅ or CONR₆R₇;
n is 1 or 2;
R₂ is C₁-C₈ alkyl, C₂-C₈ alkyl which is interrupted by one or more O, or C₃-C₆ cycloalkyl, which is uninterrupted or is interrupted by one or more O;
or R₂ is benzyl, which is unsubstituted or is substituted by one or more C₁-C₆ alkyl, C₁-C₄ haloalkyl, halogen, CN, NO₂, C₁-C₆ alkylsulfanyl or C₁-C₆ alkoxy;
R₃ is C₁-C₈ alkyl, C₃-C₆ cycloalkyl, C₁-C₈ haloalkyl or C₂-C₈ alkenyl;
or R₃ is benzyl, phenyl or naphthyl, where the benzyl, phenyl or naphthyl is unsubstituted or substituted by one or more C₁-C₆ alkyl, C₁-C₄ haloalkyl, halogen, CN, NO₂, C₁-C₆ alkylsulfanyl, C₁-C₆ alkoxy, phenyl or COO(C₁-C₆ alkyl);
R₄ is C₁-C₈ alkyl, C₃-C₆ cycloalkyl, C₁-C₈ haloalkyl or C₂-C₈ alkenyl;
or R₄ is benzyl, phenyl or naphthyl, where the benzyl, phenyl or naphthyl are unsubstituted or substituted by one or more C₁-C₆ alkyl, C₁-C₄ haloalkyl, halogen, CN, NO₂, C₁-C₆ alkylsulfanyl, phenylsulfanyl, C₁-C₆ alkoxy, phenoxy, phenyl or COO(C₁-C₆ alkyl);
R₅ is C₃-C₂₀ alkyl, C₃-C₁₄ cycloalkyl or C₂-C₈ alkenyl;
or R₅ is C₁-C₁₂ alkyl substituted by one or more halogen, CN, phenylsulfanyl, phenoxy, N(C₁-C₆ alkyl)₂, N(phenyl)₂, phthalimido, phenyl or phenyl substituted by one or more C₁-C₁₂ alkyl, C₁-C₄ haloalkyl, halogen, CN, NO₂, C₁-C₆ alkylsulfanyl phenylsulfanyl, C₁-C₆ alkoxy, phenoxy, N(C₁-C₆ alkyl)₂, N(phenyl)₂;

or $R_5$ is $C_2$-$C_{12}$ alkyl or $C_3$-$C_6$ cycloalkyl, each of which is interrupted by one or more O or S;

or $R_5$ is phenyl or naphthyl, where the phenyl or naphthyl are unsubstituted or substituted by one or more $C_1$-$C_6$ alkyl, $C_1$-$C_4$ haloalkyl, halogen, CN, $NO_2$, $C_1$-$C_6$ alkylsulfanyl, $C_1$-$C_6$ alkoxy, phenyl or COO($C_1$-$C_6$ alkyl);

$R_6$ and $R_7$ each independently are hydrogen, $C_1$-$C_{12}$ alkyl, $C_1$-$C_4$ haloalkyl, phenyl-$C_1$-$C_4$ alkyl, $C_2$-$C_8$ alkenyl or $C_3$-$C_6$ cycloalkyl, or $R_6$ and $R_7$ are $C_2$-$C_{12}$ alkyl which is interrupted by O, S, N($C_1$-$C_8$ alkyl) or CO, or $R_6$ and $R_7$ are $C_2$-$C_4$ haloalkyl which is interrupted by O, S, N($C_1$-$C_8$ alkyl) or CO, or $R_6$ and $R_7$ each independently are phenyl-$C_1$-$C_4$ alkyl which is interrupted by O, S, N($C_1$-$C_8$ alkyl) or CO;

or $R_6$ and $R_7$ are $C_2$-$C_8$ alkenyl which is interrupted by O, S, N($C_1$-$C_8$ alkyl) or CO;

or $R_6$ and $R_7$ are $C_3$-$C_6$ cycloalkyl which is interrupted by O, S, N($C_1$-$C_8$ alkyl) or CO, or $R_6$ and $R_7$ each independently are phenyl or naphthyl, where the phenyl or naphthyl is unsubstituted or is substituted by one or more $C_1$-$C_6$ alkyl, $C_1$-$C_4$ haloalkyl, halogen, CN, $NO_2$, $C_1$-$C_6$ alkylsulfanyl, $C_1$-$C_6$ alkoxy, phenyl or COO($C_1$-$C_6$ alkyl); or $R_6$ and $R_7$, together with the N-atom to which $R_6$ and $R_7$ are attached, form a 5- or 6-membered ring via $C_2$-$C_5$alkylene, where the $C_2$-$C_5$ alkylene ring is uninterrupted or interrupted by one or more O, S, N($C_1$-$C_8$ alkyl), NH or CO.

2. The compound according to claim 1, wherein in formula (I):

$R_1$ is O(CO)$R_4$, COO$R_5$ or CON$R_6R_7$;

n is 1 or 2;

$R_2$ is $C_1$-$C_4$ alkyl or benzyl;

$R_3$ is benzyl, phenyl or phenyl substituted by one or more $C_1$-$C_6$ alkyl;

$R_4$ is benzyl, phenyl or phenyl substituted by one or more $C_1$-$C_6$ alkyl;

$R_5$ is $C_3$-$C_{18}$ alkyl or $C_3$-$C_{12}$ cycloalkyl, or $R_5$ is $C_2$-$C_{12}$ alkyl which is interrupted by one or more O, or $R_5$ is $C_1$-$C_6$ alkyl substituted by phenylsulfanyl, phenoxy, N($C_1$-$C_6$ alkyl)$_2$, N(phenyl)$_2$, phthalimido, phenyl or phenyl substituted by one or more $C_1$-$C_{12}$ alkyl;

$R_6$ and $R_7$ each independently are hydrogen, $C_1$-$C_6$ alkyl or phenyl, or together with the N-atom to which $R_6$ and $R_7$ are attached form a morpholino ring.

3. The compound according to claim 1, wherein in formula (I):

$R_1$ is O(CO)$R_4$, COO$R_5$ or CON$R_6R_7$;

n is 1 or 2

$R_2$ is methyl, ethyl or benzyl $R_3$ is benzyl, phenyl or phenyl substituted by $C_1$-$C_6$ alkyl;

$R_4$ is benzyl, phenyl or phenyl substituted by one or more $C_1$-$C_6$ alkyl;

$R_5$ is $C_3$-$C_{18}$ alkyl or $C_3$-$C_{12}$ cycloalkyl, or $R_5$ is $C_2$-$C_{12}$ alkyl interrupted by one or more O, or $R_5$ is $C_1$-$C_6$ alkyl substituted by phenyl, phenoxy or phthalimido;

$R_6$ and $R_7$ each independently are hydrogen or phenyl.

4. A polymerizable composition, comprising, (a) a monomeric, oligomeric or polymeric compound comprising at least one ethylenically unsaturated double bond; and (b) at least one compound of the formula I according to claim 1.

5. The polymerizable composition according to claim 4, further comprising at least one photoinitiator (c).

6. The polymerizable composition according to claim 4, further comprising a binder polymer (d).

7. The polymerizable composition according to claim 6, further comprising at least one component (e) selected from the group consisting of (e1) a pigment, (e2) a dye, (e3) a filler, (e4) a dispersant, (e5) a sensitizer, (e6) a thermosetting compound, which is different from the compound of the formula (I) and the binder polymer (d), and a mixture thereof.

8. The polymerizable composition according to claim 7, comprising the component (e5), which comprises a compound selected from the group consisting of benzophenone and a derivative thereof, thioxanthone and a derivative thereof, anthraquinone and a derivative thereof, and coumarin and a derivative thereof.

9. The polymerizable composition according to claim 4, comprising:

(a) at least one acrylate monomer, (b) at least one compound of the formula I, (c) at least one photoinitiator, and (d) at least one alkaline developable resin.

10. The polymerizable composition according to claim 4, comprising the component (a) in an amount of from 0.01 to 50% by weight, based on a total weight of the composition.

11. A process for thermally polymerizing a composition containing ethylenically unsaturated double bonds, the processing comprising:

heating the polymerizable composition according to claim 4.

12. The process according to claim 11, wherein the heating occurs at a temperature of from 80° C. to 260° C.

13. An article, obtained by the process according to claim 12, wherein the article is a color filter, a spacer for LCD, an overcoat layer for color filter and LCD, a sealant for LCD and OLED, an optical film, an anisotropy conducting adhesive for LCD, an insulation/passivation layer for LCD, an organic light-emitting diode display, a touch panel, a flexible display, a bank/pixel definition layer of OLED, an insulation for metal wiring/transparent conductive film for touch panel, a coating for touch panel, a hard coat and optical coat, decorative ink for touch panel, a protective film for touch panel, an etching resist for touch panel, or a structure or a layer in manufacturing a plasma-display panel, an electroluminescence display, an organic light-emitting diode display, a touch panel, a flexible display and LCD, or a solder mask or a dielectric layer in a sequential build-up layer of a printed circuit board.

14. A resist, comprising:

the polymerizable composition according to claim 4 wherein the resist is suitable for making a color filter, a spacer for LCD, an overcoat layer for color filter and LCD, a sealant for LCD and OLED, an optical film, an anisotropy conducting adhesive for LCD, an insulation/passivation layer for LCD, an organic light-emitting diode display, a touch panel, a flexible display, a bank/pixel definition layer of OLED, an insulation for metal wiring/transparent conductive film for touch panel, a coating for touch panel, a hard coat and optical coat, decorative ink for touch panel, a protective film for touch panel, an etching resist for touch panel, or a resist or a photosensitive composition to generate a structure or a layer in manufacturing a plasma-display panel, an electroluminescence display, an organic light-emitting diode display, a touch panel, a flexible display and LCD, or a solder resist, or a photoresist material for forming a dielectric layer in a sequential build-up layer of a printed circuit board.

15. A coated substrate, which is coated on at least one surface with the polymerizable composition according to claim 4.

16. A color filter, obtained by a process comprising providing red, green and blue picture elements and optionally a black matrix, all comprising a photosensitive resin and a pigment on a transparent substrate and providing a transparent electrode either on a surface of the substrate or on a surface of the color filter, wherein the photosensitive resin comprises a polyfunctional acrylate monomer, an organic polymer binder, a photopolymerization initiator and at least one compound of the formula I according to claim 1.

17. A method for preparing the compound of the formula (I) according to claim 1, the method comprising reacting a free oxime of formula (IA)

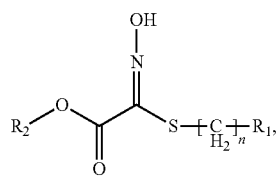
(IA)

wherein $R_1$ is $O(CO)R_4$, $COOR_5$ or $CONR_6R_7$;

n is 1 or 2; and $R_2$ is $C_1$-$C_8$ alkyl, $C_2$-$C_8$ alkyl which is interrupted by one or more O, or $C_3$-$C_6$ cycloalkyl, which is uninterrupted or is interrupted by one or more O, with a sulfonic acid halide of formula (IB)

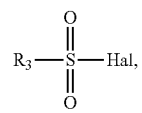
(IB)

wherein $R_3$ is $C_1$-$C_8$ alkyl, $C_3$-$C_6$ cycloalkyl, $C_1$-$C_8$ haloalkyl or $C_2$-$C_8$ alkenyl; and Hal is a halogen.

* * * * *